US009745596B2

(12) United States Patent
Olivier et al.

(10) Patent No.: US 9,745,596 B2
(45) **Date of Patent: *Aug. 29, 2017**

(54) IDENTIFICATION AND USE OF KRP MUTANTS IN WHEAT

(71) Applicants: Targeted Growth, Inc., Seattle, WA (US); The Regents of the University of California, Oakland, CA (US)

(72) Inventors: Jean Paul Olivier, Seattle, WA (US); Tom Todaro, Seattle, WA (US); Jorge Dubcovsky, Davis, CA (US); Wenjun Zhang, Davis, CA (US)

(73) Assignees: Targeted Growth, Inc., Burien, WA (US); The Regents of the University of California, Oakland, CA (US)

( * ) Notice: Subject to any disclaimer, the term of this patent is extended or adjusted under 35 U.S.C. 154(b) by 71 days.

This patent is subject to a terminal disclaimer.

(21) Appl. No.: 14/715,317

(22) Filed: May 18, 2015

(65) Prior Publication Data

US 2016/0002656 A1 Jan. 7, 2016

Related U.S. Application Data

(63) Continuation of application No. 13/444,305, filed on Apr. 11, 2012, now Pat. No. 9,062,323.

(60) Provisional application No. 61/474,203, filed on Apr. 11, 2011.

(51) Int. Cl.

| | |
|---|---|
| ***C12N 15/01*** | (2006.01) |
| ***C12N 15/82*** | (2006.01) |
| ***A01H 1/04*** | (2006.01) |
| ***A01H 5/10*** | (2006.01) |
| ***C07K 14/415*** | (2006.01) |

(52) U.S. Cl.

CPC .......... *C12N 15/8261* (2013.01); *A01H 1/04* (2013.01); *A01H 5/10* (2013.01); *C07K 14/415* (2013.01)

(58) Field of Classification Search

None

See application file for complete search history.

(56) References Cited

U.S. PATENT DOCUMENTS

| | | | | |
|---|---|---|---|---|
| 5,958,769 | A | 9/1999 | Roberts et al. | |
| 6,087,175 | A | 7/2000 | John | |
| 6,114,608 | A | 9/2000 | Mettler et al. | |
| 6,559,358 | B1 | 5/2003 | Murray | |
| 6,710,227 | B1 | 3/2004 | Inze et al. | |
| 7,122,658 | B1 | 10/2006 | Lappegard et al. | |
| 7,329,799 | B2 | 2/2008 | Savidge et al. | |
| 7,553,954 | B2 * | 6/2009 | Andersen ............ | C07K 14/415 536/23.6 |
| 7,803,990 | B2 | 9/2010 | Abbitt | |
| 8,431,775 | B2 | 4/2013 | Hegstad et al. | |
| 8,742,205 | B2 | 6/2014 | Olivier et al. | |
| 9,062,323 | B2 * | 6/2015 | Olivier .................... | A01H 1/04 |
| 2004/0019926 | A1 | 1/2004 | Frankard et al. | |
| 2007/0044171 | A1 | 2/2007 | Kovalic et al. | |
| 2007/0056058 | A1 * | 3/2007 | Olivier ................ | C07K 14/415 800/290 |
| 2008/0134355 | A1 | 6/2008 | Van Camp | |
| 2008/0216193 | A1 | 9/2008 | Savidge et al. | |
| 2008/0307546 | A1 | 12/2008 | Veylder et al. | |
| 2009/0070894 | A1 | 3/2009 | Frankard et al. | |
| 2009/0087878 | A9 | 4/2009 | La Rosa et al. | |
| 2009/0144863 | A1 | 6/2009 | Song et al. | |
| 2011/0135647 | A1 | 6/2011 | Nakamura et al. | |
| 2012/0131698 | A1 | 5/2012 | Olivier et al. | |
| 2012/0284813 | A1 | 11/2012 | Olivier et al. | |
| 2014/0143900 | A1 | 5/2014 | Olivier et al. | |
| 2014/0331362 | A1 | 11/2014 | Olivier et al. | |

FOREIGN PATENT DOCUMENTS

| | | | |
|---|---|---|---|
| WO | WO 99/64599 | A1 | 12/1999 |
| WO | WO 00/60087 | A2 | 10/2000 |
| WO | WO 02/081623 | A2 | 10/2002 |
| WO | WO 2005/007829 | A2 | 1/2005 |
| WO | WO 2005/024029 | A2 | 3/2005 |
| WO | WO 2006/081029 | A2 | 8/2006 |
| WO | WO 2007/016319 | A2 | 2/2007 |
| WO | WO 2009/092009 | A2 | 7/2009 |
| WO | WO 2010/099083 | A1 | 9/2010 |
| WO | WO 2012/142116 | A2 | 10/2012 |

OTHER PUBLICATIONS

Cheng et al, 2013, Plant J., 75:642-655.*

Blanco et al, 2006, Theor. Appl. Genet., 112:1195-1204.*

European Patent Application No. 11186399.9, Extended European Search Report dated Mar. 21, 2012, 8 pages.

U.S. Appl. No. 14/111,292, Advisory Action mailed Jul. 15, 2016, 5 pages.

European Patent Application No. 15161572.1, Extended European Search Report dated Nov. 9, 2015.

Australian Patent Application No. 2006275753, Office Action mailed Feb. 15, 2011.

Azzi et al., "Interaction Between the Cell-Cycle-Control Proteins $p34^{cdc2}$ and $p9^{CKShs2}$, Evidence for Two Cooperative Binding Domains in $p9^{CKShs2}$," *Eur. J Biochem.* 203:353-360 (1992).

(Continued)

*Primary Examiner* — Jason Deveau Rosen

(74) *Attorney, Agent, or Firm* — Cooley LLP

(57) ABSTRACT

The invention provides a wheat cell, part, tissue culture or whole plant comprising at least one disrupted KRP gene of the present invention. The present invention also provides methods of increasing weight, size, and/or number of one or more organs, and/or yield of a wheat plant by utilizing the disrupted KRP genes of the present invention. Furthermore, methods of breeding wheat plants to produce new wheat plants having increased weight, size, and/or number of one or more organs, and/or yield are provided. The present invention provides isolated Kinase Inhibitor Protein (KIP) Related Protein (KRP) polynucleotide sequences and isolated KRP polypeptide sequences and methods of their use.

3 Claims, 3 Drawing Sheets

(56) References Cited

OTHER PUBLICATIONS

Canadian Patent Application No. 2,619,383, Office Action mailed Nov. 2, 2012.
Cheng et al., "Downregulation of multiple CDK inhibitor ICK/KRP genes upregulates the E2F pathway and increases cell proliferation, and organ and seed sizes in Arabidopsis", *The Plant Journal*, 75: 642-655 (2013).
Chinese Patent Application No. 200680036207.8, Office Action and English translation mailed Nov. 9, 2010.
Chinese Patent Application No. 200680036207.8, Office Action and English translation mailed Dec. 23, 2011.
Chinese Patent Application No. 200680036207.8, Office Action mailed May 21, 2015 (with English translation).
Coats et al., "Requirement of $p27^{Kip1}$ for Restriction Point Control of the Fibroblast Cell Cycle," *Science*, 272: 877-880 (1996).
Coelho et al., "Cyclin-Dependent Kinase Inhibitors in Maize Endosperm and Their Potential Role in Endoreduplication", *Plant Physiology*, 138: 2323-2336 (2005).
De Veylder et al., "Functional Analysis of Cyclin-Dependent Kinase Inhibitors of Arabidopsis," *Plant Cell*, 13: 1653-1667 (2001).
Devos et al., "Genome Relationships: The Grass Model in Current Research", *The Plant Cell*, 12: 637-646 (2000).
Elmore et al., "Glyphosate-Resistant Soybean Cultivar Response to Glyphosate," *Agron. J.*, 93:404-407 (2001).
Elmore et al., "Glyphosate-Resistant Soybean Cultivar Yields Compared with Sister Lines," *Agron. J.*, 93:408-412 (2001).
European Patent Application No. 06788753.9, Extended European Search Report mailed Apr. 15, 2009.
European Patent Application No. 12771677.7, Extended European Search Report mailed Sep. 1, 2014.
European Patent Application No. 11839924.5, Examination Report dated May 12, 2015.
European Patent Application No. 15161572.1, Partial European Search Report dated Aug. 24, 2015.
Feig and Cooper, "Inhibition of NIH 3T3 Cell Proliferation by a Mutant *ras* Protein with Preferential Affinity for GDP," *Mol. Cell. Biol.*, 8:3235-3243 (1988).
Fernandez-Cornejo, *Agriculture Information Bulletin No. (AIB786)* 81 pp, Feb. 2004.
Fero et al., "A Syndrome of Multiorgan Hyperplasia with Features of Gigantism, Tumorigenesis, and Female Sterility in p27Kipl-Deficient Mice," *Cell*, 85:733-744 (1996).
Firpo et al., "Inactivation of a Cdk2 Inhibitor during Interleukin 2-Induced Proliferation of Human T Lymphocytes," *Mol. Cell. Biol.*, 14:4889-4901 (1994).
Israeli Patent Application No. 189051, English translation of Office Action mailed May 23, 2010.
Israeli Patent Application No. 189051, English translation of Office Action mailed Jun. 23, 2011.
PCT/US2006/029349, International Search Report, mailed Apr. 20, 2007.
PCT/US2006/029349, Written Opinion of the International Searching Authority, mailed Apr. 20, 2007.
PCT/US2006/029349, International Preliminary Report on Patentability, mailed Jan. 29, 2008.
PCT/US2011/060598, International Search Report and Written Opinion, mailed Mar. 22, 2013.
PCT/US2011/060598, International Preliminary Report on Patentability, dated May 14, 2013.
PCT/US2012/033047, International Search Report, mailed Jun. 28, 2012.
PCT/US2012/033047, Written Opinion by International Search Authority, mailed Jun. 28, 2012.
PCT/US2012/033047, International Preliminary Report on Patentability, dated Oct. 15, 2013.
PCT/US2012/033060, International Search Report, mailed Jul. 2, 2012.
PCT/US2012/033060, Written Opinion by International Search Authority, mailed Jul. 2, 2012.
PCT/US2012/033060, International Preliminary Report on Patentability, mailed Mar. 25, 2014.
Jackson et al., "Expression Profiling Reveals Off-target Gene Regulation by RNAi," *Nature Biotech.*, 21:635-637 (2003).
Inzé and De Veylder, "Cell Cycle Regulation in Plant Development", *Annual Review in Genetics*, 40: 77-105 (2005).
Japanese Patent Application No. 2008-524180, Office Action mailed Jan. 4, 2012.
Japanese Patent Application No. 2008-524180, English translation of the Office Action mailed Jan. 4, 2012.
Jasinski et al., "Comparative Molecular and Functional Analyses of the Tobacco Cyclin-Dependent Kinase Inhibitor NtKIS1a and its Spliced Variant NtKIS1b," *Plant Physiol.*, 130: 1871-1882 (2002).
Jasinski et al., "The CDK Inhibitor NtKIS1a is Involved in Plant Development, Endoreduplication and Restores Normal Development of Cyclin D3; 1-Overexpressing Plants", *J. Cell Sci.*, 115:973-982 (2002).
Kiyokawa et al., "Enhanced Growth of Mice Lacking the Cyclin-Dependent Kinase Inhibitor Function of p27(Kipl)", *Cell*, 85:721-732 (1996).
Koroleva, "*CycD 1*, a Putative G 1 Cyclin from *Antirrhinum majus*, Accelerates the Cell Cycle in Cultured Tobacco BY-2 Cells by Enhancing Both G1/S Entry and Progression Through S and G2 Phases", *The Plant Cell*, 16:2364-2379 (2004).
Kwon T.K. et al. "Identification of cdk2 binding sites on the $p27^{Kip1}$ cyclin-dependent kinase inhibitor", *Oncogene*, 16(6):755-762 (1988).
Leenhardt et al. "Wheat lipoxygenase activity induces greater loss of carotenoids than vitamin E during breadmaking", *J Agric Food Chem.*, 54(5):1710-1715 (2006).
Lui et al., "The *Arabidopsis* Cdc2a-Interacting Protein ICK2 is Structurally Related to ICK1 and is a Potent Inhibitor of Cyclin-Dependent Kinase Activity in vitro," *Plant J.*, 21: 379-385 (2000).
McKibbin et al., "Transcripts of Vp-1 homeologues are misspliced in modern wheat and ancestral species", *PNAS*, 99(15 ): 10203-10208 (2002).
Moloney et al., "High Efficiency Transformation of *Brassica napus* Using Agrobacterium Vectors", *Plant Cell Reports*, 8(4): 238-242 (1989).
Nakagami et al., "Phosphorylation of Retinoblastoma-Related Protein by the Cyclin D/Cyclin-Dependent Kinase Complex is Activated at the G1/S-Phase Transition in Tobacco", *Plant Cell*, 14:1847-1857 (2002).
Nakayama et al., "Mice lacking $p27^{Kip1}$ Display Increased Body Size, Multiple Organ Hyperplasia, Retinal Dysplasia, and Pituitary Tumors", *Cell*, 85:707-720 (1996).
New Zealand Patent Application No. 566040, Examination Report mailed Jan. 14, 2010.
New Zealand Patent Application No. 566040, Office Action in corresponding mailed Jun. 17, 2011.
NCBI BLAST alignment of SEQ ID No. 11 and SEQ ID No. 7 obtained from http://blast.ncbi.nlm.nih.gov/Biast.cgi on Nov. 11, 2013.
Polyak et al., "Cloning of $p27^{Kip1}$, a Cyclin-Dependent Kinase Inhibitor and a Potential Mediator of Extracellular Antimitogenic Signals", *Cell*, 78:59-66 (1994).
Russian Patent Application No. 2008107302, English translation of Office Action in mailed Mar. 19, 2010.
Russo et al., "Crystal Structure of the $p27^{Kip1}$ Cyclin-Dependent-Kinase Inhibitor Bound to the Cyclin A-Cdk2 Complex", *Nature*, 382: 325-331 (1996).
Schnittger et al., "Misexpression of the Cyclin-Dependent Kinase Inhibitor ICK1 IKRP 1 in Single-Celled Arabidopsis Trichomes Reduces Endoreduplication and Cell Size and Induces Cell Death", *Plant Cell*, 15: 303-315 (2003).
Tranquilli and Dubcovsky, "Epistatic Interaction Between Vernalization Genes Vrn-Am1 and Vrn-Am2 in Diploid Wheat", *The Journal of Heredity*, 91(4): 304-306 (2000).
Ukrainian Patent Application No. a 200802670, English translation of Office Action in mailed Jul. 11, 2011.
Van Den Heuvel and Harlow, "Distinct Roles for Cyclin-Dependent Kinases in Cell Cycle Control", *Science*, 262: 2050-2054 (1993).

(56) References Cited

OTHER PUBLICATIONS

Vietnamese Patent Application No. 1-2008-00384, English translation of Office Action mailed Jan. 18, 2010.
Vlach et al., "Phosphorylation-Dependent Degradation of the Cyclin-Dependent Kinase Inhibitor $p27^{Kip1}$", *EMBO J.*, 16:5334-44 (1997).
Wang et al., "A Plant Cyclin-Dependent Kinase Inhibitor Gene", *Nature*, 386: 451-452 (1997).
Wang et al., "Expression of the Plant Cyclin-Dependent Kinase Inhibitor ICK1 Affects Cell Division, Plant Growth and Morphology", *Plant J.*, 24: 613-623 (2000).
Wang et al., "Genome-Wide Analysis of the Cyclin Family in Arabidopsis and Comparative Phylogenetic Analysis of Plant Cyclin-Like Proteins", *Plant Physiol.*, 135: 1084-1099 (2004).
Wang et al., "ICK1, a Cyclin-Dependent Protein Kinase Inhibitor From *Arabidopsis thaliana* Interacts With Both Cdc2a and CycD3, and its Expression is Induced by Abscisic Acid", *The Plant Journal*, 15:501-510 (1998).
Yan et al., "Positional cloning of the wheat vernalization gene VRN1", *PNAS*, 100(10): 6263-6268 (2003).
Zhou et al., "Plant CDK Inhibitors: Studies of Interactions With Cell Cycle Regulators in the Yeast Two-Hybrid System and Functional Comparisons in Transgenic *Arabidopsis* Plants", *Plant Cell Rep.*, 20: 967-975 (2002).
Zhou et al., "The Plant Cyclin-Dependent Kinase Inhibitor ICK1 has Distinct Functional Domains for in vivo Kinase Inhibition, Protein Instability and Nuclear Localization", *Plant J.*, 35: 476-489 (2003).
Nakai et al., "Arabidopsis KRPs have distinct inhibitory activity toward cyclin D2-associated kinases, including plant-specific B-type cyclin-dependent kinase", FEBS Letters, 580: 336-340 (2006).
U.S. Appl. No. 13/295,809, Office Action mailed Nov. 25, 2015, 16 pages.
U.S. Appl. No. 13/295,809, Office Action mailed Apr. 23, 2015, 14 pages.
U.S. Appl. No. 13/295,809, Office Action mailed Jun. 3, 2014, 16 pages.
U.S. Appl. No. 13/295,809, Office Action mailed Nov. 21, 2013, 32 pages.
U.S. Appl. No. 14/253,004, Office Action mailed Feb. 25, 2016, 19 pages.
European Patent Application No. 11839924.5, Extended European Search Report mailed Feb. 26, 2014.
U.S. Appl. No. 13/295,809, Office Action mailed Apr. 8, 2016, 17 pages.
U.S. Appl. No. 14/111,292, Final Rejection mailed Mar. 4, 2016, 17 pages.

* cited by examiner

SEQUENCE LISTING

<160> NUMBER OF SEQ ID NOS: 87

<210> SEQ ID NO 1
<211> LENGTH: 122
<212> TYPE: PRT
<213> ORGANISM: Triticum aestivum

<400> SEQUENCE: 1

```
Met Gly Lys Tyr Met Arg Lys Cys Arg Ala Glu Asp Gly Ala Val Gly
1               5                   10                  15

Gly Val Glu Val Thr Gln Ala Val Gly Val Arg Thr Arg Ser Arg Ala
            20                  25                  30

Ala Ala Ala Asn Val Val Val Ser Lys Arg Arg Arg Pro Leu Pro Pro
        35                  40                  45

Gly Ser Pro Ser Ala Ser Ser Ser Leu Ala Arg Ala Gln Gly Gly Ser
    50                  55                  60

Cys Tyr Leu Lys Leu Arg Ser Arg Met Leu Phe Met Ala Pro Pro Ala
65                  70                  75                  80

Pro Ala Ser Gly Ala Ala Ala Gly His Gly Pro Ala Pro Pro Leu Pro
                85                  90                  95

Ala Gly Leu Ser Arg Cys Ser Ser Thr Ala Ser Ser Val Asp Ala Ser
            100                 105                 110

Ala Ala Ala Gln Asp Arg Ser Leu Pro Ser
        115                 120
```

<210> SEQ ID NO 2
<211> LENGTH: 244
<212> TYPE: PRT
<213> ORGANISM: Triticum aestivum

<400> SEQUENCE: 2

```
Leu Gly Val Arg Thr Arg Ser Arg Ala Gly Ala Arg Asp Ala Lys Met
1               5                   10                  15

Arg Lys Gln Gln Gln Ala Thr Thr Ser Thr Ala Ala Arg Ala Val Glu
            20                  25                  30
```

```
Asp Ala Leu Leu Gly Arg Asp Gly Gly Asp Ala Ala Ala Gly Cys Tyr
        35                  40                  45

Leu His Leu Arg Ser Arg Arg Leu Phe Met Pro Ala Ala Ala Val Val
    50                  55                  60

Asp Arg Gly Gly Gly Gly Gly Leu Cys Glu Glu Ala Ser Thr Ala Gly
65                  70                  75                  80

Leu Pro Asp Ser Gly Pro Ser Val Glu Ala Ala Val Gly Ala Gly Val
                85                  90                  95

Ser Arg Cys Ser Ser Thr Val Ser Thr Ala Val Asp Val Ala Ala Arg
            100                 105                 110

Glu Arg Ser Gly Asp Glu Ala Glu Ala Cys Glu Ser Arg Asp Val Glu
        115                 120                 125

Ser Ser Val Ser Asp Ser Glu Cys Gly Gly Arg Asp Arg Arg Glu Thr
    130                 135                 140

Thr Pro Ser Ser Arg Ser Pro Val Asp Leu Ser Asp Leu Glu Ser Ser
145                 150                 155                 160

Gln Ala Ala Asp Glu Gln Lys His Lys Arg Arg Arg Cys Pro Ala Thr
                165                 170                 175

Thr Thr Thr Thr Ala Ala Pro Leu His Tyr Asp Leu Glu Ala Arg Ala
            180                 185                 190

Arg Ala Arg Met Pro Pro Ala Ala Glu Ile Asp Glu Phe Phe Ala Ala
        195                 200                 205

Ala Glu Lys Ala Gln Ala Glu Arg Phe Ala Ala Lys Tyr Asn Phe Asp
    210                 215                 220

Val Ala Arg Gly Val Pro Leu Asn Ala Gly Arg Phe Glu Trp Thr Pro
225                 230                 235                 240

Val Ala Thr Val


<210> SEQ ID NO 3
<211> LENGTH: 190
<212> TYPE: PRT
<213> ORGANISM: Triticum aestivum

<400> SEQUENCE: 3

Met Gly Lys Tyr Met Arg Lys Pro Lys Val Ser Gly Glu Val Ala Val
1               5                   10                  15

Met Glu Val Ala Ala Ala Pro Leu Gly Val Arg Thr Arg Ala Arg Ala
            20                  25                  30

Leu Ala Met Gln Arg Gln Pro Gln Gly Ala Ala Val Ala Lys Asp Gln
        35                  40                  45

Gly Glu Tyr Leu Glu Leu Arg Ser Arg Lys Leu Glu Lys Leu Pro Pro
    50                  55                  60

Pro Pro Pro Ala Ala Arg Arg Arg Ala Ala Ala Ala Glu Arg Val Glu
65                  70                  75                  80

Ala Glu Ala Glu Ala Asp Glu Val Ser Phe Gly Glu Asn Val Leu Glu
                85                  90                  95

Ser Glu Ala Met Gly Arg Gly Thr Arg Glu Thr Thr Pro Cys Ser Leu
            100                 105                 110

Ile Arg Asp Ser Gly Thr Ile Ser Thr Pro Gly Ser Thr Thr Arg Pro
        115                 120                 125

Ser His Ser Asn Ser His Arg Arg Val Gln Ala Pro Ala Arg His Ile
    130                 135                 140

Ile Pro Cys Ser Ala Glu Met Asn Glu Phe Phe Ser Ala Ala Glu Gln
145                 150                 155                 160
```

Pro Gln Gln Gln Ala Phe Ile Asp Lys Tyr Asn Phe Asp Pro Val Asn
165 170 175

Asp Cys Pro Leu Pro Gly Arg Tyr Glu Trp Val Lys Leu Asp
180 185 190

<210> SEQ ID NO 4
<211> LENGTH: 190
<212> TYPE: PRT
<213> ORGANISM: Triticum urartu

<400> SEQUENCE: 4

Met Gly Lys Tyr Met Arg Lys Pro Lys Val Ser Gly Glu Val Ala Val
1 5 10 15

Met Glu Val Ala Ala Ala Pro Leu Gly Val Arg Thr Arg Ala Arg Ala
20 25 30

Leu Ala Met Gln Arg Gln Pro Gln Gly Ala Pro Gly Ala Lys Asp Gln
35 40 45

Gly Glu Tyr Leu Glu Leu Arg Ser Arg Lys Leu Glu Lys Leu Pro Pro
50 55 60

Pro Pro Pro Pro Ala Arg Arg Arg Ala Ala Ala Ala Glu Arg Val Glu
65 70 75 80

Ala Glu Ala Glu Ala Asp Lys Val Ser Phe Gly Glu Asn Val Leu Glu
85 90 95

Pro Glu Ala Met Gly Arg Gly Thr Arg Glu Thr Thr Pro Cys Ser Leu
100 105 110

Ile Arg Asp Ser Gly Met Ile Ser Thr Pro Gly Ser Thr Thr Arg Pro
115 120 125

Ser His Ser Asn Ser His Arg Arg Val Gln Ala Pro Ala Arg His Ile
130 135 140

Ile Pro Ser Ser Ala Glu Met Asn Glu Phe Phe Ser Ala Ala Glu Gln
145 150 155 160

Pro Gln Gln Gln Ala Phe Ile Asp Lys Tyr Asn Phe Asp Pro Val Asn
165 170 175

Asp Cys Pro Leu Pro Gly Arg Tyr Glu Trp Val Lys Leu Asp
180 185 190

<210> SEQ ID NO 5
<211> LENGTH: 141
<212> TYPE: PRT
<213> ORGANISM: Triticum aestivum

<400> SEQUENCE: 5

Gly Thr Arg Lys Glu Lys Gly Asp Ala Pro Gln Pro Ala Ala Arg Arg
1 5 10 15

Ala Ala Ala Ala Gly Gly Arg Gly Met Glu Ser Phe Ala Ala Glu Gly
20 25 30

Phe Glu Ala Asp Leu Glu Val Ser Phe Gly Asp Asn Val Leu Asp Trp
35 40 45

Asp Ala Thr Asp Arg Gly Ala Arg Glu Thr Thr Pro Cys Ser Leu Ile
50 55 60

Tyr Ser Ser Glu Thr Met Ser Thr Pro Gly Ser Ala Thr Gly Ala Arg
65 70 75 80

Asn His Ser Arg Arg Arg Ala Gln Thr Pro Val Cys Arg Tyr Val Pro
85 90 95

Ser Ser Leu Glu Met Asp Glu Phe Phe Ala Ala Ala Glu Gln Gln Gln
100 105 110

-continued

```
His Gln Thr Phe Arg Glu Lys Tyr Asn Phe Cys Pro Ala Ser Glu Arg
        115                 120                 125

Pro Leu Pro Gly Arg Tyr Glu Trp Thr Val Leu Asp Cys
    130                 135                 140


<210> SEQ ID NO 6
<211> LENGTH: 20
<212> TYPE: DNA
<213> ORGANISM: artificial
<220> FEATURE:
<223> OTHER INFORMATION: primer

<400> SEQUENCE: 6

gtctgtagaa cggcgttacg                                                  20


<210> SEQ ID NO 7
<211> LENGTH: 24
<212> TYPE: DNA
<213> ORGANISM: artificial
<220> FEATURE:
<223> OTHER INFORMATION: primer

<400> SEQUENCE: 7

ccccagctct acagtgagta actt                                              24


<210> SEQ ID NO 8
<211> LENGTH: 21
<212> TYPE: DNA
<213> ORGANISM: artificial
<220> FEATURE:
<223> OTHER INFORMATION: primer

<400> SEQUENCE: 8

ggagagaatc caaagagcaa c                                                 21


<210> SEQ ID NO 9
<211> LENGTH: 20
<212> TYPE: DNA
<213> ORGANISM: artificial
<220> FEATURE:
<223> OTHER INFORMATION: primer

<400> SEQUENCE: 9

ccagctctac agtgagtaac                                                   20


<210> SEQ ID NO 10
<211> LENGTH: 22
<212> TYPE: DNA
<213> ORGANISM: artificial
<220> FEATURE:
<223> OTHER INFORMATION: primer

<400> SEQUENCE: 10

cgtgttatat gtgtacgcac ac                                                22


<210> SEQ ID NO 11
<211> LENGTH: 24
<212> TYPE: DNA
<213> ORGANISM: artificial
<220> FEATURE:
<223> OTHER INFORMATION: primer

<400> SEQUENCE: 11

ggctataatg cttctttctg gagc                                              24
```

<210> SEQ ID NO 12
<211> LENGTH: 19
<212> TYPE: DNA
<213> ORGANISM: artificial
<220> FEATURE:
<223> OTHER INFORMATION: primer

<400> SEQUENCE: 12
caaacggcca aagcgacgg 19

<210> SEQ ID NO 13
<211> LENGTH: 21
<212> TYPE: DNA
<213> ORGANISM: artificial
<220> FEATURE:
<223> OTHER INFORMATION: primer

<400> SEQUENCE: 13
ctagtgttgc atagttagct c 21

<210> SEQ ID NO 14
<211> LENGTH: 19
<212> TYPE: DNA
<213> ORGANISM: artificial
<220> FEATURE:
<223> OTHER INFORMATION: primer

<400> SEQUENCE: 14
caaacggcca aagcgacgg 19

<210> SEQ ID NO 15
<211> LENGTH: 20
<212> TYPE: DNA
<213> ORGANISM: artificial
<220> FEATURE:
<223> OTHER INFORMATION: primer

<400> SEQUENCE: 15
tctcgcctcc gagtctaagt 20

<210> SEQ ID NO 16
<211> LENGTH: 19
<212> TYPE: DNA
<213> ORGANISM: artificial
<220> FEATURE:
<223> OTHER INFORMATION: primer

<400> SEQUENCE: 16
caaacggcca aagcgacgg 19

<210> SEQ ID NO 17
<211> LENGTH: 21
<212> TYPE: DNA
<213> ORGANISM: artificial
<220> FEATURE:
<223> OTHER INFORMATION: primer

<400> SEQUENCE: 17
cagatttgaa caaggtggat c 21

<210> SEQ ID NO 18
<211> LENGTH: 28
<212> TYPE: DNA
<213> ORGANISM: artificial
<220> FEATURE:
<223> OTHER INFORMATION: primer -continued

<400> SEQUENCE: 18
tacccgcgcc tcgcttaaat ccgccaaa 28

<210> SEQ ID NO 19
<211> LENGTH: 30
<212> TYPE: DNA
<213> ORGANISM: artificial
<220> FEATURE:
<223> OTHER INFORMATION: primer

<400> SEQUENCE: 19
gtcaactcgt gaaagaagag ttgggacaga 30

<210> SEQ ID NO 20
<211> LENGTH: 29
<212> TYPE: DNA
<213> ORGANISM: artificial
<220> FEATURE:
<223> OTHER INFORMATION: primer

<400> SEQUENCE: 20
ccttaggcaa gttcggtaag aaatgtgta 29

<210> SEQ ID NO 21
<211> LENGTH: 31
<212> TYPE: DNA
<213> ORGANISM: artificial
<220> FEATURE:
<223> OTHER INFORMATION: primer

<400> SEQUENCE: 21
gtggtcatta cagaatgagt tgctaaccgt c 31

<210> SEQ ID NO 22
<211> LENGTH: 28
<212> TYPE: DNA
<213> ORGANISM: artificial
<220> FEATURE:
<223> OTHER INFORMATION: primer

<400> SEQUENCE: 22
ttacccgcgc ctcgcttaaa tccgcaag 28

<210> SEQ ID NO 23
<211> LENGTH: 30
<212> TYPE: DNA
<213> ORGANISM: artificial
<220> FEATURE:
<223> OTHER INFORMATION: primer

<400> SEQUENCE: 23
gctcaaacag cgaaagaaga gttagacgga 30

<210> SEQ ID NO 24
<211> LENGTH: 30
<212> TYPE: DNA
<213> ORGANISM: artificial
<220> FEATURE:
<223> OTHER INFORMATION: primer

<400> SEQUENCE: 24
ctggcctact catgtgagac tgagagatta 30

<210> SEQ ID NO 25

<211> LENGTH: 31
<212> TYPE: DNA
<213> ORGANISM: artificial
<220> FEATURE:
<223> OTHER INFORMATION: primer

<400> SEQUENCE: 25
gtggtcatta cagaatgagc tgctaaccgt t 31

<210> SEQ ID NO 26
<211> LENGTH: 28
<212> TYPE: DNA
<213> ORGANISM: artificial
<220> FEATURE:
<223> OTHER INFORMATION: primer

<400> SEQUENCE: 26
tacccgcccc tcgcttaaat ccgccaaa 28

<210> SEQ ID NO 27
<211> LENGTH: 31
<212> TYPE: DNA
<213> ORGANISM: artificial
<220> FEATURE:
<223> OTHER INFORMATION: primer

<400> SEQUENCE: 27
actcaaatag cgaaagaaga gttagccagg a 31

<210> SEQ ID NO 28
<211> LENGTH: 29
<212> TYPE: DNA
<213> ORGANISM: artificial
<220> FEATURE:
<223> OTHER INFORMATION: primer

<400> SEQUENCE: 28
tggcctactc atgtgacact gagagattg 29

<210> SEQ ID NO 29
<211> LENGTH: 31
<212> TYPE: DNA
<213> ORGANISM: artificial
<220> FEATURE:
<223> OTHER INFORMATION: primer

<400> SEQUENCE: 29
gtggtcatta cagaatgagc tgctaaccgt t 31

<210> SEQ ID NO 30
<211> LENGTH: 20
<212> TYPE: DNA
<213> ORGANISM: artificial
<220> FEATURE:
<223> OTHER INFORMATION: primer

<400> SEQUENCE: 30
gtaagcacag gaagcagagc 20

<210> SEQ ID NO 31
<211> LENGTH: 20
<212> TYPE: DNA
<213> ORGANISM: artificial
<220> FEATURE:
<223> OTHER INFORMATION: primer

<400> SEQUENCE: 31

```
ctcagtcgta ttcgtatcgg                                              20


<210> SEQ ID NO 32
<211> LENGTH: 21
<212> TYPE: DNA
<213> ORGANISM: artificial
<220> FEATURE:
<223> OTHER INFORMATION: primer

<400> SEQUENCE: 32

cacacctcac attgtgtgat g                                            21


<210> SEQ ID NO 33
<211> LENGTH: 20
<212> TYPE: DNA
<213> ORGANISM: artificial
<220> FEATURE:
<223> OTHER INFORMATION: primer

<400> SEQUENCE: 33

acagagatca atggaggagc                                              20


<210> SEQ ID NO 34
<211> LENGTH: 20
<212> TYPE: DNA
<213> ORGANISM: artificial
<220> FEATURE:
<223> OTHER INFORMATION: primer

<400> SEQUENCE: 34

tgcgcctcac attgtctagc                                              20


<210> SEQ ID NO 35
<211> LENGTH: 20
<212> TYPE: DNA
<213> ORGANISM: artificial
<220> FEATURE:
<223> OTHER INFORMATION: primer

<400> SEQUENCE: 35

acagagatca atggaggagc                                              20


<210> SEQ ID NO 36
<211> LENGTH: 21
<212> TYPE: DNA
<213> ORGANISM: artificial
<220> FEATURE:
<223> OTHER INFORMATION: primer

<400> SEQUENCE: 36

atgctagaac atgagctgtc g                                            21


<210> SEQ ID NO 37
<211> LENGTH: 20
<212> TYPE: DNA
<213> ORGANISM: artificial
<220> FEATURE:
<223> OTHER INFORMATION: primer

<400> SEQUENCE: 37

gctgatggtg gtggtcattc                                              20


<210> SEQ ID NO 38
<211> LENGTH: 467
<212> TYPE: DNA
```

<213> ORGANISM: Triticum aestivum

<400> SEQUENCE: 38

```
agcagcccag cggcatcata cccctccctc ccacccaccg gcgccgcgct gcagacgcaa      60

acggccaaag gcgagcggcg tggggcggag cgcggggcaa tggggaagta catgcgcaag     120

tgcagggcgg aggacggcgc ggtgggcggc gtggaggtca cgcaggccgt cggcgtccgc     180

acccggtccc gcgcggccgc ggccaacgtc gtcgtctcca agaggaggcg cccgctgccg     240

cccggctcgc cgtcggcctc gtcgtccctc gctcgcgccc agggcgggag ctgctacctg     300

aagctgcgga gccgcatgct gttcatggcc ccgccggcgc ccgcatcggg ggctgccgcc     360

gggcacgggc cggcgccgcc gctcccggcc ggcctgtcgc gctgctccag cacggcgtcg     420

tccgtggacg cgtcggccgc ggcgcaggac aggagcctgc cctcgtg                   467
```

<210> SEQ ID NO 39
<211> LENGTH: 262
<212> TYPE: PRT
<213> ORGANISM: Oryza sativa

<400> SEQUENCE: 39

```
Met Gly Lys Tyr Met Arg Lys Phe Arg Gly Ala Thr Gly Glu Glu Leu
1               5                   10                  15

Ala Ala Met Glu Val Thr Gln Val Val Gly Val Arg Thr Arg Ser Arg
            20                  25                  30

Ser Ala Ala Ala Ala Gly Ala Thr Thr Thr Lys Val Lys Ala Ala Ser
        35                  40                  45

Ala Ala Ser Thr Arg Arg Arg Lys Ala Leu Leu Pro Thr Ala Val Val
    50                  55                  60

Gly Thr Thr Arg Arg Asp Gly Gly Ser Cys Tyr Leu Gln Leu Arg Ser
65                  70                  75                  80

Arg Met Leu Phe Met Ala Pro Pro Arg Pro Ala Pro Ala Ala Arg Ala
                85                  90                  95

Pro Val Val Ala Glu Ala Ala Gly Ser Gly Asn Gly Ala Ala Ala His
            100                 105                 110

Ala Ala Ala Gly Leu Ser Arg Cys Ser Ser Thr Ala Ser Ser Val Asp
        115                 120                 125

Ala Ala Ala Gln Asp Arg Ser Leu Ala Cys Arg Ser Asp Val Ala Glu
    130                 135                 140

Ala Gly Ser Glu His Val Pro Glu Gly Ser Ala Ser Asp Ser Ala Ser
145                 150                 155                 160

Gly Arg Asp Arg Glu Arg Arg Glu Thr Thr Pro Ser Ser Phe Leu Pro
                165                 170                 175

Gly Glu Val Ser Asp Leu Glu Ser Asp Leu Ala Gly Gly Gln Lys Arg
            180                 185                 190

Ser Arg Pro Leu Pro Ser Ala Ala Thr Ala Ser Ala Gln Gln Ala Thr
        195                 200                 205

Arg Pro Lys Ile Pro Pro Ala Ala Glu Ile Glu Ala Phe Phe Ala Ala
    210                 215                 220

Ala Glu Glu Ala Glu Ala Lys Arg Phe Ala Ala Lys Tyr Asn Phe Asp
225                 230                 235                 240

Val Val Arg Gly Val Pro Leu Asp Ala Gly Arg Phe Glu Trp Thr Pro
                245                 250                 255

Val Val Ser Ser Arg Ser
            260
```

<210> SEQ ID NO 40
<211> LENGTH: 1410
<212> TYPE: DNA
<213> ORGANISM: Triticum aestivum

<400> SEQUENCE: 40
cctgggcgtc ggatcgggac ccgatccccc ggctcccccc ttggcgtgtt atatgcgtac 60
gcacccacgc gcacggggcg cactccggac gggggagaga atccaaagag cagcccagcg 120
gcatcatacc cctccctccc acccaccggc gccgcgctgc agacgcaaac ggccaaaggc 180
gagcggcgtg gggcggagcg cggggcgatg gggaagtaca tgcgcaagtg cagggcggag 240
gacggcgcgg tgggcggcgt ggaggtcacg caggccgtcg gcgtccgcac ccggtcccgc 300
gcggccgcgg ccaacgtcgt cgtctccaag aggaggcgcc cgctgccgcc cggctcgccg 360
tcggcctcgt cgtccctcgc tcgcgcccag ggcgggagct gctacctgaa gctgcggagc 420
cgcatgctgt tcatggcccc gccggcgccc gcatcggggg ctgccgccgg gcacgggccg 480
gcgccgccgc tcccggccgg cctgtcgcgc tgctccagca cggcgtcgtc cgtggacgcg 540
tcggccgcgg cgcaggacag gagcctgctc tcgtgcggct ccgacgccgc tgccaacaac 600
aaggtgaggg aattgggtcc aaaccctaga attcggatac gattcgagat ctcctttttg 660
accgaaaccc gtgtctttct ccgctctgca ggcaggcgcc ccggagggct cggcgagcaa 720
caacgcggag agcggcggca accgcgagag gtgcgagatc gaattccgtc ttctttccag 780
cgaattcttg tgaattatgc ctcctgccgt gctcctgacc ccgtcccgct cgccgttttt 840
gaaaattcag gcgagagacg acgccgtcca gccatttccc cggcgacctg agcgacctgg 900
agtcggatct ggcggggcag aacagcggcc ggtcgtcgct gccgcaaacg ccgaccgccc 960
aggcccagcc cgccgcgagg tcgagggtcc cgccggcggc cgagatcgag gagttcttcg 1020
cggccgccga ggaggccgag gccaggcggt tcgcttgcaa gtaagtgctt ttagcagcag 1080
cggaaactct aattctccac ttcgtcgccg gagttctaac gtgagagctt tctctcgccg 1140
tggccaggta caacttcgac gtggcccgcg gcgtgccgct cggctccggc cggtacgagt 1200
ggaccccggc ggtgagcagc agctaggcag gcgacgaaag cgggcgtgca aagggggggag 1260 agaagccgta gctagaaagt tactcactgt agagctgggg cgccggccgg ccggccggcc 1320
gtgtagaaag gccaagggaa aaagatgctc cggaaagaag aaaagaagca ttatagccta 1380
accaaccaac caaccaccga tcatcaacaa 1410

<210> SEQ ID NO 41
<211> LENGTH: 744
<212> TYPE: DNA
<213> ORGANISM: Triticum aestivum

<400> SEQUENCE: 41
atggggaagt acatgcgcaa gtgcagggcg gaggacggcg cggtgggcgg cgtggaggtc 60
acgcaggccg tcggcgtccg cacccggtcc cgcgcggccg cggccaacgt cgtcgtctcc 120
aagaggaggc gcccgctgcc gcccggctcg ccgtcggcct cgtcgtccct cgctcgcgcc 180
cagggcggga gctgctacct gaagctgcgg agccgcatgc tgttcatggc cccgccggcg 240
cccgcatcgg gggctgccgc cgggcacggg ccggcgccgc cgctcccggc cggcctgtcg 300
cgctgctcca gcacggcgtc gtccgtggac gcgtcggccg cggcgcagga caggagcctg 360
ctctcgtgcg gctccgacgc cgctgccaac aacaaggcag gcgccccgga gggctcggcg 420
agcaacaacg cggagagcgg cggcaaccgc gagaggcgag agacgacgcc gtccagccat 480

```
ttccccggcg acctgagcga cctggagtcg gatctggcgg ggcagaacag cggccggtcg    540

tcgctgccgc aaacgccgac cgcccaggcc cagcccgccg cgaggtcgag ggtcccgccg    600

gcggccgaga tcgaggagtt cttcgcggcc gccgaggagg ccgaggccag gcggttcgct    660

tgcaagtaca acttcgacgt ggcccgcggc gtgccgctcg actccggccg gtacgagtgg    720

accccggcgg tgagcagcag ctag                                          744
```

<210> SEQ ID NO 42
<211> LENGTH: 247
<212> TYPE: PRT
<213> ORGANISM: Triticum aestivum

<400> SEQUENCE: 42

```
Met Gly Lys Tyr Met Arg Lys Cys Arg Ala Glu Asp Gly Ala Val Gly
1               5                   10                  15

Gly Val Glu Val Thr Gln Ala Val Gly Val Arg Thr Arg Ser Arg Ala
            20                  25                  30

Ala Ala Ala Asn Val Val Val Ser Lys Arg Arg Arg Pro Leu Pro Pro
        35                  40                  45

Gly Ser Pro Ser Ala Ser Ser Ser Leu Ala Arg Ala Gln Gly Gly Ser
    50                  55                  60

Cys Tyr Leu Lys Leu Arg Ser Arg Met Leu Phe Met Ala Pro Pro Ala
65                  70                  75                  80

Pro Ala Ser Gly Ala Ala Ala Gly His Gly Pro Ala Pro Pro Leu Pro
                85                  90                  95

Ala Gly Leu Ser Arg Cys Ser Ser Thr Ala Ser Ser Val Asp Ala Ser
            100                 105                 110

Ala Ala Ala Gln Asp Arg Ser Leu Leu Ser Cys Gly Ser Asp Ala Ala
        115                 120                 125

Ala Asn Asn Lys Ala Gly Ala Pro Glu Gly Ser Ala Ser Asn Asn Ala
    130                 135                 140

Glu Ser Gly Gly Asn Arg Glu Arg Arg Glu Thr Thr Pro Ser Ser His
145                 150                 155                 160

Phe Pro Gly Asp Leu Ser Asp Leu Glu Ser Asp Leu Ala Gly Gln Asn
                165                 170                 175

Ser Gly Arg Ser Ser Leu Pro Gln Thr Pro Thr Ala Gln Ala Gln Pro
            180                 185                 190

Ala Ala Arg Ser Arg Val Pro Pro Ala Ala Glu Ile Glu Glu Phe Phe
        195                 200                 205

Ala Ala Ala Glu Glu Ala Glu Ala Arg Arg Phe Ala Cys Lys Tyr Asn
    210                 215                 220

Phe Asp Val Ala Arg Gly Val Pro Leu Gly Ser Gly Arg Tyr Glu Trp
225                 230                 235                 240

Thr Pro Ala Val Ser Ser Ser
                245
```

<210> SEQ ID NO 43
<211> LENGTH: 1095
<212> TYPE: DNA
<213> ORGANISM: Triticum aestivum

<400> SEQUENCE: 43

```
cgcgctgcgc actgcagacg gaaacggcca aaggagggca ggcaggagcg cgcggcgtgg     60

ggcgatgggg aagtacatgc gcaagtgcag ggcggaggac ggcgtgggcg gcgtggaggt    120
```

```
cacgcaggcc gtcggcgtcc ggacccggtc gcgggcggcc gcggccaacg tcgtcgtttc    180

caagaggagg cggccgctgc cgccaagctc gcccctcggc ggcgccgccg ctcgcgccca    240

gagcgggagc tgctacctga agctgcggag ccgcatgctg ttcatggccc cgccggcgcc    300

tgcatcggct gctggcccag ggcacaggcc ggcgccgccg ctcccggcgg gcctctcgcg    360

ctgctccagc acggcgtcgt ccgtggacgc gtcggccgcg ggacaggata ggagcctgcc    420

gtcgtgcggc tccgacgccg ctgcaaacag caaggtgagg gaattggggt ccaaacccta    480

gagttcggat acgattcgag atctcctttt tttgctgaaa atcgtggctt tctccgctct    540

acaggcaggc gctccggagg gctcagcaag caacaacgcg gagagcggcg gcaaccgcga    600

gaggtgcgag atcgaattcc ctcctgtctc cggccaattc ttgtgaatta tgcctcctga    660

cgtgctcctg accccgtccc gctcgtcgct tttgaaaatt caggcgagag acgacgccgt    720

ccagccattt ccccggcgac ctgagcgacc tggagtcgga tctggcgggc cagaacagcg    780

gccggtcgtc gctgccgcaa acgccgaccg cccaggtcca gccggccgcg aggtcgagga    840

tcccgccggc ggccgagatc gaggagttct tcgcggccgc cgaggaggcc gaggccaggc    900

gcttcgcttg caagtaagta ctttagcagc agcggaaatt tccttatctt gcggccgccg    960

tcgccgtcgc cggaattcta acgtgcgagc tctctgtgcc aggtacaact tcgacgtggc   1020

ccgcggcgtg cctctcgact ccggccggta cgagtggacc ccggcggtga gcagcaacta   1080

gccagccgag aaagc                                                    1095
```

<210> SEQ ID NO 44
<211> LENGTH: 738
<212> TYPE: DNA
<213> ORGANISM: Triticum aestivum

<400> SEQUENCE: 44

```
atggggaagt acatgcgcaa gtgcagggcg gaggacggcg tgggcggcgt ggaggtcacg     60

caggccgtcg gcgtccggac ccggtcgcgg gcggccgcgg ccaacgtcgt cgtttccaag    120

aggaggcggc cgctgccgcc aagctcgccc ctcggcggcg ccgccgctcg cgcccagagc    180

gggagctgct acctgaagct gcggagccgc atgctgttca tggccccgcc ggcgcctgca    240

tcggctgctg gcccagggca caggccggcg ccgccgctcc cggcgggcct ctcgcgctgc    300

tccagcacgg cgtcgtccgt ggacgcgtcg gccgcgggac aggataggag cctgccgtcg    360

tgcggctccg acgccgctgc aaacagcaag gcaggcgctc cggagggctc agcaagcaac    420

aacgcggaga gcggcggcaa ccgcgagagg cgagagacga cgccgtccag ccatttcccc    480

ggcgacctga gcgacctgga gtcggatctg gcgggccaga acagcggccg gtcgtcgctg    540

ccgcaaacgc cgaccgccca ggtccagccg gccgcgaggt cgaggatccc gccggcggcc    600

gagatcgagg agttcttcgc ggccgccgag gaggccgagg ccaggcgctt cgcttgcaag    660

tacaacttcg acgtggcccg cggcgtgcct ctcgactccg gccggtacga gtggaccccg    720

gcggtgagca gcaactag                                                  738
```

<210> SEQ ID NO 45
<211> LENGTH: 245
<212> TYPE: PRT
<213> ORGANISM: Triticum aestivum

<400> SEQUENCE: 45

```
Met Gly Lys Tyr Met Arg Lys Cys Arg Ala Glu Asp Gly Val Gly Gly
1               5                   10                  15
```

```
Val Glu Val Thr Gln Ala Val Gly Val Arg Thr Arg Ser Arg Ala Ala
            20                  25                  30

Ala Ala Asn Val Val Val Ser Lys Arg Arg Arg Pro Leu Pro Pro Ser
        35                  40                  45

Ser Pro Leu Gly Gly Ala Ala Ala Arg Ala Gln Ser Gly Ser Cys Tyr
    50                  55                  60

Leu Lys Leu Arg Ser Arg Met Leu Phe Met Ala Pro Pro Ala Pro Ala
65                  70                  75                  80

Ser Ala Ala Gly Pro Gly His Arg Pro Ala Pro Pro Leu Pro Ala Gly
                85                  90                  95

Leu Ser Arg Cys Ser Ser Thr Ala Ser Ser Val Asp Ala Ser Ala Ala
            100                 105                 110

Gly Gln Asp Arg Ser Leu Pro Ser Cys Gly Ser Asp Ala Ala Ala Asn
        115                 120                 125

Ser Lys Ala Gly Ala Pro Glu Gly Ser Ala Ser Asn Asn Ala Glu Ser
    130                 135                 140

Gly Gly Asn Arg Glu Arg Arg Glu Thr Thr Pro Ser Ser His Phe Pro
145                 150                 155                 160

Gly Asp Leu Ser Asp Leu Glu Ser Asp Leu Ala Gly Gln Asn Ser Gly
                165                 170                 175

Arg Ser Ser Leu Pro Gln Thr Pro Thr Ala Gln Val Gln Pro Ala Ala
            180                 185                 190

Arg Ser Arg Ile Pro Pro Ala Ala Glu Ile Glu Glu Phe Phe Ala Ala
        195                 200                 205

Ala Glu Glu Ala Glu Ala Arg Arg Phe Ala Cys Lys Tyr Asn Phe Asp
    210                 215                 220

Val Ala Arg Gly Val Pro Leu Asp Ser Gly Arg Tyr Glu Trp Thr Pro
225                 230                 235                 240

Ala Val Ser Ser Asn
                245


<210> SEQ ID NO 46
<211> LENGTH: 1304
<212> TYPE: DNA
<213> ORGANISM: Triticum aestivum

<400> SEQUENCE: 46

atccaaaggg cgagccgaac aacccagcgg catcatatcc ctcccaccgg cgccgcgctg      60

cgcactgcag acggaaacgg ccaaaggaga gcggcgtggg gcggagcggg gggcgatggg     120

gaagtacatg cgcaagtgca gggcggagga cgtcgcggtg ggcggcgtgg aggtcacgca     180

ggccgtcggc gtccggacgc ggtcccgggc ggccgcggcc aacgtcgtcg tctccaagag     240

gaggcgcccg ctgccgcccg cctcgccgtc ggcctcgtcg gccctcgctc gcgcccaggg     300

cgggagctgc tacctgaagc tgcggagccg catgctgttc atggccccgc cggcgcctgc     360

gtcggcgtcg gccgctgccg ccgggcacgg ggcgccgccg ccgctcccgg ccggcctctc     420

gcgctgctcc agcacggcct cgtccgtgga cgcgtcggcc gcggcgcagg acaggagcct     480

gccgtcgtgc ggctccgacg ccgctgccaa caaggtgagg gaattgggtc caaaccctag     540

aattcggata caattcgaga tctccttttt gctgaaaacc gtggctttct ccgccctaca     600

ggcaggcgct ccggagggct cggcgagcaa caacgcggag agcggcggca accgcgagag     660

gtgcgagatc gaattccctc ctgtctccgg ccaattcttc cgaattatgc atcctaaccc     720

cgtcccgctc gctgcttttc aaaattcagg cgagagacga cgccgtccag ccatttcccc     780
```

ggcgacctga gcgacctgga gtcggatctg gcgggcaaga acagcggccg gtcgtcgctg 840
ccgcaaacgc tggccgccca ggctcagccc gccgcgaggt cgagggtccc gccggcggcc 900
gagatcgagg agttcttcgc ggccgccgag gaggccgagg ccaggcgctt cgcttgcaag 960
taagtactcc tactttagca gcagcggaaa tttccttatc ttgcggccgc cgtcgccgtc 1020
gccggaattc taacgtggga gctctctacg ccaggtacaa cttcgacgtg gcccgcggcg 1080
tgcccctcga ctccggccgg tacgagtgga ccccggcggt gagcagcagc taggcaggcg 1140
acgaaagcgg gcgtgcaaag gggggagaga agccgtagct agaaagttac tcactgtaga 1200
gctggggcgc cggccggccg gccggccgtg tagaaaggcg aagggaaaaa gatgctccgg 1260
aaagaagcat tatagcctaa ccaaccaacc taccaccgat catc 1304

<210> SEQ ID NO 47
<211> LENGTH: 747
<212> TYPE: DNA
<213> ORGANISM: Triticum aestivum

<400> SEQUENCE: 47
atggggaagt acatgcgcaa gtgcagggcg gaggacgtcg cggtgggcgg cgtggaggtc 60
acgcaggccg tcggcgtccg gacgcggtcc cgggcggccg cggccaacgt cgtcgtctcc 120
aagaggaggc gcccgctgcc gcccgcctcg ccgtcggcct cgtcggccct cgctcgcgcc 180
cagggcggga gctgctacct gaagctgcgg agccgcatgc tgttcatggc cccgccggcg 240
cctgcgtcgg cgtcggccgc tgccgccggg cacggggcgc cgccgccgct cccggccggc 300
ctctcgcgct gctccagcac ggcctcgtcc gtggacgcgt cggccgcggc gcaggacagg 360
agcctgccgt cgtgcggctc cgacgccgct gccaacaagg caggcgctcc ggagggctcg 420
gcgagcaaca acgcggagag cggcggcaac cgcgagaggc gagagacgac gccgtccagc 480
catttccccg gcgacctgag cgacctggag tcggatctgg cgggcaagaa cagcggccgg 540
tcgtcgctgc cgcaaacgct ggccgcccag gctcagcccg ccgcgaggtc gagggtcccg 600
ccggcggccg agatcgagga gttcttcgcg gccgccgagg aggccgaggc caggcgcttc 660
gcttgcaagt acaacttcga cgtggcccgc ggcgtgcccc tcgactccgg ccggtacgag 720
tggaccccgg cggtgagcag cagctag 747

<210> SEQ ID NO 48
<211> LENGTH: 248
<212> TYPE: PRT
<213> ORGANISM: Triticum aestivum

<400> SEQUENCE: 48

Met Gly Lys Tyr Met Arg Lys Cys Arg Ala Glu Asp Val Ala Val Gly
1 5 10 15

Gly Val Glu Val Thr Gln Ala Val Gly Val Arg Thr Arg Ser Arg Ala
20 25 30

Ala Ala Ala Asn Val Val Val Ser Lys Arg Arg Arg Pro Leu Pro Pro
35 40 45

Ala Ser Pro Ser Ala Ser Ser Ala Leu Ala Arg Ala Gln Gly Gly Ser
50 55 60

Cys Tyr Leu Lys Leu Arg Ser Arg Met Leu Phe Met Ala Pro Pro Ala
65 70 75 80

Pro Ala Ser Ala Ser Ala Ala Ala Ala Gly His Gly Ala Pro Pro Pro
85 90 95

Leu Pro Ala Gly Leu Ser Arg Cys Ser Ser Thr Ala Ser Ser Val Asp

```
            100                 105                 110

Ala Ser Ala Ala Ala Gln Asp Arg Ser Leu Pro Ser Cys Gly Ser Asp
        115                 120                 125

Ala Ala Ala Asn Lys Ala Gly Ala Pro Glu Gly Ser Ala Ser Asn Asn
    130                 135                 140

Ala Glu Ser Gly Gly Asn Arg Glu Arg Arg Glu Thr Thr Pro Ser Ser
145                 150                 155                 160

His Phe Pro Gly Asp Leu Ser Asp Leu Glu Ser Asp Leu Ala Gly Lys
                165                 170                 175

Asn Ser Gly Arg Ser Ser Leu Pro Gln Thr Leu Ala Ala Gln Ala Gln
            180                 185                 190

Pro Ala Ala Arg Ser Arg Val Pro Pro Ala Ala Glu Ile Glu Glu Phe
        195                 200                 205

Phe Ala Ala Ala Glu Glu Ala Glu Ala Arg Arg Phe Ala Cys Lys Tyr
    210                 215                 220

Asn Phe Asp Val Ala Arg Gly Val Pro Leu Asp Ser Gly Arg Tyr Glu
225                 230                 235                 240

Trp Thr Pro Ala Val Ser Ser Ser
                245


<210> SEQ ID NO 49
<211> LENGTH: 1371
<212> TYPE: DNA
<213> ORGANISM: Triticum aestivum
<220> FEATURE:
<221> NAME/KEY: misc_feature
<222> LOCATION: (1092)..(1092)
<223> OTHER INFORMATION: n is a, c, g, or t

<400> SEQUENCE: 49

ttcgtccgtt cgcggatggg gaagtacatg cggaagtgcc gggccgcgcc gcgccgcggg     60

cggcggcaag gcggcgccgc cgtcgtggag caccgcgcgc cggtggccct cggcgtccgc    120

acgcggtccc gcgcggccgc cctcaacgcg aagatgagga agcagcagca ggcgacgacg    180

tccacggcgg cgcgcgcggt ggaggatgcg ttgctgggcc gtgacggcgg cgacgcggcc    240

gccgggtgct acctgcatct ccggagcagg aggctgttca tgcctgcttc cgcggcggtg    300

gatcagctcc ggggacttgg ggcggacgag gaggcttcga cggcggggct gccggattct    360

cggccctcgg tggaggcggc ggtcgtggcc ggggtctcgc gctgctccag caccgcgtcg    420

acggcggtgg acgtggcggc tagagagagg agcggcgacg aagcggaggt gagtgggcca    480

ctcactgccc tagaattctc cgtaaattcg gccggtcgat cggcagtttc tgctgctgaa    540

ttacgagatt tggttctgac tgtcttggtc gatcagcagg cgtgcgagag tggcgacgtg    600

gagagctccg tcagcgactc tgagtgcggc ggccgggaca ggtgagtcct cctctctcga    660

taccgacagg aattctgctg aattatccat tgttttctat tctccagggt gatcttgagt    720

tcttgacccg gttttgcttc tgaatttgac ctgtttgaat tgtggtaatc caggagggag    780

accacgccgt cgagccattc cccggcagat ttgagcgacc tggagtcgag ccagtcggcg    840

gacgagcaga agcacaaacg caggaggtat ccggcaacaa cgacgacgac cgcagcgcca    900

ttccgcttag acttggaggc gagagcaagg atgccaccgg cggcagagat cgacgagttc    960

ttcgccgccg cggagaaggc ccaggccgag cgcttcgccg ccaagtaagt ggaaattaca   1020

attgagcaca caagtacaca tacgtcttgg cacttggcag tcgctctatc gccgtcacag   1080

acgccgccac gnctaagcct tgtgctctcg ctgcctcact gcaggtacaa cttcgacgtc   1140
```

-continued gcgcgcggcg tgcctctcaa cgccggccgg ttcgagtgga ccccggtggc caccgtctga 1200
ggctctgagc atgatgcaaa atgacgggaa gctagcggcg gcgcgcgtag aaagggaagg 1260
cctgctggga gtgaaaagag acgctgatcc aacccgcaaa ggaaaacagt aaagagaaag 1320
aggagtgaaa aaagaacaga ataatcccat gcacagcagc ctagagctag a 1371

<210> SEQ ID NO 50
<211> LENGTH: 822
<212> TYPE: DNA
<213> ORGANISM: Triticum aestivum

<400> SEQUENCE: 50
atggggaagt acatgcggaa gtgccgggcc gcgccgcgcc gcgggcggcg gcaaggcggc 60
gccgccgtcg tggagcaccg cgcgccggtg gccctcggcg tccgcacgcg gtcccgcgcg 120
gccgccctca acgcgaagat gaggaagcag cagcaggcga cgacgtccac ggcggcgcgc 180
gcggtggagg atgcgttgct gggccgtgac ggcggcgacg cggccgccgg gtgctacctg 240
catctccgga gcaggaggct gttcatgcct gcttccgcgg cggtggatca gctccgggga 300
cttggggcgg acgaggaggc ttcgacggcg gggctgccgg attctcggcc ctcggtggag 360
gcggcggtcg tggccggggt ctcgcgctgc tccagcaccg cgtcgacggc ggtggacgtg 420
gcggctagag agaggagcgg cgacgaagcg gaggcgtgcg agagtggcga cgtggagagc 480
tccgtcagcg actctgagtg cggcggccgg gacaggaggg agaccacgcc gtcgagccat 540
tccccggcag atttgagcga cctggagtcg agccagtcgg cggacgagca gaagcacaaa 600
cgcaggaggt atccggcaac aacgacgacg accgcagcgc cattccgctt agacttggag 660
gcgagagcaa ggatgccacc ggcggcagag atcgacgagt tcttcgccgc cgcggagaag 720
gcccaggccg agcgcttcgc cgccaagtac aacttcgacg tcgcgcgcgg cgtgcctctc 780
aacgccggcc ggttcgagtg gaccccggtg gccaccgtct ga 822

<210> SEQ ID NO 51
<211> LENGTH: 273
<212> TYPE: PRT
<213> ORGANISM: Triticum aestivum

<400> SEQUENCE: 51

Met Gly Lys Tyr Met Arg Lys Cys Arg Ala Ala Pro Arg Arg Gly Arg
1 5 10 15

Arg Gln Gly Gly Ala Ala Val Val Glu His Arg Ala Pro Val Ala Leu
20 25 30

Gly Val Arg Thr Arg Ser Arg Ala Ala Ala Leu Asn Ala Lys Met Arg
35 40 45

Lys Gln Gln Gln Ala Thr Thr Ser Thr Ala Ala Arg Ala Val Glu Asp
50 55 60

Ala Leu Leu Gly Arg Asp Gly Gly Asp Ala Ala Ala Gly Cys Tyr Leu
65 70 75 80

His Leu Arg Ser Arg Arg Leu Phe Met Pro Ala Ser Ala Ala Val Asp
85 90 95

Gln Leu Arg Gly Leu Gly Ala Asp Glu Glu Ala Ser Thr Ala Gly Leu
100 105 110

Pro Asp Ser Arg Pro Ser Val Glu Ala Ala Val Val Ala Gly Val Ser
115 120 125

Arg Cys Ser Ser Thr Ala Ser Thr Ala Val Asp Val Ala Ala Arg Glu
130 135 140

```
Arg Ser Gly Asp Glu Ala Glu Ala Cys Glu Ser Gly Asp Val Glu Ser
145                 150                 155                 160

Ser Val Ser Asp Ser Glu Cys Gly Gly Arg Asp Arg Arg Glu Thr Thr
                165                 170                 175

Pro Ser Ser His Ser Pro Ala Asp Leu Ser Asp Leu Glu Ser Ser Gln
            180                 185                 190

Ser Ala Asp Glu Gln Lys His Lys Arg Arg Arg Tyr Pro Ala Thr Thr
        195                 200                 205

Thr Thr Thr Ala Ala Pro Phe Arg Leu Asp Leu Glu Ala Arg Ala Arg
    210                 215                 220

Met Pro Pro Ala Ala Glu Ile Asp Glu Phe Phe Ala Ala Ala Glu Lys
225                 230                 235                 240

Ala Gln Ala Glu Arg Phe Ala Ala Lys Tyr Asn Phe Asp Val Ala Arg
                245                 250                 255

Gly Val Pro Leu Asn Ala Gly Arg Phe Glu Trp Thr Pro Val Ala Thr
            260                 265                 270

Val


<210> SEQ ID NO 52
<211> LENGTH: 1364
<212> TYPE: DNA
<213> ORGANISM: Triticum aestivum

<400> SEQUENCE: 52

tttcgtccgt tcgcggatgg ggaagtacat gcggaagtgc aggggcgcgg ccgcgggcgg     60

cggcagggcg gcgccggccg tcgtggagca ccgcgcgccg gtggccctcg gcgtccgcac    120

gcggtcccgc gcggccgcct tcgacgctaa gaggaggaag cagcaggcga cgacgtccac    180

ggcagcgcgc gcggtggacg atgcgttgct gggccgtgac ggcggcgacg cggccggcgg    240

gtgctacctg catctccgga gcaggaggct gttcatgcct gcttccgcgg tggtggatcg    300

gctccgggga caggggggcgg acgaggaggc ttcgacggcg aggctggcgg attccgggcc    360

ttccgtggag gcgggggtcg tcgccggggt ctcgcgctgc tcgagcaccg cgtccacggc    420

agcagacgtg gcggctagag agaggagcgg cgacgaagca gaggtgagtg gtccactgcc    480

ctagaattct ccgctacttc gagctgtcga tcgggccatt tctgctgctg aattaggagg    540

tttggttcct atgtcttgtc ctgcaggcgt gcgagagtcg cgacgtggag agctccgtca    600

gcgactctga gtgcggcggc cgggacaggt gagtcctcct ctctcgatat ataccgacgg    660

gaattctgct gaattatcca ttgttttcta ctccacaagg tgatcttgag ttgaggggcc    720

tggctttgct tctgaatttg acctgttgga ttgtactaat ccaggaggga ggcgacgccg    780

tcgagccgtt cgccggtaga tttgagcgac ctggagtcga gccaggcggc ggacgagcag    840

aagcacaaac gcaggaggtg tccggcagca acgacggcgg cagcagcgcc attccactta    900

gactcggagg cgagagcaag gatgccaccc gcggcagaga tcgacgagtt cttcgccgcc    960

gccgagaagg cccaggccga gcacttcgcg gccaagtaag tggaaattta caatcgagcg   1020

catccgcacg cacgtacata ctcccgtctt ggcagtcgct ccatcgtcgt cacagacgtc   1080

cccgtgccta gctaagcatt gtgctgccgc tgcctcattg caggtacaac ttcgacgtcg   1140

cgcgcggcgt gcctctcaac gccggccggt tcgagtggac cccggtggcc accgtctgag   1200

gctctgatgc aattggcggg gagcgtagcg gcggctcgcg tagaaaggga aggcctgctg   1260

ggagtgaaaa gagacgctga tccaaccccc aaaggaaaac agtaaagaga aagaggagtg   1320

aaaaagaaca gaataatccc atgcacagca ggcctagagc taga                     1364
```

<210> SEQ ID NO 53
<211> LENGTH: 816
<212> TYPE: DNA
<213> ORGANISM: Triticum aestivum

<400> SEQUENCE: 53
atggggaagt acatgcggaa gtgcaggggc gcggccgcgg gcggcggcag ggcggcgccg 60
gccgtcgtgg agcaccgcgc gccggtggcc ctcggcgtcc gcacgcggtc ccgcgcggcc 120
gccttcgacg ctaagaggag gaagcagcag gcgacgacgt ccacggcagc gcgcgcggtg 180
gacgatgcgt tgctgggccg tgacggcggc gacgcggccg gcgggtgcta cctgcatctc 240
cggagcagga ggctgttcat gcctgcttcc gcggtggtgg atcggctccg gggacagggg 300
gcggacgagg aggcttcgac ggcgaggctg gcggattccg ggccttccgt ggaggcgggg 360
gtcgtcgccg gggtctcgcg ctgctcgagc accgcgtcca cggcagcaga cgtggcggct 420
agagagagga gcggcgacga agcagaggcg tgcgagagtc gcgacgtgga gagctccgtc 480
agcgactctg agtgcggcgg ccgggacagg agggaggcga cgccgtcgag ccgttcgccg 540
gtagatttga gcgacctgga gtcgagccag gcggcggacg agcagaagca caaacgcagg 600
aggtgtccgg cagcaacgac ggcggcagca gcgccattcc acttagactc ggaggcgaga 660
gcaaggatgc cacccgcggc agagatcgac gagttcttcg ccgccgccga gaaggcccag 720
gccgagcact tcgcggccaa gtacaacttc gacgtcgcgc gcggcgtgcc tctcaacgcc 780
ggccggttcg agtggacccc ggtggccacc gtctga 816

<210> SEQ ID NO 54
<211> LENGTH: 271
<212> TYPE: PRT
<213> ORGANISM: Triticum aestivum

<400> SEQUENCE: 54

Met Gly Lys Tyr Met Arg Lys Cys Arg Gly Ala Ala Ala Gly Gly Gly
1               5                   10                  15

Arg Ala Ala Pro Ala Val Val Glu His Arg Ala Pro Val Ala Leu Gly
            20                  25                  30

Val Arg Thr Arg Ser Arg Ala Ala Ala Phe Asp Ala Lys Arg Arg Lys
        35                  40                  45

Gln Gln Ala Thr Thr Ser Thr Ala Ala Arg Ala Val Asp Asp Ala Leu
    50                  55                  60

Leu Gly Arg Asp Gly Gly Asp Ala Ala Gly Gly Cys Tyr Leu His Leu
65                  70                  75                  80

Arg Ser Arg Arg Leu Phe Met Pro Ala Ser Ala Val Val Asp Arg Leu
                85                  90                  95

Arg Gly Gln Gly Ala Asp Glu Glu Ala Ser Thr Ala Arg Leu Ala Asp
            100                 105                 110

Ser Gly Pro Ser Val Glu Ala Gly Val Val Ala Gly Val Ser Arg Cys
        115                 120                 125

Ser Ser Thr Ala Ser Thr Ala Ala Asp Val Ala Ala Arg Glu Arg Ser
    130                 135                 140

Gly Asp Glu Ala Glu Ala Cys Glu Ser Arg Asp Val Glu Ser Ser Val
145                 150                 155                 160

Ser Asp Ser Glu Cys Gly Gly Arg Asp Arg Arg Glu Ala Thr Pro Ser
                165                 170                 175

Ser Arg Ser Pro Val Asp Leu Ser Asp Leu Glu Ser Ser Gln Ala Ala

```
            180                 185                 190

Asp Glu Gln Lys His Lys Arg Arg Arg Cys Pro Ala Ala Thr Thr Ala
        195                 200                 205

Ala Ala Ala Pro Phe His Leu Asp Ser Glu Ala Arg Ala Arg Met Pro
    210                 215                 220

Pro Ala Ala Glu Ile Asp Glu Phe Phe Ala Ala Ala Glu Lys Ala Gln
225                 230                 235                 240

Ala Glu His Phe Ala Ala Lys Tyr Asn Phe Asp Val Ala Arg Gly Val
                245                 250                 255

Pro Leu Asn Ala Gly Arg Phe Glu Trp Thr Pro Val Ala Thr Val
            260                 265                 270


<210> SEQ ID NO 55
<211> LENGTH: 1388
<212> TYPE: DNA
<213> ORGANISM: Triticum aestivum

<400> SEQUENCE: 55

gttctttctt ttcgtccgtt cgcggatggg gaagtacatg cggaagtgca gggccgcggc      60

cgcgggcggc ggcagggcgg cgccggccgt cgtggagcac cgcgcgccgg tggccctcgg     120

cgtccgcacg cggtcccgcg cggccgccct cgacgcgaag atgaggaagc agcagcaggc     180

gacgacgtcc acggcggcgc gcgcggtgga ggatgcgttg ctgggccgtg acggcggcga     240

cgcggccgcc gggtgctacc tgcatctccg gagcaggagg ctgttcatgc ctgctgccgc     300

ggtggtggat cagctgcggg gacagggggt gtgtgaggag gcttccacag cggggctgcc     360

ggactctggg ccctcggtgg aggcggcggt cggggccggg gtctcgcgct gctccagcac     420

cgcgtccacg gcggtcgacg tggcggctag agagaggagc ggggatgaag cggaggtgag     480

tggtccactg ccctagaatt ctccgctaat tcgagctatc gatcgggccg tttctgctgc     540

tgaattacga gatttggttc tgactgtctt ggtcgatcag caggcgtgcg agagtcgcga     600

cgtggagagc tccgtcagcg actctgagtg cggcggccgg gacaggtgag tcctcctctc     660

tcgataccga cgggaattct gctgaattac ccattgtttt ctactctcca gggtgatctt     720

gagttgaggg acctggtttt gcttctgaat ttgacctgtt ggattgtggc aatccaggag     780

ggagacgacg ccgtcgagcc gttcgccggt agatttgagc gacctggagt cgagccaggc     840

ggcggacgag cagaagcaca aacgcaggag gtgtccggca acaacgacga cgaccgcagc     900

gccattgcac tatgacttgg aggcgagagc aagagcaagg atgccaccag cggcagagat     960

cgacgagttc ttcgccgccg cggagaaggc ccaggccgag cgcttcgccg ccaagtaagt    1020

ggaaatttac aattgagcaa atccgcacgc acgtcttggc agtcgctcga tcgtcctcac    1080

agacgccgcc gcgcctaagc attgtgctac cgctgcctca ttgcaggtac aacttcgacg    1140

tcgcgcgcgg cgtgcctctc aacgccggcc ggttcgagtg gaccccggtg gccaccgtgt    1200

gagcagagca tgatgcaaat gacggggagc tagcggcggc gcgcgtagaa agggaaggcc    1260

tgctgggagt gaaaagagac gctgatccaa ccccccaaag gaaaacagta aagagaaaga    1320

ggagtaaaaa agaacagaat aatcccatgc acagctgcct agagctaggc atgcagtagc    1380

cctctccc                                                             1388


<210> SEQ ID NO 56
<211> LENGTH: 825
<212> TYPE: DNA
<213> ORGANISM: Triticum aestivum
```

<400> SEQUENCE: 56

```
atggggaagt acatgcggaa gtgcagggcc gcggccgcgg gcggcggcag ggcggcgccg     60

gccgtcgtgg agcaccgcgc gccggtggcc ctcggcgtcc gcacgcggtc ccgcgcggcc    120

gccctcgacg cgaagatgag gaagcagcag caggcgacga cgtccacggc ggcgcgcgcg    180

gtggaggatg cgttgctggg ccgtgacggc ggcgacgcgg ccgccgggtg ctacctgcat    240

ctccggagca ggaggctgtt catgcctgct gccgcggtgg tggatcagct gcggggacag    300

ggggtgtgtg aggaggcttc cacagcgggg ctgccggact ctgggccctc ggtggaggcg    360

gcggtcgggg ccggggtctc gcgctgctcc agcaccgcgt ccacggcggt cgacgtggcg    420

gctagagaga ggagcgggga tgaagcggag gcgtgcgaga gtcgcgacgt ggagagctcc    480

gtcagcgact ctgagtgcgg cggccgggac aggagggaga cgacgccgtc gagccgttcg    540

ccggtagatt tgagcgacct ggagtcgagc caggcggcgg acgagcagaa gcacaaacgc    600

aggaggtgtc cggcaacaac gacgacgacc gcagcgccat tgcactatga cttggaggcg    660

agagcaagag caaggatgcc accagcggca gagatcgacg agttcttcgc cgccgcggag    720

aaggcccagg ccgagcgctt cgccgccaag tacaacttcg acgtcgcgcg cggcgtgcct    780

ctcaacgccg gccggttcga gtggaccccg gtggccaccg tgtga                    825
```

<210> SEQ ID NO 57
<211> LENGTH: 274
<212> TYPE: PRT
<213> ORGANISM: Triticum aestivum

<400> SEQUENCE: 57

```
Met Gly Lys Tyr Met Arg Lys Cys Arg Ala Ala Ala Ala Gly Gly Gly
1               5                   10                  15

Arg Ala Ala Pro Ala Val Val Glu His Arg Ala Pro Val Ala Leu Gly
            20                  25                  30

Val Arg Thr Arg Ser Arg Ala Ala Ala Leu Asp Ala Lys Met Arg Lys
        35                  40                  45

Gln Gln Gln Ala Thr Thr Ser Thr Ala Ala Arg Ala Val Glu Asp Ala
    50                  55                  60

Leu Leu Gly Arg Asp Gly Gly Asp Ala Ala Ala Gly Cys Tyr Leu His
65                  70                  75                  80

Leu Arg Ser Arg Arg Leu Phe Met Pro Ala Ala Ala Val Val Asp Gln
                85                  90                  95

Leu Arg Gly Gln Gly Val Cys Glu Glu Ala Ser Thr Ala Gly Leu Pro
            100                 105                 110

Asp Ser Gly Pro Ser Val Glu Ala Ala Val Gly Ala Gly Val Ser Arg
        115                 120                 125

Cys Ser Ser Thr Ala Ser Thr Ala Val Asp Val Ala Ala Arg Glu Arg
    130                 135                 140

Ser Gly Asp Glu Ala Glu Ala Cys Glu Ser Arg Asp Val Glu Ser Ser
145                 150                 155                 160

Val Ser Asp Ser Glu Cys Gly Gly Arg Asp Arg Arg Glu Thr Thr Pro
                165                 170                 175

Ser Ser Arg Ser Pro Val Asp Leu Ser Asp Leu Glu Ser Ser Gln Ala
            180                 185                 190

Ala Asp Glu Gln Lys His Lys Arg Arg Arg Cys Pro Ala Thr Thr Thr
        195                 200                 205

Thr Thr Ala Ala Pro Leu His Tyr Asp Leu Glu Ala Arg Ala Arg Ala
    210                 215                 220
```

```
Arg Met Pro Pro Ala Ala Glu Ile Asp Glu Phe Phe Ala Ala Ala Glu
225                 230                 235                 240

Lys Ala Gln Ala Glu Arg Phe Ala Ala Lys Tyr Asn Phe Asp Val Ala
                245                 250                 255

Arg Gly Val Pro Leu Asn Ala Gly Arg Phe Glu Trp Thr Pro Val Ala
            260                 265                 270

Thr Val


<210> SEQ ID NO 58
<211> LENGTH: 652
<212> TYPE: DNA
<213> ORGANISM: Triticum aestivum

<400> SEQUENCE: 58

ctcgcttaaa tccgccaaag cgcacccagc ggggccccaa accctagccc gggccgcgcc      60

gcgcatgggc aagtacatgc gcaagcccaa ggtctccggc gaggtggccg tcatggaggt     120

cgccgccgcg ccgctggggg tccgcacccg cgcgcgggcg ctcgcgatgc agaggcagcc     180

gcagggggcg ccgggggcca aggaccaggg ggagtacctg gagctcagga gccggaagct     240

cgagaagctg cccccgccgc cgccgccggc gaggaggagg gcggccgcgg cggagcgtgt     300

cgaggccgag gccgaggccg acaaggtgtc cttcggggag aacgtgctcg agccggaggc     360

catggggagg tgagccttct cctgcgcccg cgattttctt cggttcatgg ggttttattt     420

ctcggcgggg ggattataac cgtgccaggg tttagggttt tgtgtcgtac cgagaagctt     480

tggattgctt cttctgtttc gcgcttcggc tcgttccatt tttccttgtc aatttggctt     540

gttctatccg tgctgcgtgc ggggctcgaa tttggtgtcg atgctatttt ccccaatatc     600

tttcttatta agctttgctg tttattgggg atttttctg tcccaactct tc              652


<210> SEQ ID NO 59
<211> LENGTH: 905
<212> TYPE: DNA
<213> ORGANISM: Triticum aestivum

<400> SEQUENCE: 59

aggcaaattc ggtagaaatg tgtagccaat tgtggcattg ctaggcctag ttagaaccaa      60

acaaccccgg atactcataa ggggggatt ccttattttt ttatgaccac ggatgatatc      120

gatatgtttt cttctttttg catacctgt taagttacag gtgatttttt cccttttgct      180

acgcgtcctc gctatggttg tttctaaaaa ttgagtgtgt atgtatgttt tgtggctagc     240

aggggtacca gggagacgac gccctgcagc ttgattaggg actcgggaat gataagcact     300

cctggatcca caacaagacc gagccactcg aattcccatc gcagggtgca agctccagcg     360

cgccatatta ttccaagttc agcagagatg aatgagttct tctctgctgc agagcaaccg     420

caacagcaag ccttcatcga caagtacgac attgtttggt tctctcagtc agttaacctt     480

gtctaattaa aaaaaatctt tcaatatctt tgcagtgaag aatgccaact cagcgtgcaa     540

tgtggttttg acacgtgata tgttcatgcc tttgctcttg ataaaaagtg tgattataac     600

actaacaaca tggtttcatg gcttaataat cttcaggtac aactttgatc ctgtgaacga     660

ctgtcctctc ccaggccgat acgagtgggt gaagctagac tgataattct ccaggaagga     720

gagcaccatg tatctctctg ctccctccac cttagcgtcg tggtagaggc gcgcaccgtc     780

gtgttagctt tgtttccgtt gtaaaaagaa ttagggttag cctgtagtag cctcaatggt     840

tgtgtaacat acagaagtaa tgctgagtta caccctatcc ctcaaactcc ccaaatgtcg     900
```

gtagc 905

<210> SEQ ID NO 60
<211> LENGTH: 573
<212> TYPE: DNA
<213> ORGANISM: Triticum aestivum

<400> SEQUENCE: 60
atgggcaagt acatgcgcaa gcccaaggtc tccggcgagg tggccgtcat ggaggtcgcc 60
gccgcgccgc tgggggtccg cacccgcgcg cgggcgctcg cgatgcagag gcagccgcag 120
ggggcgccgg gggccaagga ccagggggag tacctggagc tcaggagccg gaagctcgag 180
aagctgcccc cgccgccgcc gccggcgagg aggagggcgg ccgcggcgga gcgtgtcgag 240
gccgaggccg aggccgacaa ggtgtccttc ggggagaacg tgctcgagcc ggaggccatg 300
gggaggggta ccagggagac gacgccctgc agcttgatta gggactcggg aatgataagc 360
actcctggat ccacaacaag accgagccac tcgaattccc atcgcagggt gcaagctcca 420
gcgcgccata ttattccaag ttcagcagag atgaatgagt tcttctctgc tgcagagcaa 480
ccgcaacagc aagccttcat cgacaagtac aactttgatc ctgtgaacga ctgtcctctc 540
ccaggccgat acgagtgggt gaagctagac tga 573

<210> SEQ ID NO 61
<211> LENGTH: 190
<212> TYPE: PRT
<213> ORGANISM: Triticum aestivum

<400> SEQUENCE: 61

Met Gly Lys Tyr Met Arg Lys Pro Lys Val Ser Gly Glu Val Ala Val
1 5 10 15

Met Glu Val Ala Ala Ala Pro Leu Gly Val Arg Thr Arg Ala Arg Ala
20 25 30

Leu Ala Met Gln Arg Gln Pro Gln Gly Ala Pro Gly Ala Lys Asp Gln
35 40 45

Gly Glu Tyr Leu Glu Leu Arg Ser Arg Lys Leu Glu Lys Leu Pro Pro
50 55 60

Pro Pro Pro Pro Ala Arg Arg Arg Ala Ala Ala Ala Glu Arg Val Glu
65 70 75 80

Ala Glu Ala Glu Ala Asp Lys Val Ser Phe Gly Glu Asn Val Leu Glu
85 90 95

Pro Glu Ala Met Gly Arg Gly Thr Arg Glu Thr Thr Pro Cys Ser Leu
100 105 110

Ile Arg Asp Ser Gly Met Ile Ser Thr Pro Gly Ser Thr Thr Arg Pro
115 120 125

Ser His Ser Asn Ser His Arg Arg Val Gln Ala Pro Ala Arg His Ile
130 135 140

Ile Pro Ser Ser Ala Glu Met Asn Glu Phe Phe Ser Ala Ala Glu Gln
145 150 155 160

Pro Gln Gln Gln Ala Phe Ile Asp Lys Tyr Asn Phe Asp Pro Val Asn
165 170 175

Asp Cys Pro Leu Pro Gly Arg Tyr Glu Trp Val Lys Leu Asp
180 185 190

<210> SEQ ID NO 62
<211> LENGTH: 651
<212> TYPE: DNA

<213> ORGANISM: Triticum aestivum

<400> SEQUENCE: 62

```
ctcgcttaaa tccgcaaggc gcacccaggg gggcccaaac cctagcccgg gccgcgccgc     60
gcatgggcaa gtacatgcgc aagcccaagg tctccggcga ggtggccgtc atggaggtcg    120
ccgccgcgcc gctaggggtc cgcacccgcg cacgagcgct cgcgatgcag aggcagccgc    180
agggggcggc ggtggccaag gaccaggggg agtacctgga gctcaggagt cggaagctcg    240
agaagctgcc cccgccgccg ccgccggcga ggaggagggc ggccgcggcg gagcgtgtcg    300
aggccgaggc cgaggccgac gaggtgtcct tcggtgagaa cgtgctcgag tcggaggcca    360
tggggaggtg agccttctcc tgcgccggcg attttcttcg gttattgggg ttttatttct    420
cggcgggggg attattaccg tgctagggtt tagggttttg tgtcgtaccg agaagctttg    480
gattgcttct tctatttcgc gcttcggctc gtttcatttc tccttgtcaa tttggcttgt    540
tctatccgtg ctgcgtgcgg ggctcgaatt tggtgtggat gctattttcc ccaatatctt    600
tgttactatt aaactttgct gtttattggg gatttttccg tctaactctt c             651
```

<210> SEQ ID NO 63
<211> LENGTH: 1071
<212> TYPE: DNA
<213> ORGANISM: Triticum aestivum

<400> SEQUENCE: 63

```
ttgggggggg ttactagccc caccattctt ttgtttccca tgggccttgt gtttcggttg     60
tgtgctagcc tttatatggc atatgagata gattgaaggg ctgtttagtt aggcaacttg    120
tggccccaat ctgtttgaac taaccttagg caagtttggt aagaaatgtg tggcaaattg    180
tggcattgct aggcctagtt agaaccaaac aaccccggat actcataagg gggggattcc    240
ttattttta tgactattga tatgtgttct tctttttcca taccctgtta agttacaggt    300
gatttttcc cttttgctat gcttcctctc tatggttgtt tctaaaaatt gagtgtgtat    360
gtatgttttg tggctagcag gggtaccagg gagacgacgc cctgcagctt gattagggac    420
tcgggaacga taagcactcc tggatccaca acaagaccga gccactcgaa ttcccatcgc    480
agggtgcaag ctccagcgcg ccatattatt ccatgttcag cagagatgaa tgagttcttc    540
tctgctgcgg agcaaccgca acagcaagcc ttcatcgaca agtacggcat tgtttggttc    600
tctcagtcag ttaaccttgt ctaatttaaa aaaagggaaa tctttcaata tcttcgcagt    660
gaagaatgcc aactcagcgt gcaatgtggt tttgacacgt gatatgttta cgcctttgct    720
cttgataaaa agtgtgatta taacactaac aacatggttt catggcttaa taatcttcag    780
gtacaacttt gatcctgtga acgactgtcc tctcccaggc cgatacgagt gggtgaagct    840
agactgataa ttctccagga aggagagcat catgtacttc tccgctccct ccaccttagc    900
gtcgtggtaa aggcgcgccc cgtcgtgtta gctttgtttc cgttgtaaaa agaattaggt    960
tagcctgtag tagcctcaat ggtcgtgtaa catacagaag taatgctgag ttacacccta   1020
atccctcaaa ctccaatgta acggttagca gctcattctg aaatgaccac a            1071
```

<210> SEQ ID NO 64
<211> LENGTH: 573
<212> TYPE: DNA
<213> ORGANISM: Triticum aestivum

<400> SEQUENCE: 64

```
atgggcaagt acatgcgcaa gcccaaggtc tccggcgagg tggccgtcat ggaggtcgcc     60
```

gccgcgccgc taggggtccg cacccgcgca cgagcgctcg cgatgcagag gcagccgcag 120
ggggcggcgg tggccaagga ccagggggag tacctggagc tcaggagtcg gaagctcgag 180
aagctgcccc cgccgccgcc gccggcgagg aggagggcgg ccgcggcgga gcgtgtcgag 240
gccgaggccg aggccgacga ggtgtccttc ggtgagaacg tgctcgagtc ggaggccatg 300
gggaggggta ccagggagac gacgccctgc agcttgatta gggactcggg aacgataagc 360
actcctggat ccacaacaag accgagccac tcgaattccc atcgcagggt gcaagctcca 420
gcgcgccata ttattccatg ttcagcagag atgaatgagt tcttctctgc tgcggagcaa 480
ccgcaacagc aagccttcat cgacaagtac aactttgatc ctgtgaacga ctgtcctctc 540
ccaggccgat acgagtgggt gaagctagac tga 573

<210> SEQ ID NO 65
<211> LENGTH: 190
<212> TYPE: PRT
<213> ORGANISM: Triticum aestivum

<400> SEQUENCE: 65

Met Gly Lys Tyr Met Arg Lys Pro Lys Val Ser Gly Glu Val Ala Val
1 5 10 15

Met Glu Val Ala Ala Ala Pro Leu Gly Val Arg Thr Arg Ala Arg Ala
20 25 30

Leu Ala Met Gln Arg Gln Pro Gln Gly Ala Ala Val Ala Lys Asp Gln
35 40 45

Gly Glu Tyr Leu Glu Leu Arg Ser Arg Lys Leu Glu Lys Leu Pro Pro
50 55 60

Pro Pro Pro Ala Ala Arg Arg Arg Ala Ala Ala Ala Glu Arg Val Glu
65 70 75 80

Ala Glu Ala Glu Ala Asp Glu Val Ser Phe Gly Glu Asn Val Leu Glu
85 90 95

Ser Glu Ala Met Gly Arg Gly Thr Arg Glu Thr Thr Pro Cys Ser Leu
100 105 110

Ile Arg Asp Ser Gly Thr Ile Ser Thr Pro Gly Ser Thr Thr Arg Pro
115 120 125

Ser His Ser Asn Ser His Arg Arg Val Gln Ala Pro Ala Arg His Ile
130 135 140

Ile Pro Cys Ser Ala Glu Met Asn Glu Phe Phe Ser Ala Ala Glu Gln
145 150 155 160

Pro Gln Gln Gln Ala Phe Ile Asp Lys Tyr Asn Phe Asp Pro Val Asn
165 170 175

Asp Cys Pro Leu Pro Gly Arg Tyr Glu Trp Val Lys Leu Asp
180 185 190

<210> SEQ ID NO 66
<211> LENGTH: 651
<212> TYPE: DNA
<213> ORGANISM: Triticum aestivum

<400> SEQUENCE: 66
ctcgcttaaa tccgcaaggc gcacccaggg gggcccaaac cctagcccgg gccgccccgc 60
gcatgggcaa gtacatgcgc aagcccaagg tctccggcga ggtggccgtc atggaggtcg 120
ccgccgcgcc gctgggtgtc cgcacccgcg cgcgagcgct cgcgatgcag aggcagccgc 180
agggggcgcc gggggccaag gaccaggggg agtacctgga gctcaggagc cggaagctcg 240
agaagctgcc cctgccgccg ccgccggcga ggaggagggc ggccgcggcg gagcgtgtcg 300
aggccgaggc cgaggccgac gaggtgtcct tcggggagaa cgtgctcgag tcggaggcca 360
tggggaggtg agccgccttc tcctgcgccg gcgattttct tcggttctgg ggttttattt 420
ctcggcgggg ggattattac cgtgctaggg tttagggttt tgtgtcgtac cgagaagctt 480
tggattgctt gttccatttc acgcttcggc tcgtttcttt tttccttgtc agtttggctt 540
gttctgtccg tgctgcgtgc ggggctcgaa tttggtgtgg atgctatttt ccccaatatc 600
tttgttaagc ttggctgttt tattggggat ttttttcctg gctaactctt c 651

<210> SEQ ID NO 67
<211> LENGTH: 1073
<212> TYPE: DNA
<213> ORGANISM: Triticum aestivum

<400> SEQUENCE: 67 gggggggtt aactagccca ccattttttt gtttcccatg ggccttgtgt tttggttgtg 60
tgctagcctt tatatggcat atgagataga ttgaagggct gtttggttag gcaacttgtg 120
gctccaattt gtttgaacta accttaggca agtttggtga gaaatgtgtg gcaaattgtg 180
gcattgctag gcctagttag aaccaaacaa ccccggatac tcataagggg gggattcctt 240
atttcttacg accacggatg atatcgatat gtgttcttct ttttgcatac cctgttaagt 300
tacaggtgat ttttcccctt ttgctatact tcctctctat ggttgtttct aaaaattgag 360
tgtgtatgta tgttttgtgg ctagcagggg taccagggag acgacgccct gcagcttgat 420
tagggactcg ggaacgataa gcactcctgg atccacaaca agaccaagcc actcgaattc 480
ccatcgcagg gtgcaagctc cagcgcgcca tattattcca tgttcagcag agatgaatga 540
gttcttctct gctgcggagc aaccgcaaca gcaagccttc atcgacaagt acggcattgt 600
ttggttctct cagtcagtta accttgtcta attaaaaaaa tctttcaata tcttcgcagt 660
gaagaatgcc aactcagagt gcaatgtggt tttgacacgt gatatgttca cgcctttgct 720
cttgataaaa agtgtgatta taacactaac aacatggttt catggcttaa taatcttcag 780
gtacaacttt gatcctgtga acgactgtcc tctcccaggc cgatacgagt gggtgaagct 840
agactgataa ttctccagga aggagagcac catgtacctc tccgctccct ccaccttagc 900
gtcgtggtag aggcgcgcac cgccgtgtta gctttgtttc cgttgtaaaa agaattaggg 960
ttagcctgta gtagcctcaa tggtcttgta acatacagaa gtaatgctga gttacaccct 1020
aatccctcaa aactccaatg taacggttag cagctcattc tgtaatgacc aca 1073

<210> SEQ ID NO 68
<211> LENGTH: 573
<212> TYPE: DNA
<213> ORGANISM: Triticum aestivum

<400> SEQUENCE: 68
atgggcaagt acatgcgcaa gcccaaggtc tccggcgagg tggccgtcat ggaggtcgcc 60
gccgcgccgc tgggtgtccg cacccgcgcg cgagcgctcg cgatgcagag gcagccgcag 120
ggggcgccgg gggccaagga ccagggggag tacctggagc tcaggagccg gaagctcgag 180
aagctgcccc tgccgccgcc gccggcgagg aggagggcgg ccgcggcgga gcgtgtcgag 240
gccgaggccg aggccgacga ggtgtccttc ggggagaacg tgctcgagtc ggaggccatg 300
gggaggggta ccagggagac gacgccctgc agcttgatta gggactcggg aacgataagc 360
actcctggat ccacaacaag accaagccac tcgaattccc atcgcagggt gcaagctcca 420
gcgcgccata ttattccatg ttcagcagag atgaatgagt tcttctctgc tgcggagcaa 480
ccgcaacagc aagccttcat cgacaagtac aactttgatc ctgtgaacga ctgtcctctc 540
ccaggccgat acgagtgggt gaagctagac tga 573

<210> SEQ ID NO 69
<211> LENGTH: 190
<212> TYPE: PRT
<213> ORGANISM: Triticum aestivum

<400> SEQUENCE: 69

Met Gly Lys Tyr Met Arg Lys Pro Lys Val Ser Gly Glu Val Ala Val
1 5 10 15

Met Glu Val Ala Ala Ala Pro Leu Gly Val Arg Thr Arg Ala Arg Ala
20 25 30

Leu Ala Met Gln Arg Gln Pro Gln Gly Ala Pro Gly Ala Lys Asp Gln
35 40 45

Gly Glu Tyr Leu Glu Leu Arg Ser Arg Lys Leu Glu Lys Leu Pro Leu
50 55 60

Pro Pro Pro Pro Ala Arg Arg Arg Ala Ala Ala Ala Glu Arg Val Glu
65 70 75 80

Ala Glu Ala Glu Ala Asp Glu Val Ser Phe Gly Glu Asn Val Leu Glu
85 90 95

Ser Glu Ala Met Gly Arg Gly Thr Arg Glu Thr Thr Pro Cys Ser Leu
100 105 110

Ile Arg Asp Ser Gly Thr Ile Ser Thr Pro Gly Ser Thr Thr Arg Pro
115 120 125

Ser His Ser Asn Ser His Arg Arg Val Gln Ala Pro Ala Arg His Ile
130 135 140

Ile Pro Cys Ser Ala Glu Met Asn Glu Phe Phe Ser Ala Ala Glu Gln
145 150 155 160

Pro Gln Gln Gln Ala Phe Ile Asp Lys Tyr Asn Phe Asp Pro Val Asn
165 170 175

Asp Cys Pro Leu Pro Gly Arg Tyr Glu Trp Val Lys Leu Asp
180 185 190

<210> SEQ ID NO 70
<211> LENGTH: 2259
<212> TYPE: DNA
<213> ORGANISM: Triticum aestivum
<220> FEATURE:
<221> NAME/KEY: misc_feature
<222> LOCATION: (2103)..(2103)
<223> OTHER INFORMATION: n is a, c, g, or t

<400> SEQUENCE: 70
aagccggcgc catgggcaag tacatgcgca agagcaaggc ctcgggggag gtggccgtca 60
tggaggtcgc cggcgcgctg ctcggcgtcc gcacccgctc ccgcaccctc gccgcgcagc 120
agcagcgcgc tccgtcccct tcgccgcagc gcaagggcca cgaggacggc gactacctcg 180
agctcaggag caggaggctc gagaagcagc cgccgccggg gcccaaggac aaggaggacg 240
cgccgcagcc gccggccgcc ggtgggagga ggatggagca ggcgccgtcg tcgttcgccg 300
ccgagggctt cgaggccgac ctcgaggtct ccttcggcga caacgtcctg gactgggacg 360
ccaccgacag gtaacaacag agcaccagac ttttctctcc tccccttcct cttccgccaa 420
tcccccccct ccgcctcagt cagcaatccc ctctcgcgcc ccgccccggc cgatacgaat 480
acgactgagg tttagggttt atccgccgcc gtgtcgccgt cctgctccat tagcgccgcc 540
gcgtgctctc aaatctcaac tctcaggcgc cggcaacctc aagaaccccc tccctatcag 600
ttttctcaga cgagcgccgc cgctggtccg gcgattttct tctccatcag gattgaagcg 660
cccaaatagc cacaccttcc gctgattgtg cccggatgcc tgcaagaatc aaggcctccg 720
ctggccttga tttcctcaag ccttagccgt tggctggctg gagcttgaaa gaatcgaaga 780
aacgcctgtc cgctgtgttg acccggggaa aaaggccccc ctatttcccc ccctccagaa 840
aagccgccat tttcccctc caaacaaaga tgcatccagg cgcactcaat caaccccaa 900 tcaaagtggg cgctgcactt gattagtgga gcctcctcct cctcctcctc cagtggccgt 960
ggccgtggcc tccgcctttt ccccgtagtg gcaggggaaa gtagccccct ttccccttcc 1020
ccaccacagc cgccctccat tggcctggcc ccaatctttc ccaacagcaa ccagagggag 1080
agaggcccct ctcccgccct ttcgccagca atttcaatcc cacaaagccg agcgccaccg 1140
ccgtcgcgct cagggcccca ttcgccaccg ccgtgggtga aaatggcaag ctgctcatca 1200
ttggcccttg taccggagcg ccaccgccgc cattgaatgc ctgcccttgt ctggagggat 1260
atggctggac ctttccgctt gaatggacac tctgaccgga ccacgttttt gttctagcca 1320
gtgcctccat tcatatttac cccttggccc ttgttgtgag catttgcacc agccacttga 1380
agagaaaaga ttttacttct agtaattcag gccttggaag acctcggtaa atgtttcccc 1440
agcttcttta attccacacc ttgttcgtag gattgatctc gcgcgtggtc ccttgtcccc 1500
cggcgtatgc atgttgaacg tgctcccccc atttagcagc ttgcttggcc gtattaggcc 1560
aagttgttgc ttgcttgtca gcattcagtc attcagcgtg cttgtgctgc tgctgcgcca 1620
ataatcaggc acacctcaca ttgtgtgatg tggggcactt gttagcaatg aaatggacaa 1680
gatcatgcgg catgctagaa aatgaatgag ctgtcgtgtt cagcttcctg tagcttggtc 1740
tcatctgagc tcaccaacca ggcttgattc tgcagcagta ctacgtaatt tgcaaggccc 1800
tcttgtgcat ttctagcttc tgaacctcat gttgtgctgt tcgtcggtgc tgcgtgcagg 1860
ggcgccaggg agacgacgcc gtgcagcctc atctacagct cggagacgat gagcaccccc 1920
gggtcggcga ccggaggagc ccgcaaccac tcccgccgca gggcgcagac gccggtctgc 1980
cgctacgtgc cgagctcgct ggagatggac gagttcttcg ccgccgccga gcagcagcaa 2040
caccagacct tcagggacaa gtaagagcat gcttccttct gctcttcttc acatactgta 2100
aanagaaact tgctaacact cgactgtgat gttgaaatca ggtacaactt ctgtcctgcg 2160
aggggctgcc cgctccccgg gcggtacgag tggacggtgc tagactgcta gggcttcata 2220
cctcacacca ccaccaggag ctcctccatt gatctctgt 2259

<210> SEQ ID NO 71
<211> LENGTH: 630
<212> TYPE: DNA
<213> ORGANISM: Triticum aestivum

<400> SEQUENCE: 71
atgggcaagt acatgcgcaa gagcaaggcc tcgggggagg tggccgtcat ggaggtcgcc 60
ggcgcgctgc tcggcgtccg cacccgctcc cgcaccctcg ccgcgcagca gcagcgcgct 120
ccgtcccctt cgccgcagcg caagggccac gaggacggcg actacctcga gctcaggagc 180
aggaggctcg agaagcagcc gccgccgggg cccaaggaca aggaggacgc gccgcagccg 240
ccggccgccg gtgggaggag gatggagcag gcgccgtcgt cgttcgccgc cgagggcttc 300
gaggccgacc tcgaggtctc cttcggcgac aacgtcctgg actgggacgc caccgacagg 360

```
ggcgccaggg agacgacgcc gtgcagcctc atctacagct cggagacgat gagcaccccc    420

gggtcggcga ccggaggagc ccgcaaccac tcccgccgca gggcgcagac gccggtctgc    480

cgctacgtgc cgagctcgct ggagatggac gagttcttcg ccgccgccga gcagcagcaa    540

caccagacct tcagggacaa gtacaacttc tgtcctgcga ggggctgccc gctccccggg    600

cggtacgagt ggacggtgct agactgctag                                      630


<210> SEQ ID NO 72
<211> LENGTH: 209
<212> TYPE: PRT
<213> ORGANISM: Triticum aestivum

<400> SEQUENCE: 72

Met Gly Lys Tyr Met Arg Lys Ser Lys Ala Ser Gly Glu Val Ala Val
1               5                   10                  15

Met Glu Val Ala Gly Ala Leu Leu Gly Val Arg Thr Arg Ser Arg Thr
            20                  25                  30

Leu Ala Ala Gln Gln Gln Arg Ala Pro Ser Pro Ser Pro Gln Arg Lys
        35                  40                  45

Gly His Glu Asp Gly Asp Tyr Leu Glu Leu Arg Ser Arg Arg Leu Glu
    50                  55                  60

Lys Gln Pro Pro Pro Gly Pro Lys Asp Lys Glu Asp Ala Pro Gln Pro
65                  70                  75                  80

Pro Ala Ala Gly Gly Arg Arg Met Glu Gln Ala Pro Ser Ser Phe Ala
                85                  90                  95

Ala Glu Gly Phe Glu Ala Asp Leu Glu Val Ser Phe Gly Asp Asn Val
            100                 105                 110

Leu Asp Trp Asp Ala Thr Asp Arg Gly Ala Arg Glu Thr Thr Pro Cys
        115                 120                 125

Ser Leu Ile Tyr Ser Ser Glu Thr Met Ser Thr Pro Gly Ser Ala Thr
    130                 135                 140

Gly Gly Ala Arg Asn His Ser Arg Arg Arg Ala Gln Thr Pro Val Cys
145                 150                 155                 160

Arg Tyr Val Pro Ser Ser Leu Glu Met Asp Glu Phe Phe Ala Ala Ala
                165                 170                 175

Glu Gln Gln Gln His Gln Thr Phe Arg Asp Lys Tyr Asn Phe Cys Pro
            180                 185                 190

Ala Arg Gly Cys Pro Leu Pro Gly Arg Tyr Glu Trp Thr Val Leu Asp
        195                 200                 205

Cys


<210> SEQ ID NO 73
<211> LENGTH: 2282
<212> TYPE: DNA
<213> ORGANISM: Triticum aestivum

<400> SEQUENCE: 73

ctccccatta ttccgcgatt cccctcccct cccctccctc ccagccagct gcccaccgga     60

agcagaggga agcagaggag aggccggggc cggcgccatg ggaagtaca tgcgcaagag    120

caagccctcg gggaggtgg ccgtcatgga ggtcgccggc gcgctgctcg gcgtccgcac    180

ccgctcccgc accctcgccg cgcagcagca gcgcgccccc tccccgtccc cctcgccgca    240

gcgcaagggg caggaggacg gcgaccccgg ggctggcgac tacctcgagc tcaggagcag    300

gcggctcgag aagcagccgc cgccgggggc cagggagaag gaggacgcgc cgcagccggc    360
```

-continued

```
cgcgaggagg gccgccgccg ctggcgggag gaggatggag caggcgccgt cgttcgccgc    420
cgaggggttc gaggccgacc tcgaggtctc cttcggcgac aacgtgctgg actgggacgc    480
caccgacagg taacaacaga gcaccagttc tttctttctt tctttcttcc cccaatcccc    540
cctctccggt tcagccagca atcccttctc gcgcccgggt gataccaata cgattgggat    600
ttatgcttta tcgcgctcca ttagcgccgc cgcgtggtct caaatctcaa ctctgaagcg    660
ccggcaacct caagaatccc ctccctatga gtttcctcag acgagcgccg acgctggttt    720
tctttctccc caggattgaa gcgcccaaac atccacagct tccgctgatt gtgccgggat    780
tcttgcaaga atcatcggtt ctccgttttc agcctgaatg aatttcctca accattagcc    840
gttggcgtcc gctcgaaaga atccaagaaa gaaacgcctg cccgccgtgt tgacccggcg    900
aaaaaggccc ccatttcccc ccctccaaag aagccaccat tttcccgtc caaacaatca     960
aaggcgcact caatcaaccc aacccccaat caaagtgggc gctgcacttg attagtggag   1020
cctcctccag aaatcagtgg agcctcctcc ccctccagtg gccgcggccg tggctccgcc   1080
ttttcccgat agtggcagag gaaagtagcc ccctttccat tccccttccc caccacagcc   1140
gccctccatt ggctcggccc caatctttcc tctcccgctc tttcccgggc aatttcaacc   1200
ccccaaaggc gccaccgccg tcgcactcag ggcccagttt ctcgcccgcc cgcccgccag   1260
ccgccaccgc cgtgggcgaa aatggcatgc agctcatcat cagcacttgt accagagcgc   1320
caccgccgcc attgaatgct cgctggcctc ctgttagctt cctgaccggg ccttgagtgg   1380
acgccggacc acgtttttgt tcggaacaga ttttactttg gtcaggccgt ggaagacctc   1440
agtaaatata tctttctccg gcttatttag ttctacgtat gttcgcatga ttgatcccgt   1500
ggtccctttg cccggcgtat gcatgttgga cgcacgcgcc catttagctc gcttgcttgg   1560
ccgtgttagg ccaagttgtt gcttgtttgt cagcgtccag tcattcagcg tgcttgtgct   1620
tgcgctgcac caataatcag gtgcgcctca cattgtctag cgtggggcac ttgcaagcaa   1680
tgaaatggac aagatcatgc atgctagaaa atgaatgagc tgtcgtgttc gacttcctgt   1740
agcttgctgt cacccgagct caccaaccaa gcttgcatct gcagtagtaa tttgcaagac   1800
ctcgtgtgca tttcagcttc tgaacctcat gtgctgttgg ttgcttgcag gggcaccagg   1860
gagacgacgc cgtgcagcct gatctacagc tcggagacga tgagcacccc ggggtcggcg   1920
acgggagccc gcaaccattc ccggcgcagg gcgcagacgc cggtgtgccg ctacgtcccg   1980
agctcgctcg agatggacga gttcttcgcc gccgcggagc agcagcagca ccagagcttc   2040
agggacaagt aagaagaact ctgcctcctc ctcctcctcc tcttcacctg aactatgcat   2100
acggcaaagc gaaacttgct gacactggac tgctctgatc taaaaataac caggtacaac   2160
ttctgcccgg cgagcgagcg cccgctcccg gggcggtacg agtggacggt gctagactgc   2220
tagggcttcc tcatacctca caccaccacc accaccacca ggagctcctc cattgatctc   2280
gt                                                                  2282
```

<210> SEQ ID NO 74
<211> LENGTH: 660
<212> TYPE: DNA
<213> ORGANISM: Triticum aestivum

<400> SEQUENCE: 74

```
atggggaagt acatgcgcaa gagcaagccc tcgggggagg tggccgtcat ggaggtcgcc     60
ggcgcgctgc tcggcgtccg cacccgctcc cgcaccctcg ccgcgcagca gcagcgcgcc    120
```

```
ccctccccgt ccccctcgcc gcagcgcaag gggcaggagg acggcgaccc cggggctggc    180

gactacctcg agctcaggag caggcggctc gagaagcagc cgccgccggg ggccagggag    240

aaggaggacg cgccgcagcc ggccgcgagg agggccgccg ccgctggcgg gaggaggatg    300

gagcaggcgc cgtcgttcgc cgccgagggg ttcgaggccg acctcgaggt ctccttcggc    360

gacaacgtgc tggactggga cgccaccgac aggggcacca gggagacgac gccgtgcagc    420

ctgatctaca gctcggagac gatgagcacc ccggggtcgg cgacgggagc ccgcaaccat    480

tcccggcgca gggcgcagac gccggtgtgc cgctacgtcc cgagctcgct cgagatggac    540

gagttcttcg ccgccgcgga gcagcagcag caccagagct tcagggacaa gtacaacttc    600

tgcccggcga gcgagcgccc gctcccgggg cggtacgagt ggacggtgct agactgctag    660
```

```
<210> SEQ ID NO 75
<211> LENGTH: 140
<212> TYPE: PRT
<213> ORGANISM: Triticum aestivum

<400> SEQUENCE: 75

Met Gly Lys Tyr Met Arg Lys Ser Lys Pro Ser Gly Glu Val Ala Val
1               5                   10                  15

Met Glu Val Ala Gly Ala Leu Leu Gly Val Arg Thr Arg Ser Arg Thr
            20                  25                  30

Leu Ala Ala Gln Gln Gln Arg Ala Pro Ser Pro Ser Pro Ser Pro Gln
        35                  40                  45

Arg Lys Gly Gln Glu Asp Gly Asp Pro Gly Ala Gly Asp Tyr Leu Glu
    50                  55                  60

Leu Arg Ser Arg Arg Leu Glu Lys Gln Pro Pro Pro Gly Ala Arg Glu
65                  70                  75                  80

Lys Glu Asp Ala Pro Gln Arg Pro Arg Gly Gly Pro Pro Pro Leu Ala
                85                  90                  95

Gly Gly Gly Trp Ser Arg Arg Arg Arg Ser Pro Pro Arg Gly Ser Arg
            100                 105                 110

Pro Thr Ser Arg Ser Pro Ser Ala Thr Thr Cys Trp Thr Gly Thr Pro
        115                 120                 125

Pro Thr Gly Ala Pro Gly Arg Arg Arg Arg Ala Ala
    130                 135                 140
```

```
<210> SEQ ID NO 76
<211> LENGTH: 2430
<212> TYPE: DNA
<213> ORGANISM: Triticum aestivum
<220> FEATURE:
<221> NAME/KEY: misc_feature
<222> LOCATION: (2415)..(2415)
<223> OTHER INFORMATION: n is a, c, g, or t

<400> SEQUENCE: 76

aatggggaag tacatgcgta agagcaaggc ctcgggggag gtggccgtca tggaggtcgc     60

cggcgcgctg ctcggcgtcc gcacccgctc ccgcaccctc gccgcgcagc agcagcgcgc    120

tccgtcccct tcgccgcagc gcaagggcca cgaggacggc gactacctcg agctcaggag    180

caggaggctc gagaagcagc cgccgccggg gcccaaggac aaggaggacg cgccgcagcc    240

gccggccgcc ggtgggaggg ggatggagtc gttcgcggcc gaggggttcg aggccgacct    300

cgaggtctcc ttcggcgaca acgtgctgga ctgggacgcc accgacaggt aagaacagag    360

caccagcgcc ttctttcctc ccccttcct ctcccctcaa tccttcccct ccggttcagt    420
```

-continued

```
cggcaatccc ctccgccccg gccgatacca atacgattga ggtttagggt tcatatccgc    480
cgctgtttcg ttctgctcca ttagcgccgc cgctgcgcgg cctcgaatct caacacgaat    540
cccctcccct ctcaaacgag cgccgccgct ggcccgctgg ttttctccac aggattgagc    600
caaaccttgt gctgatttcg cccggatgct tgcgggaata atcccttgca gtttcctgat    660
tttcctcaag ctggagccgt tggccgtagc tttgaaagaa tccaagaaac gcctgcccgc    720
cgtgttgacc cggcgaaaaa gggcccccat tttcccccct ccaaaaaagc cgccattttt    780
cccggccaaa caaagatgca tccatcaagg cgcactcaat caacccccaa tcaaagtggg    840
cgctgcactc gattagtgga gcctcctcct ccagtggccg tggcctttc cccgtagtgg    900
caggggaaag tagccttccc caccatagcc gccctccatt ggcttggcct caatctttcc    960
caacagcaac cagagggaga ggcccctctc ccgctctttc gccagcaatt tcaatccccc   1020
aaaggcgcca ccgccgtcgc ggtcagggcc ccatttctcg cccgcccgcc agtcgccacc   1080
gccgtgggtg aaaatggctt gctgctcatc attggccctt gtaccagagc gccaccgccg   1140
ccattgaatg cttgctggcc tcttgttagc ttcctgaccg gacgttgaat ggacaccgga   1200
ccacgttatt gttcagacgc ttggggtgaa agggagctgc ctccgttaaa ttacctggtg   1260
ttgtgagtgc accagccact tgaacagcac aaattttact tactggtagt tcaggccttg   1320
gaagacctca gtaaatatat ctttctccgg cttatttaat tctacttacg ttcgtatgat   1380
tgatctcgtg gtcccgttgt ccggcgtatg catgttgaac gcgcccattt agcttgcttg   1440
gccgtgttag gccaagttgt tgtttgtttg tcagcatcca gtcattcagt gtgcttgtgc   1500
tgcaccaatt atcaggtaca cctgacattg tctagcgtgg ggcacttgca aataatgaaa   1560
tggacaaaat catgctagaa catgagctgt cgtgttcaac ttcctgtagc ttggtctcat   1620
ctgagctcac caacccagct tgcatctgca gtaatttgca agacctcgtg tgcatttcag   1680
cttctgaacc tcatgttgct tgcaggggcg ccagggagac gacgccgtgc agcctgatct   1740
acagctcgga gacgatgagc acccccgggt cggcgaccgg ggcccgcaac cattcccgcc   1800
gcagggcgca gacgccggtc tgccgctacg tcccgagctc gctcgagatg gacgagttct   1860
tcgccgccgc ggagcagcag caacaccaga ccttcaggga gaagtaagaa ctctgcctcc   1920
tcctaccacc atcatttaaa catgctcact gaagatcaag cttcttgttc atacaattgt   1980
tctaacactc gctgcttcat tctaatcagg tacaacttct gtcccgcgag cgagcgcccg   2040
ctcccccggac ggtacgagtg gacggtgctg gactgctagg gcttcttcat acctcacatc   2100
accaccacca ccaggagctc ctccattgat ctctgtaaca ccagaatgac caccaccatc   2160
agcagcagca gcagcatgtc atatgccgtg ggcgcgatgc aaatgcagta gcgttaggtt   2220
tctgattcac ctgttgtaaa aacttagagt tagcccgcag tcagcagtag ctcagccagc   2280
cagccatctc tcagcctgat ccccaacctc actgtaaccg tcgttagtta acaacatctc   2340
atttccgtag gctctagctt gattagcagc tcggttatct tctgtatccc ggtcctccat   2400
caatgaatga atcanagcta gatttatttt                                    2430
```

<210> SEQ ID NO 77
<211> LENGTH: 615
<212> TYPE: DNA
<213> ORGANISM: Triticum aestivum

<400> SEQUENCE: 77

```
atggggaagt acatgcgtaa gagcaaggcc tcgggggagg tggccgtcat ggaggtcgcc     60
ggcgcgctgc tcggcgtccg cacccgctcc cgcaccctcg ccgcgcagca gcagcgcgct    120
```

```
ccgtcccctt cgccgcagcg caagggccac gaggacggcg actacctcga gctcaggagc    180

aggaggctcg agaagcagcc gccgccgggg cccaaggaca aggaggacgc gccgcagccg    240

ccggccgccg gtgggagggg gatggagtcg ttcgcggccg aggggttcga ggccgacctc    300

gaggtctcct tcggcgacaa cgtgctggac tgggacgcca ccgacagggg cgccagggag    360

acgacgccgt gcagcctgat ctacagctcg gagacgatga gcacccccgg gtcggcgacc    420

ggggcccgca accattcccg ccgcagggcg cagacgccgg tctgccgcta cgtcccgagc    480

tcgctcgaga tggacgagtt cttcgccgcc gcggagcagc agcaacacca gaccttcagg    540

gagaagtaca acttctgtcc cgcgagcgag cgcccgctcc ccggacggta cgagtggacg    600

gtgctggact gctag                                                     615
```

```
<210> SEQ ID NO 78
<211> LENGTH: 204
<212> TYPE: PRT
<213> ORGANISM: Triticum aestivum

<400> SEQUENCE: 78

Met Gly Lys Tyr Met Arg Lys Ser Lys Ala Ser Gly Glu Val Ala Val
1               5                   10                  15

Met Glu Val Ala Gly Ala Leu Leu Gly Val Arg Thr Arg Ser Arg Thr
            20                  25                  30

Leu Ala Ala Gln Gln Gln Arg Ala Pro Ser Pro Ser Pro Gln Arg Lys
        35                  40                  45

Gly His Glu Asp Gly Asp Tyr Leu Glu Leu Arg Ser Arg Arg Leu Glu
    50                  55                  60

Lys Gln Pro Pro Pro Gly Pro Lys Asp Lys Glu Asp Ala Pro Gln Pro
65                  70                  75                  80

Pro Ala Ala Gly Gly Arg Gly Met Glu Ser Phe Ala Ala Glu Gly Phe
                85                  90                  95

Glu Ala Asp Leu Glu Val Ser Phe Gly Asp Asn Val Leu Asp Trp Asp
            100                 105                 110

Ala Thr Asp Arg Gly Ala Arg Glu Thr Thr Pro Cys Ser Leu Ile Tyr
        115                 120                 125

Ser Ser Glu Thr Met Ser Thr Pro Gly Ser Ala Thr Gly Ala Arg Asn
    130                 135                 140

His Ser Arg Arg Arg Ala Gln Thr Pro Val Cys Arg Tyr Val Pro Ser
145                 150                 155                 160

Ser Leu Glu Met Asp Glu Phe Phe Ala Ala Ala Glu Gln Gln Gln His
                165                 170                 175

Gln Thr Phe Arg Glu Lys Tyr Asn Phe Cys Pro Ala Ser Glu Arg Pro
            180                 185                 190

Leu Pro Gly Arg Tyr Glu Trp Thr Val Leu Asp Cys
        195                 200


<210> SEQ ID NO 79
<211> LENGTH: 249
<212> TYPE: PRT
<213> ORGANISM: Oryza sativa

<400> SEQUENCE: 79

Met Gly Lys Lys Lys Lys Arg Asp Gly Ala Ala Ala Arg Arg Gln Ala
1               5                   10                  15

Arg Val Val Val Gly Gly Val Arg Thr Arg Ala Ala Val Thr Ala Arg
            20                  25                  30
```

```
Arg Val Val Ala Ser Ala Glu Glu Gly Cys Gly Leu Val Gly Arg Gly
        35                  40                  45

Gly Gly Gly Gly Ser Gly Gly Asp Asp Gly Glu Gly Gly Cys Tyr Leu
    50                  55                  60

Arg Leu Arg Ser Arg Arg Leu Pro Phe Val Ala Ala Ala Val Val Ser
65                  70                  75                  80

Ser Arg Arg Glu Glu Ala Leu Gly Asp Ser Val Ala Glu Ala Ala Ser
                85                  90                  95

Ser Ser Ser Ser Arg Ala Val Glu Leu Leu Gly Cys Ser Gly Glu Glu
            100                 105                 110

Glu Ala Met Ala Glu Lys Val Cys Thr Gln Ala Gly Glu Asp His Asp
        115                 120                 125

Glu Glu Ser Ser Val Gly Asp Ser Gly Cys Gly Arg Glu Arg Ser Ala
    130                 135                 140

Thr Thr Pro Ser Ser Arg Arg Pro Pro Gly Asp Ala Asp Ser Ser Asp
145                 150                 155                 160

Ala Glu Ser Asn Gln Glu Ala Lys Gln Gln Met Cys Arg Arg Ser Ser
                165                 170                 175

Thr Thr Ser Ala Ala Ala Phe His Ala Gly Ala Thr Thr Arg Ser Phe
            180                 185                 190

Arg Met Met Ala Pro Pro Ala Ala Ala Ala Glu Ile Glu Glu Phe Leu
        195                 200                 205

Ala Ala Ala Glu Arg Ser Glu Ala Glu Arg Phe Ala Ala Lys Tyr Asn
    210                 215                 220

Phe Asp Val Val Arg Gly Val Pro Leu Asp Ala Gly Gly Ala Gly Arg
225                 230                 235                 240

Phe Glu Trp Thr Ala Val Gly Ser Gly
                245
```

<210> SEQ ID NO 80
<211> LENGTH: 214
<212> TYPE: PRT
<213> ORGANISM: Oryza sativa

<400> SEQUENCE: 80

```
Met Gly Lys Tyr Leu Arg Ser Ser Cys Lys Gln Gln Gln Gln Pro Ser
1               5                   10                  15

Ser Pro Ala Ala Val Ala Ser Val Ala Ala Ala Ala Val Ser Ser Tyr
            20                  25                  30

Ser Tyr Leu Thr Leu Arg Ser Gly Arg Arg Val Pro Ala Ala Ala Ala
        35                  40                  45

Ala Ala Gly Gly Ser Ala Cys Arg Arg Arg His Arg Arg Gly Gly Arg
    50                  55                  60

Arg Gly Cys Ala Lys Asn Gly Ala Gly Ser Ala Arg Ala Cys Gly Ala
65                  70                  75                  80

Arg Ser Pro Thr Ser Ser Ala Ser Ser Gly Gln Arg Arg Arg Cys Glu
                85                  90                  95

Ala Val Glu Cys Ser His Gly Gly Gly Arg Ala Glu Leu Ser Arg Ser
            100                 105                 110

Pro Pro Leu Gly Asn Ser Val Val Val Val Ser Gly Asp Val Val Ser
        115                 120                 125

Gly Glu Arg Lys Ser Leu Lys Pro Asn Ser Cys Ser Arg Glu Val Ala
    130                 135                 140

Ala Glu His Ala Gly Glu His Lys His Asn Pro Ala Ala Ala Ala Ala
```

```
145                 150                 155                 160

Ala Gly Arg Arg Pro Pro Leu Ser Pro Pro Glu Ala Glu Ile Glu Ala
                165                 170                 175

Phe Phe Ala Ala Ala Glu Leu Ala Glu Arg Arg Arg Phe Ala Glu Lys
            180                 185                 190

Tyr Asn Tyr Asp Ile Ala Leu Asp Arg Pro Leu Gln Gly Arg Tyr Glu
        195                 200                 205

Trp Glu Pro Val Ser Thr
    210


<210> SEQ ID NO 81
<211> LENGTH: 194
<212> TYPE: PRT
<213> ORGANISM: Oryza sativa

<400> SEQUENCE: 81

Met Gly Lys Tyr Met Arg Lys Ala Lys Val Val Val Ser Gly Glu Val
1               5                   10                  15

Val Ala Ala Ala Val Met Glu Leu Ala Ala Ala Pro Leu Gly Val Arg
            20                  25                  30

Thr Arg Ala Arg Ser Leu Ala Leu Gln Lys Arg Gln Gly Gly Glu Tyr
        35                  40                  45

Leu Glu Leu Arg Ser Arg Arg Leu Glu Lys Leu Pro Pro Pro Pro Pro
    50                  55                  60

Pro Pro Pro Arg Arg Arg Ala Thr Ala Ala Ala Ala Thr Ala Asp Ala
65                  70                  75                  80

Thr Ala Ala Glu Ser Ala Glu Ala Glu Val Ser Phe Gly Gly Glu Asn
                85                  90                  95

Val Leu Glu Leu Glu Ala Met Glu Arg Asn Thr Arg Glu Thr Thr Pro
            100                 105                 110

Cys Ser Leu Ile Arg Asp Pro Asp Thr Ile Ser Thr Pro Gly Ser Thr
        115                 120                 125

Thr Arg Arg Ser His Ser Ser Ser His Cys Lys Val Gln Thr Pro Val
    130                 135                 140

Arg His Asn Ile Ile Pro Ala Ser Ala Glu Leu Glu Ala Phe Phe Ala
145                 150                 155                 160

Ala Glu Glu Gln Arg Gln Arg Gln Ala Phe Ile Asp Lys Tyr Asn Phe
                165                 170                 175

Asp Pro Val Asn Asp Cys Pro Leu Pro Gly Arg Phe Glu Trp Val Lys
            180                 185                 190

Leu Asp


<210> SEQ ID NO 82
<211> LENGTH: 221
<212> TYPE: PRT
<213> ORGANISM: Oryza sativa

<400> SEQUENCE: 82

Met Gly Lys Tyr Met Arg Lys Gly Lys Val Ser Gly Glu Val Ala Val
1               5                   10                  15

Met Glu Val Gly Gly Ala Leu Leu Gly Val Arg Thr Arg Ser Arg Thr
            20                  25                  30

Leu Ala Leu Gln Arg Thr Thr Ser Ser Gln Lys Pro Pro Glu Lys Gly
        35                  40                  45

Glu Gly Asp Pro Gly Ala Gly Ala Gly Ala Gly Ala Glu Tyr Leu Glu
    50                  55                  60
```

```
Leu Arg Ser Arg Arg Leu Glu Lys Pro Pro Pro His Thr Pro Pro Ala
65                  70                  75                  80

Lys Glu Lys Glu Thr Ala Arg Arg Ala Ser Ala Ala Ala Ala Ala Ala
                85                  90                  95

Val Arg Met Pro Ala Ala Pro Gln Ala Ala Glu Glu Phe Glu Ala Glu
            100                 105                 110

Val Glu Val Ser Phe Gly Asp Asn Val Leu Asp Leu Asp Gly Asp Ala
        115                 120                 125

Met Glu Arg Ser Thr Arg Glu Thr Thr Pro Cys Ser Leu Ile Arg Ser
    130                 135                 140

Ser Glu Met Ile Ser Thr Pro Gly Ser Thr Thr Lys Thr Asn Thr Ser
145                 150                 155                 160

Ile Ser Ser Arg Arg Arg Met Glu Thr Ser Val Cys Arg Tyr Val Pro
                165                 170                 175

Ser Ser Leu Glu Met Glu Glu Phe Phe Ala Ala Ala Glu Gln Gln Gln
            180                 185                 190

His Gln Ala Phe Arg Glu Arg Tyr Asn Phe Cys Pro Val Asn Asp Cys
        195                 200                 205

Pro Leu Pro Gly Arg Tyr Glu Trp Thr Arg Leu Asp Cys
    210                 215                 220


<210> SEQ ID NO 83
<211> LENGTH: 190
<212> TYPE: PRT
<213> ORGANISM: Zea mays

<400> SEQUENCE: 83

Met Gly Lys Tyr Met Arg Lys Ala Lys Ala Ser Ser Glu Val Val Ile
1               5                   10                  15

Met Asp Val Ala Ala Ala Pro Leu Gly Val Arg Thr Arg Ala Arg Ala
            20                  25                  30

Leu Ala Leu Gln Arg Leu Gln Glu Gln Gln Thr Gln Trp Glu Glu Gly
        35                  40                  45

Ala Gly Gly Glu Tyr Leu Glu Leu Arg Asn Arg Arg Leu Glu Lys Leu
    50                  55                  60

Pro Pro Pro Pro Ala Thr Thr Arg Arg Ser Gly Gly Arg Lys Ala Ala
65                  70                  75                  80

Ala Glu Ala Ala Ala Thr Lys Glu Ala Glu Ala Ser Tyr Gly Glu Asn
                85                  90                  95

Met Leu Glu Leu Glu Ala Met Glu Arg Ile Thr Arg Glu Thr Thr Pro
            100                 105                 110

Cys Ser Leu Ile Asn Thr Gln Met Thr Ser Thr Pro Gly Ser Thr Arg
        115                 120                 125

Ser Ser His Ser Cys His Arg Arg Val Asn Ala Pro Pro Val His Ala
    130                 135                 140

Val Pro Ser Ser Arg Glu Met Asn Glu Tyr Phe Ala Ala Glu Gln Arg
145                 150                 155                 160

Arg Gln Gln Gln Asp Phe Ile Asp Lys Tyr Asn Phe Asp Pro Ala Asn
                165                 170                 175

Asp Cys Pro Leu Pro Gly Arg Phe Glu Trp Val Lys Leu Asp
            180                 185                 190


<210> SEQ ID NO 84
<211> LENGTH: 256
<212> TYPE: PRT
```

<213> ORGANISM: Zea mays

<400> SEQUENCE: 84

Met Gly Lys Tyr Met Arg Lys Cys Arg Gly Ala Ala Gly Ala Glu Val
1               5                   10                  15

Ala Ala Val Glu Val Thr Gln Val Val Gly Val Arg Thr Arg Ser Arg
            20                  25                  30

Ser Ala Ala Ala Thr Gly Gly Val Ala Lys Val Ala Pro Arg Arg Lys
        35                  40                  45

Arg Ala Pro Ala Gly Glu Pro Ala Ala Ala Val Ser Ala Gly Gly Asp
    50                  55                  60

Gly Gly Ser Cys Tyr Ile His Leu Arg Ser Arg Met Leu Phe Met Ala
65                  70                  75                  80

Pro Pro Gln Pro Gln Pro Ser Val Asp Ser Val Pro Thr Pro Val Glu
                85                  90                  95

Ala Ala Asp Gly Ala Ala Gly Gln Gln Gly Ala Ala Leu Ala Ala Gly
            100                 105                 110

Leu Ser Arg Cys Ser Ser Thr Ala Ser Ser Val Asn Leu Gly Leu Gly
        115                 120                 125

Gly Gln Arg Gly Ser His Thr Cys Arg Ser Tyr Asp Ala Ala Glu Ala
    130                 135                 140

Gly Gly Asp His Val Leu Val Asp Val Ser Ala Ala Ser Asn Ser Gly
145                 150                 155                 160

Ser Gly Pro Asp Arg Glu Arg Arg Glu Thr Thr Pro Ser Ser Arg Ala
                165                 170                 175

His Gly Glu Leu Ser Asp Leu Glu Ser Asp Leu Ala Gly His Lys Thr
            180                 185                 190

Gly Pro Ser Leu Pro Ala Ala Thr Pro Ala Ala Glu Leu Ile Val Pro
        195                 200                 205

Pro Ala His Glu Ile Gln Glu Phe Phe Ala Ala Ala Glu Ala Ala Gln
    210                 215                 220

Ala Lys Arg Phe Ala Ser Lys Tyr Asn Phe Asp Phe Val Arg Gly Val
225                 230                 235                 240

Pro Leu Asp Ala Gly Gly Arg Phe Glu Trp Ala Pro Val Val Ser Ile
                245                 250                 255

<210> SEQ ID NO 85
<211> LENGTH: 253
<212> TYPE: PRT
<213> ORGANISM: Zea mays
<220> FEATURE:
<221> NAME/KEY: misc_feature
<222> LOCATION: (150)..(150)
<223> OTHER INFORMATION: Xaa can be any naturally occurring amino acid

<400> SEQUENCE: 85

Met Gly Lys Tyr Met Arg Lys Cys Arg Gly Ala Ala Gly Ala Glu Val
1               5                   10                  15

Ala Thr Val Glu Val Thr Gln Val Val Gly Val Arg Thr Arg Ser Arg
            20                  25                  30

Ser Ala Ala Ala Thr Gly Gly Val Ala Lys Val Val Ala Pro Arg Arg
        35                  40                  45

Asn Arg Ala Pro Ala Gly Glu Pro Ala Ala Ser Val Gly Ala Gly Gly
    50                  55                  60

Asp Gly Gly Ser Cys Tyr Ile His Leu Arg Ser Arg Met Leu Phe Met
65                  70                  75                  80

```
Ala Pro Pro Gln Pro Gln Pro Pro Ser Val Pro Thr Pro Ala Glu Ala
                85                  90                  95

Ala Asp Gly Ala Ala Gly Gln Gln Gly Ala Ala Leu Ala Ala Gly Leu
            100                 105                 110

Ser Arg Cys Ser Ser Thr Ala Ser Ser Val His Val Gly Gly Gln Arg
        115                 120                 125

Gly Ser His Thr Cys Arg Ser Asp Asp Ala Ala Glu Ala Gly Gly Asp
    130                 135                 140

His Val Leu Val Val Xaa Val Ser Ala Ser Asn Ser Gly Ser Gly Pro
145                 150                 155                 160

Asp Arg Glu Arg Arg Glu Thr Thr Pro Ser Ser Arg Ala His Gly Glu
                165                 170                 175

Leu Ser Asp Leu Glu Ser Asp Leu Ala Gly His Lys Thr Gly Pro Ser
            180                 185                 190

Leu Pro Ala Ala Thr Pro Ala Ala Glu Leu Ile Val Pro Pro Ala His
        195                 200                 205

Glu Ile Gln Glu Phe Phe Ala Ala Ala Glu Ala Ala Gln Ala Lys Arg
    210                 215                 220

Phe Ala Ser Lys Tyr Asn Phe Asp Phe Val Arg Gly Val Pro Leu Asp
225                 230                 235                 240

Ala Gly Gly Arg Phe Glu Trp Ala Pro Val Val Ser Ile
                245                 250
```

<210> SEQ ID NO 86
<211> LENGTH: 238
<212> TYPE: PRT
<213> ORGANISM: Zea mays

<400> SEQUENCE: 86

```
Val Ala Ala Val Glu Val Thr Gln Val Val Gly Val Arg Thr Arg Ser
1               5                   10                  15

Arg Ser Ala Ala Ala Thr Gly Gly Val Ala Lys Val Val Ala Pro Arg
            20                  25                  30

Arg Lys Arg Ala Pro Ala Gly Glu Pro Ala Ala Ser Val Gly Ala Gly
        35                  40                  45

Gly Asp Gly Gly Ser Cys Tyr Ile His Leu Arg Ser Arg Met Leu Phe
    50                  55                  60

Met Ala Pro Pro Gln Pro Gln Pro Pro Ser Val Pro Thr Pro Ala Glu
65                  70                  75                  80

Ala Ala Asp Gly Ala Ala Gly Gln Gln Gly Ala Ala Leu Ala Ala Gly
                85                  90                  95

Leu Ser Arg Cys Ser Ser Thr Ala Ser Ser Val His Val Gly Gly Gln
            100                 105                 110

Arg Gly Ser His Thr Cys Arg Ser Asp Asp Ala Ala Glu Ala Gly Gly
        115                 120                 125

Asp His Val Leu Val Asp Val Ser Ala Ala Ser Asn Ser Gly Ser Gly
    130                 135                 140

Pro Asp Arg Glu Arg Arg Glu Thr Thr Pro Ser Ser Arg Ala His Gly
145                 150                 155                 160

Glu Leu Ser Asp Leu Glu Ser Asp Leu Ala Gly His Lys Thr Gly Pro
                165                 170                 175

Ser Leu Pro Ala Ala Thr Pro Ala Ala Glu Leu Ile Val Pro Pro Ala
            180                 185                 190

His Glu Ile Gln Glu Phe Phe Ala Ala Ala Glu Ala Ala Gln Ala Lys
        195                 200                 205
```

-continued

```
Arg Phe Ala Ser Lys Tyr Asn Phe Asp Phe Val Arg Gly Val Pro Leu
    210                 215                 220

Asp Ala Gly Gly Arg Phe Glu Trp Ala Pro Val Val Ser Ile
225                 230                 235


<210> SEQ ID NO 87
<211> LENGTH: 232
<212> TYPE: PRT
<213> ORGANISM: Zea mays

<400> SEQUENCE: 87

Met Gly Lys Tyr Met Arg Lys Arg Arg Gly Ala Ala Gly Glu Gly Val
1               5                   10                  15

Ala Ala Val Glu Val Ser Gln Val Val Gly Val Arg Thr Arg Ser Arg
            20                  25                  30

Ser Ala Ala Ala Thr Gly Gly Gly Val Ala Lys Val Ala Pro Pro Arg
        35                  40                  45

Arg Lys Lys Ala Leu Leu Pro Ala Ala Asn Glu Thr Ala Ser Gly Glu
    50                  55                  60

Pro Gly Ala Val Gly Gly Gly Gly Gly Asp Gly Gly Ser Cys Cys Tyr
65                  70                  75                  80

Ile His Leu Arg Ser Arg Met Leu Phe Met Ala Ala Pro Gln Gln Gln
                85                  90                  95

Pro Ser Ala Ala Pro Thr Pro Ala Glu Ala Ala Gly Ala Ala Gln Gln
            100                 105                 110

Gly Gly Val Val Ala Leu Ala Ala Gly Leu Ser Arg Cys Ser Ser Thr
        115                 120                 125

Ala Ser Thr Val Asp Val Gly Gly Gln Gln Pro Ala Ser Gly Ser His
    130                 135                 140

Ala Cys Arg Ser Asp Ala Ala Glu Val Ala Gly Asp His Val Pro Asp
145                 150                 155                 160

Val Val Thr Ala Ser Asn Ser Gly Ser Val Pro Asp Arg Glu Arg Arg
                165                 170                 175

Glu Thr Thr Pro Ser Ser Ser Arg Ala His Gly Gly Glu Leu Ser Asp
            180                 185                 190

Leu Glu Ser Asp Leu Val Gly Trp Gln Lys Thr Gly Cys Ser Ser Ser
        195                 200                 205

Pro Ala Thr Thr Thr Ser Ala Ala Glu Leu Ile Val Pro Pro Ala Gln
    210                 215                 220

Glu Ile Gln Glu Phe Phe Ala Ala
225                 230
```

IDENTIFICATION AND USE OF KRP MUTANTS IN WHEAT

CROSS-REFERENCE TO RELATED APPLICATIONS

This application is a continuation of U.S. patent application Ser. No. 13/444,305, filed Apr. 11, 2012, which claims the benefit of U.S. Provisional Patent Application Ser. No. 61/474,203, filed Apr. 11, 2011, each of which is hereby incorporated by reference in its entirety for all purposes.

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is TARG-016_02US_ST25.txt. The text file is about 97 KB, was created on Jun. 24, 2015, and is being submitted electronically via EFS-Web.

TECHNICAL FIELD

The invention generally relates to identifying and using compositions and methods for improving the agronomic characteristics of wheat, such as by increasing wheat yield. More specifically, the present invention relates to compositions and methods for improving one or more agronomic characteristics of wheat by identifying and using one or more mutant Kinase Inhibitor Protein (KIP) Related Proteins (KRP).

BACKGROUND

The most important trait as a target for crop improvement is yield. Efforts to improve crop yields by developing new plant varieties can be divided into two approaches. One is to reduce crop yield losses by breeding or engineering crop varieties with increased resistance to abiotic stress conditions such as drought, cold, or salt or to biotic stress conditions resulting from pests or disease-causing pathogens. While this approach has value, it does not provide fundamentally improved crop yield in the absence of stress conditions and in fact, such resistance may direct plant resources that otherwise would be available for increased yield in the plant. The second approach is to breed or engineer new crop varieties in which the basic yield capacity is increased.

Classical breeding programs have initially produced substantial gains in improved yield in a variety of crops. A commonly experienced pattern though has been substantial gains in yield initially followed by incremental further improvements that become smaller and more difficult to obtain. More recently developed approaches based on molecular biology technologies have in principle offered the potential to achieve substantial improvement in crop yield by altering the timing, location, or level of expression of plant genes or heterologous genes that play a role in plant growth and/or development. Substantial progress has been made over the past twenty years in identifying plant genes and or heterologous genes that have a role in plant growth and/or development. Despite these gains in using molecular approaches, there continues to be a large unmet need for improved agronomic and horticultural plants produced through more conventional plant breeding. Because of the complexity of plant growth regulation and how it relates in the end to yield traits, it is still not obvious which, if any, of particular genes would be clear candidates to improve crop yield through either plant breeding and/or molecular techniques.

KRP proteins belong to a class of cell cycle inhibitors that bind to and inhibit cyclin/CDK kinase complexes. Mutation of conserved residues within KRP family members are expected to modify KRP's ability to function as an inhibitor of cyclin-CDK kinase complexes. Specifically, some mutations in KRP genes would lead to expression of a nonfunctional KRP cell cycle inhibitor or a cell cycle inhibitor with reduced activity. This loss of or reduced cyclin/CDK kinase inhibitory activity would lead to increased cyclin-CDK kinase activity in cells when normally these cells would have reduced cyclin-CDK activity. This loss of or reduced cyclin/CDK kinase inhibitory activity would lead to increased cell divisions in tissue where the normal wild-type KRP version is expressed. This increased cell division would result in positive agronomic traits such as increased yield, increased seed size, larger plants, larger leaves, larger roots etc. For background on KRP-related technologies, see, for example, WO/2007/016319 and US20070056058, each of which is incorporated by reference in its entirety for all purposes. The present invention identifies new KRP genes and proteins in wheat as well as providing methods for their use in producing improved wheat plants through conventional plant breeding and/or molecular methodologies.

SUMMARY OF INVENTION

The present invention provides a plant comprising in its genome one or more disrupted KRP genes. The present invention in another aspect provides a plant cell, plant part, or tissue culture derived from the plants of the present invention.

The present invention provides mutants in KRP genes, for example, KRP1, KRP2, KRP4, KRP5, including but not limited to those as listed in Tables 2 to 3.

In another aspect, the present invention provides methods for increasing weight, size, and/or number of one or more organs in a plant. The organ can be any part of a plant, for example, organs that contribute to yield in a plant. In some embodiments, the organ is seed, leaf, branch, root, shoot, stigma, ovule, pollen, seed pods, seed heads, or tiller. In some embodiments, said methods comprise disturbing one or more KRPs in the plant. In some embodiments, methods for increasing seed weight, seed size, seed number and/or yield in a plant are provided. In one embodiment, the plant is a monocotyledon plant. In some embodiments, the plant can be a monocotyledon plant selected from the Triticeae tribe, for example, wheat. Methods of disrupting a gene function include but are not limited to mutagenesis (e.g., chemical mutagenesis, radiation mutagenesis, transposon mutagenesis, insertional mutagenesis, signature tagged mutagenesis, site-directed mutagenesis, and natural mutagenesis), antisense, knock-outs, and/or RNA interference.

In some embodiments, mutations described in the Tables 2 and 3 can be integrated into species closely related to the plants in the Triticeae tribe, or plants closely related to wheat. In some embodiments, amino acids in conserved domains or sites compared to KRP orthologs in other species can be substituted or deleted to make mutants with reduced or abolished activity, mutants that lead to loss-of-function (e.g., protein instability), and/or mutants that lead to gain-of-function (e.g., more stable or more active protein). In some embodiments, one or more KRPs in a wheat plant are knocked down or knocked out by one or more methods available to one skilled in the art.

In some embodiments, in a tetraploid wheat plant, one or two copies of a KRP gene are disrupted (e.g., KRP1A, KRP1B; KRP2A, KRP2B; KRP4A, KRP4B; and KRP5A, KRP5B); in a hexaploid wheat plant, one or more copies of one, two, or three copies of a KRP gene are disrupted (e.g., KRP1A, KRP1B, KRP1D; KRP2A, KRP2B, KRP2D; KRP4A, KRP4B, KRP4D; and KRP5A, KRP5B, KRP5D).

In another aspect, the present invention provides methods of producing a plant having increased weight, size, and/or number of one or more organs, for example, a plant with increased seed size, seed number, and/or seed yield compared to a wild type reference plant. Such methods comprising utilizing mutations in the KRP genes as described herein.

The present invention also provides a plant having increased seed size, seed number, and/or seed yield compared to a wild type reference plant, wherein the plant has one or more mutations in one or more KRP genes. In some embodiments, said plant is a monocot plant. In some embodiments, said monocot plant is a plant from the Triticeae tribe. In some embodiments, said plant is wheat.

The present invention further provides a seed, a fruit, a plant cell or a plant part of the transgenic plants as described herein. For example, the present invention provides a pollen of the plant, an ovule of the plant, a genetically related plant population comprising the plant, a tissue culture of regenerable cells of the plant. In some embodiments, the regenerable cells are derived from embryos, protoplasts, meristematic cells, callus, pollen, leaves, anthers, stems, petioles, roots, root tips, fruits, seeds, flowers, cotyledons, and/or hypocotyls.

The present invention also provides methods of breeding a crop species having improved agronomic and horticultural characteristics, such as new plant types having increased weight, size, and/or number of one or more organs, for example, a plant with increased seed size, seed number, seed weight and/or seed yield compared to a wild type reference plant.

In some embodiments, such methods comprise making a cross between a *Triticum* sp. mutant with one or more mutations listed in Tables 2 and 3 with a second *Triticum* sp. to produce an F1 plant, or with a species in the Triticeae tribe which can intercross with said *Triticum* sp. The method may further comprise backcrossing the F1 plant to the second *Triticum* sp. or species in the Triticeae tribe; and repeating the backcrossing step to generate an near isogenic line, wherein the one or more mutations are integrated into the genome of said second *Triticum* sp. or the species in the Triticeae tribe; wherein the near isogenic line derived from the second *Triticum* sp. or the species in the Triticeae tribe with the integrated mutations has altered weight, size, and/or number of one or more organs, for example, altered seed weight, seed size, seed number, and/or seed yield. Optionally, such methods can be facilitated by molecular markers or TILLING®.

The present invention also provides methods of decreasing the activity of one or more KRP proteins in a plant cell, plant part, tissue culture or whole plant comprising contacting the plant cell, plant part, tissue culture or whole plant with an inhibitory nucleic acid having complementarity to a gene encoding said KRP protein. In some embodiments, the plant is a plant from the Triticeae tribe. In some embodiments, said plant is wheat.

The present invention provides isolated wheat KRPs, including by way of example, KRP1A, KRP1B, KRP1D, KRP2A, KRP2B, KRP2D, KRP4B, KRP4D, KRP5A, KRP5D, and mutations in these genes. Based on our findings, it appears that hexaploid wheat has been naturally selected to have what appear to be knock-out mutations in KRP4A and KRP5B. This was discovered during the course of TILLING®. For KRP4A, the gene appears to be completely missing from the hexaploid wheat genome, although it is still present in the tetraploid genome. For KRP5B, there appears to be one missing nucleotide in the gene, which would shift the translational frame and produce a predicted truncation of a few amino acids further on.

The present invention provides an isolated nucleic acid sequence comprising a sequence selected from the group consisting of SEQ ID NOs: 40, 41, 43, 44, 46, 47, 49, 50, 52, 53, 55, 56, 58, 59, 60, 62, 63, 64, 66, 67, 68, 70, 71, 73, 74, 76 and 77, and fragments and variations derived from thereof, which encode a KRP gene.

In one embodiment, the present invention provides an isolated polynucleotide encoding plant KRP protein, comprising a nucleic acid sequence that shares at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to SEQ ID NOs: 40, 41, 43, 44, 46, 47, 49, 50, 52, 53, 55, 56, 58, 59, 60, 62, 63, 64, 66, 67, 68, 70, 71, 73, 74, 76 and 77.

The present invention further provides an isolated amino acid sequence (e.g., a peptide, polypeptide and the like) comprising a sequence selected from the group consisting of SEQ ID NOs: 42, 45, 48, 51, 54, 57, 61, 65, 69, 72, 75, and 78 and fragments and variations derived from thereof, which form a KRP protein.

In some embodiments, the present invention provides an isolated amino acid sequence which forms a protein that shares an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to SEQ ID NOs: 42, 45, 48, 51, 54, 57, 61, 65, 69, 72, 75, and 78.

In one embodiment, isolated polynucleotides of the present invention comprise a sequence selected from the group consisting of: (a) sequences recited in SEQ ID NOs: 40, 41, 43, 44, 46, 47, 49, 50, 52, 53, 55, 56, 58, 59, 60, 62, 63, 64, 66, 67, 68, 70, 71, 73, 74, 76 and 77, or portions thereof; (b) complements of the sequences recited in SEQ ID NOs: 40, 41, 43, 44, 46, 47, 49, 50, 52, 53, 55, 56, 58, 59, 60, 62, 63, 64, 66, 67, 68, 70, 71, 73, 74, 76 and 77, or portions thereof; (c) reverse complements of the sequences recited in SEQ ID NOs: 40, 41, 43, 44, 46, 47, 49, 50, 52, 53, 55, 56, 58, 59, 60, 62, 63, 64, 66, 67, 68, 70, 71, 73, 74, 76 and 77, or portions thereof; (d) reverse sequences of the sequences recited in SEQ ID NOs: 40, 41, 43, 44, 46, 47, 49, 50, 52, 53, 55, 56, 58, 59, 60, 62, 63, 64, 66, 67, 68, 70, 71, 73, 74, 76 and 77, or portions thereof; and (e) sequences having at least 50%, 75%, 90%, 95% or 98% identity, as defined herein, to a sequence of (a)-(d) or a specified region of a sequence of (a)-(d).

The present invention also provides a chimeric gene comprising the isolated nucleic acid sequence of any one of the polynucleotides described above operably linked to suitable regulatory sequences.

The present invention also provides recombinant constructs comprising the chimeric gene as described above.

The present invention further provides interfering RNA (RNAi) constructs based on nucleic acid sequences of the present invention. In some embodiments, the RNAi constructs are can be transformed into a wheat plant to down-regulate one or more KRPs. The RNAi construct can be, but is not limited to antisense oligonucleotide construct, double-strand oligonucleotide construct, siRNA construct, or inverted repeat construct. In some embodiment, the RNAi constructs comprise a plant promoter, such as a constitutive promoter, an inducible promoter, or a tissue-specific promoter. In some embodiments, the promoter is embryonic specific or seed specific.

BRIEF DESCRIPTION OF THE DRAWINGS

FIG. 3A, expression in young seeds from three developmental stages. Lanes 1-3: 2-6 days after anthesis (pools 1, 2 and 3). Lanes 4-6: 8-12 days after anthesis (pools 1, 2 and 3). Lanes 7-8: 14-18 days after anthesis (pools 1 and 2). FIG. 3B, expression in indicated tissues. Actin served as an internal transcript control.

SEQUENCES

Figure 1:
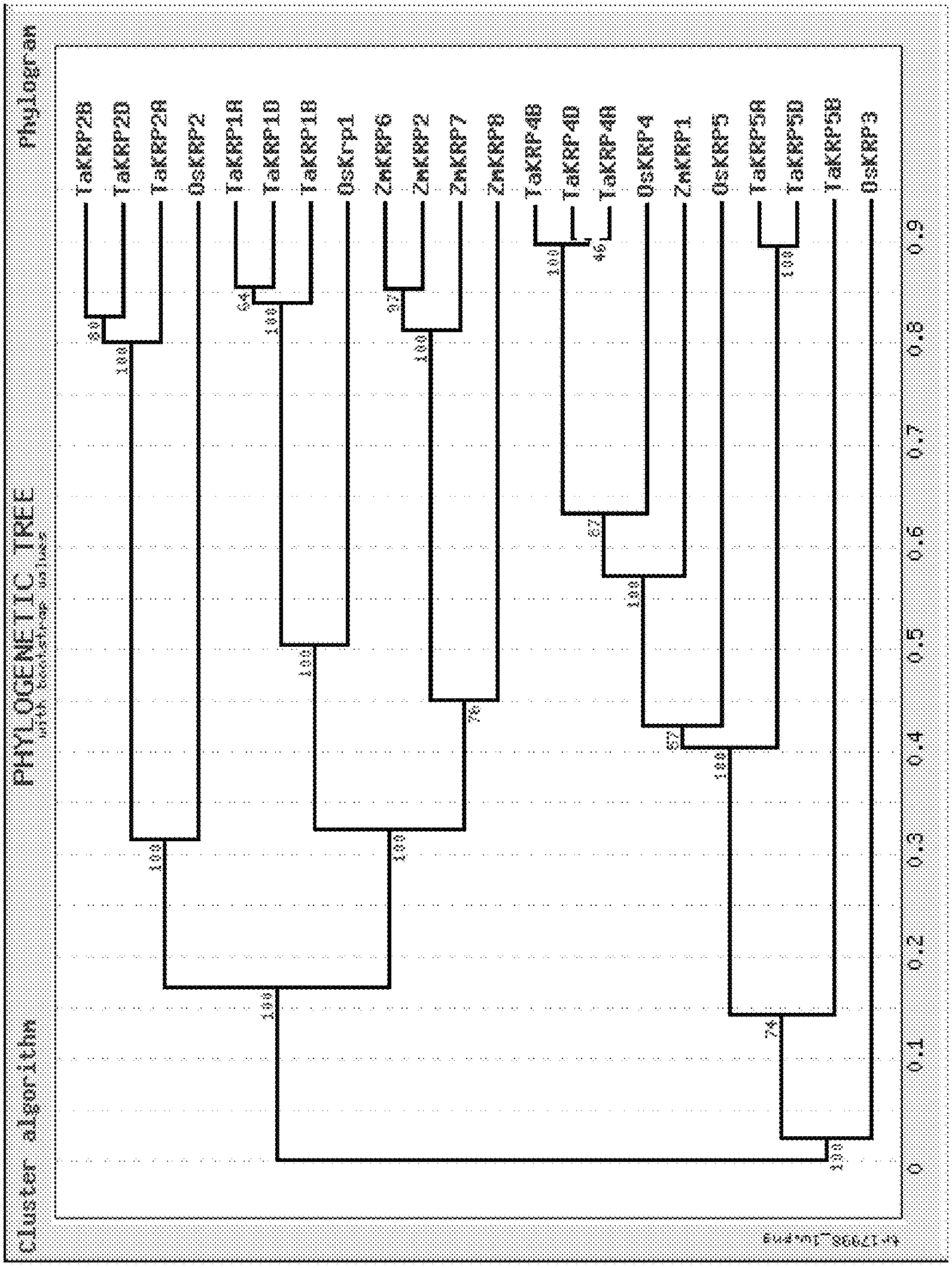
FIG. 1 depicts a phylogenetic tree of rice (Os), corn (Zm) and wheat (Ta) KRPs.

Sequence listings for SEQ ID No: 1-SEQ ID No: 87 are part of this application and are incorporated by reference herein. Sequence listings are provided at the end of this document.

DETAILED DESCRIPTION

All publications, patents and patent applications, including any drawings and appendices, and all nucleic acid sequences and polypeptide sequences identified by GenBank Accession numbers, herein are incorporated by reference to the same extent as if each individual publication or patent application was specifically and individually indicated to be incorporated by reference.

The following description includes information that may be useful in understanding the present invention. It is not an admission that any of the information provided herein is prior art or relevant to the presently claimed inventions, or that any publication specifically or implicitly referenced is prior art.

Definitions

As used herein, the verb "comprise" as is used in this description and in the claims and its conjugations are used in its non-limiting sense to mean that items following the word are included, but items not specifically mentioned are not excluded.

As used herein, the term "plant" refers to any living organism belonging to the kingdom Plantae (i.e., any genus/species in the Plant Kingdom). This includes familiar organisms such as but not limited to trees, herbs, bushes, grasses, vines, ferns, mosses and green algae. The term refers to both monocotyledonous plants, also called monocots, and dicotyledonous plants, also called dicots. Examples of particular plants include but are not limited to plants in the Triticeae tribe (e.g., plants in the *Triticum* genus), plants in the tribe of Oryzeae (e.g., plants in *Oryza* genus), plants in the Andropogoneae tribe (e.g., plants in the *Zea* genus, such has corn). Other non-limiting examples of plant include, potatoes, roses, apple trees, sunflowers, bananas, tomatoes, opo, pumpkins, squash, lettuce, cabbage, oak trees, guzmania, geraniums, hibiscus, *clematis*, poinsettias, sugarcane, taro, duck weed, pine trees, Kentucky blue grass, *zoysia*, coconut trees, *brassica* leafy vegetables (e.g. broccoli, broccoli raab, Brussels sprouts, cabbage, Chinese cabbage (Bok Choy and Napa), cauliflower, cavalo, collards, kale, kohlrabi, mustard greens, rape greens, and other *brassica* leafy vegetable crops), bulb vegetables (e.g. garlic, leek, onion (dry bulb, green, and Welch), shallot, and other bulb—vegetable crops), citrus fruits (e.g. grapefruit, lemon, lime, orange, tangerine, citrus hybrids, pummelo, and other citrus fruit crops), cucurbit vegetables (e.g. cucumber, citron melon, edible gourds, gherkin, muskmelons (including hybrids and/or cultivars of *cucumis* melons), water-melon, cantaloupe, and other cucurbit vegetable crops), fruiting vegetables (including eggplant, ground cherry, pepino, pepper, tomato, tomatillo, and other fruiting vegetable crops), grape, leafy vegetables (e.g. romaine), root/tuber and corm vegetables (e.g. potato), and tree nuts (almond, pecan, pistachio, and walnut), berries (e.g., tomatoes, barberries, currants, elderberries, gooseberries, honeysuckles, mayapples, nannyberries, Oregon-grapes, see-buckthorns, hackberries, bearberries, lingonberries, strawberries, sea grapes, lackberries, cloudberries, loganberries, raspberries, salmonberries, thimbleberries, and wineberries), cereal crops (e.g., corn, rice, wheat, barley, sorghum, millets, oats, ryes, triticales, buckwheats, fonio, *quinoa*, oil palm), pome fruit (e.g., apples, pears), stone fruits (e.g., coffees, jujubes, mangos, olives, coconuts, oil palms, pistachios, almonds, apricots, cherries, damsons, nectarines, peaches and plums), vine (e.g., table grapes, wine grapes), fiber crops (e.g. hemp, cotton), ornamentals, and the like.

As used herein, the term "plant part" refers to any part of a plant including but not limited to the shoot, root, stem, seeds, stipules, leaves, petals, flowers, ovules, bracts, branches, petioles, internodes, bark, pubescence, tillers, rhizomes, fronds, blades, pollen, stamen, and the like. The two main parts of plants grown in some sort of media, such as soil, are often referred to as the "above-ground" part, also often referred to as the "shoots", and the "below-ground" part, also often referred to as the "roots".

The term "a" or "an" refers to one or more of that entity; for example, "a gene" refers to one or more genes or at least one gene. As such, the terms "a" (or "an"), "one or more" and "at least one" are used interchangeably herein. In addition, reference to "an element" by the indefinite article "a" or "an" does not exclude the possibility that more than one of the elements are present, unless the context clearly requires that there is one and only one of the elements.

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the terms "polypeptide," "peptide," and "protein" are used interchangeably herein to refer to polymers of amino acids of any length. These terms also include proteins that are post-translationally modified through reactions that include glycosylation, acetylation and phosphorylation.

As used herein, the term "homologous" or "homologue" or "ortholog" is known in the art and refers to related sequences that share a common ancestor or family member and are determined based on the degree of sequence identity. The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences. These terms describe the relationship between a gene found in one species, subspecies, variety, cultivar or strain and the corresponding or equivalent gene in another species, subspecies, variety, cultivar or strain. For purposes of this invention homologous sequences are compared. "Homologous sequences" or "homologues" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. The degree of sequence identity may vary, but in one embodiment, is at least 50% (when using standard sequence alignment programs known in the art), at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in *Current Protocols in Molecular Biology* (F. M. Ausubel et al., eds., 1987) Supplement 30, section 7.718, Table 7.71. Some alignment programs are MacVector (Oxford Molecular Ltd, Oxford, U.K.), ALIGN Plus (Scientific and Educational Software, Pennsylvania) and AlignX (Vector NTI, Invitrogen, Carlsbad, Calif.). Another alignment program is Sequencher (Gene Codes, Ann Arbor, Mich.), using default parameters.

As used herein, the term "nucleotide change" refers to, e.g., nucleotide substitution, deletion, and/or insertion, as is well understood in the art. For example, mutations contain alterations that produce silent substitutions, additions, or deletions, but do not alter the properties or activities of the encoded protein or how the proteins are made.

As used herein, the term "protein modification" refers to, e.g., amino acid substitution, amino acid modification, deletion, and/or insertion, as is well understood in the art, As used herein, the term "derived from" refers to the origin or source, and may include naturally occurring, recombinant, unpurified, or purified molecules. A nucleic acid or an amino acid derived from an origin or source may have all kinds of nucleotide changes or protein modification as defined elsewhere herein.

As used herein, the term "at least a portion" or "fragment" of a nucleic acid or polypeptide means a portion having the minimal size characteristics of such sequences, or any larger fragment of the full length molecule, up to and including the full length molecule. For example, a portion of a nucleic acid may be 12 nucleotides, 13 nucleotides, 14 nucleotides, 15 nucleotides, 16 nucleotides, 17 nucleotides, 18 nucleotides, 19 nucleotides, 20 nucleotides, 22 nucleotides, 24 nucleotides, 26 nucleotides, 28 nucleotides, 30 nucleotides, 32 nucleotides, 34 nucleotides, 36 nucleotides, 38 nucleotides, 40 nucleotides, 45 nucleotides, 50 nucleotides, 55 nucleotides, and so on, going up to the full length nucleic acid. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as hybridization probe may be as short as 12 nucleotides; in one embodiment, it is 20 nucleotides. A portion of a polypeptide useful as an epitope may be as short as 4 amino acids. A portion of a polypeptide that performs the function of the full-length polypeptide would generally be longer than 4 amino acids.

As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988).

As used herein, the term "substantially complementary" means that two nucleic acid sequences have at least about 65%, preferably about 70% or 75%, more preferably about 80% or 85%, even more preferably 90% or 95%, and most preferably about 98% or 99%, sequence complementarities to each other. This means that primers and probes must exhibit sufficient complementarity to their template and target nucleic acid, respectively, to hybridize under stringent conditions. Therefore, the primer and probe sequences need not reflect the exact complementary sequence of the binding region on the template and degenerate primers can be used. For example, a non-complementary nucleotide fragment may be attached to the 5'-end of the primer, with the remainder of the primer sequence being complementary to the strand. Alternatively, non-complementary bases or longer sequences can be interspersed into the primer, provided that the primer has sufficient complementarity with the sequence of one of the strands to be amplified to hybridize therewith, and to thereby form a duplex structure which can be extended by polymerizing means. The non-complementary nucleotide sequences of the primers may include restriction enzyme sites. Appending a restriction enzyme site to the end(s) of the target sequence would be particularly helpful for cloning of the target sequence. A substantially complementary primer sequence is one that has sufficient sequence complementarity to the amplification template to result in primer binding and second-strand synthesis. The skilled person is familiar with the requirements of primers to have sufficient sequence complementarity to the amplification template.

As used herein, the terms “polynucleotide”, “polynucleotide sequence”, “nucleic acid sequence”, “nucleic acid fragment”, and “isolated nucleic acid fragment” are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: “A” for adenylate or deoxyadenylate (for RNA or DNA, respectively), “C” for cytidylate or deoxycytidylate, “G” for guanylate or deoxyguanylate, “U” for uridylate, “T” for deoxythymidylate, “R” for purines (A or G), “Y” for pyrimidines (C or T), “K” for G or T, “H” for A or C or T, “I” for inosine, and “N” for any nucleotide.

As used herein, the phrase “a biologically active variant” or “functional variant” with respect to a protein refers to an amino acid sequence that is altered by one or more amino acids with respect to a reference sequence, while still maintains substantial biological activity of the reference sequence. The variant can have “conservative” changes, wherein a substituted amino acid has similar structural or chemical properties, e.g., replacement of leucine with isoleucine. Alternatively, a variant can have “nonconservative” changes, e.g., replacement of a glycine with a tryptophan. Analogous minor variations can also include amino acid deletion or insertion, or both. Guidance in determining which amino acid residues can be substituted, inserted, or deleted without eliminating biological or immunological activity can be found using computer programs well known in the art, for example, DNASTAR software.

The term “primer” as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T vs. G/C content) of primer. A pair of bi-directional primers consists of one forward and one reverse primer as commonly used in the art of DNA amplification such as in PCR amplification.

The terms “stringency” or “stringent hybridization conditions” refer to hybridization conditions that affect the stability of hybrids, e.g., temperature, salt concentration, pH, formamide concentration and the like. These conditions are empirically optimized to maximize specific binding and minimize non-specific binding of primer or probe to its target nucleic acid sequence. The terms as used include reference to conditions under which a probe or primer will hybridize to its target sequence, to a detectably greater degree than other sequences (e.g. at least 2-fold over background). Stringent conditions are sequence dependent and will be different in different circumstances. Longer sequences hybridize specifically at higher temperatures. Generally, stringent conditions are selected to be about 5° C. lower than the thermal melting point (Tm) for the specific sequence at a defined ionic strength and pH. The Tm is the temperature (under defined ionic strength and pH) at which 50% of a complementary target sequence hybridizes to a perfectly matched probe or primer. Typically, stringent conditions will be those in which the salt concentration is less than about 1.0 M $Na^+$ ion, typically about 0.01 to 1.0 M Na+ ion concentration (or other salts) at pH 7.0 to 8.3 and the temperature is at least about 30° C. for short probes or primers (e.g. 10 to 50 nucleotides) and at least about 60° C. for long probes or primers (e.g. greater than 50 nucleotides). Stringent conditions may also be achieved with the addition of destabilizing agents such as formamide. Exemplary low stringent conditions or “conditions of reduced stringency” include hybridization with a buffer solution of 30% formamide, 1 M NaCl, 1% SDS at 37° C. and a wash in 2×SSC at 40° C. Exemplary high stringency conditions include hybridization in 50% formamide, 1M NaCl, 1% SDS at 37° C., and a wash in 0.1×SSC at 60° C. Hybridization procedures are well known in the art and are described by e.g. Ausubel et al., 1998 and Sambrook-et al., 2001.

As used herein, “coding sequence” refers to a DNA sequence that codes for a specific amino acid sequence. “Regulatory sequences” refer to nucleotide sequences located upstream (5' non-coding sequences), within, or downstream (3' non-coding sequences) of a coding sequence, and which influence the transcription, RNA processing or stability, or translation of the associated coding sequence.

As used herein, “regulatory sequences” may include, but are not limited to, promoters, translation leader sequences, introns, and polyadenylation recognition sequences.

As used herein, “promoter” refers to a DNA sequence capable of controlling the expression of a coding sequence or functional RNA. The promoter sequence consists of proximal and more distal upstream elements, the latter elements often referred to as enhancers. Accordingly, an “enhancer” is a DNA sequence that can stimulate promoter activity, and may be an innate element of the promoter or a heterologous element inserted to enhance the level or tissue specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely, defined, DNA fragments of some variation may have identical promoter activity.

As used herein, a “plant promoter” is a promoter capable of initiating transcription in plant cells whether or not its origin is a plant cell, e.g. it is well known that *Agrobacterium* promoters are functional in plant cells. Thus, plant promoters include promoter DNA obtained from plants, plant viruses and bacteria such as *Agrobacterium* and *Bra-*

*dyrhizobium* bacteria. A plant promoter can be a constitutive promoter or a non-constitutive promoter.

As used herein, a "constitutive promoter" is a promoter which is active under most conditions and/or during most development stages. There are several advantages to using constitutive promoters in expression vectors used in plant biotechnology, such as: high level of production of proteins used to select transgenic cells or plants; high level of expression of reporter proteins or scorable markers, allowing easy detection and quantification; high level of production of a transcription factor that is part of a regulatory transcription system; production of compounds that requires ubiquitous activity in the plant; and production of compounds that are required during all stages of plant development. Non-limiting exemplary constitutive promoters include, CaMV 35S promoter, opine promoters, ubiquitin promoter, actin promoter, alcohol dehydrogenase promoter, etc.

As used herein, a "non-constitutive promoter" is a promoter which is active under certain conditions, in certain types of cells, and/or during certain development stages. For example, tissue specific, tissue preferred, cell type specific, cell type preferred, inducible promoters, and promoters under development control are non-constitutive promoters. Examples of promoters under developmental control include promoters that preferentially initiate transcription in certain tissues, such as stems, leaves, roots, or seeds.

As used herein, "inducible" or "repressible" promoter is a promoter which is under chemical or environmental factors control. Examples of environmental conditions that may effect transcription by inducible promoters include anaerobic conditions, or certain chemicals, or the presence of light.

As used herein, a "tissue specific" promoter is a promoter that initiates transcription only in certain tissues. Unlike constitutive expression of genes, tissue-specific expression is the result of several interacting levels of gene regulation. As such, in the art sometimes it is preferable to use promoters from homologous or closely related plant species to achieve efficient and reliable expression of transgenes in particular tissues. This is one of the main reasons for the large amount of tissue-specific promoters isolated from particular plants and tissues found in both scientific and patent literature. Non-limiting tissue specific promoters include, beta-amylase gene or barley hordein gene promoters (for seed gene expression), tomato pz7 and pz130 gene promoters (for ovary gene expression), tobacco RD2 gene promoter (for root gene expression), banana TRX promoter and melon actin promoter (for fruit gene expression), and embryo specific promoters, e.g., a promoter associated with an amino acid permease gene (AAPl), an oleate 12-hydroxylase:desaturase gene from *Lesquerella fendleri* (LFAH 12), an 2S2 albumin gene (2S2), a fatty acid elongase gene (FAEI), or a leafy cotyledon gene (LEC2).

As used herein, a "tissue preferred" promoter is a promoter that initiates transcription mostly, but not necessarily entirely or solely in certain tissues.

As used herein, a "cell type specific" promoter is a promoter that primarily drives expression in certain cell types in one or more organs, for example, vascular cells in roots, leaves, stalk cells, and stem cells.

As used herein, a "cell type preferred" promoter is a promoter that primarily drives expression mostly, but not necessarily entirely or solely in certain cell types in one or more organs, for example, vascular cells in roots, leaves, stalk cells, and stem cells.

As used herein, the "3' non-coding sequences" or "3' untranslated regions" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. (1989) Plant Cell 1:671-680.

As used herein, "RNA transcript" refers to the product resulting from RNA polymerase-catalyzed transcription of a DNA sequence. When the RNA transcript is a perfect complementary copy of the DNA sequence, it is referred to as the primary transcript. An RNA transcript is referred to as the mature RNA when it is an RNA sequence derived from post-transcriptional processing of the primary transcript. "Messenger RNA (mRNA)" refers to the RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

As used herein, the term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

As used herein, the term "recombinant" refers to an artificial combination of two otherwise separated segments of sequence, e.g., by chemical synthesis or by the manipulation of isolated segments of nucleic acids by genetic engineering techniques.

As used herein, the phrases "recombinant construct", "expression construct", "chimeric construct", "construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chtomosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating.

The term "expression", as used herein, refers to the production of a functional end-product e.g., an mRNA or a protein (precursor or mature).

As used herein, the phrase "plant selectable or screenable marker" refers to a genetic marker functional in a plant cell. A selectable marker allows cells containing and expressing that marker to grow under conditions unfavorable to growth of cells not expressing that marker. A screenable marker facilitates identification of cells which express that marker.

As used herein, the term "inbred", "inbred plant" is used in the context of the present invention. This also includes any single gene conversions of that inbred. The term single allele converted plant as used herein refers to those plants which are developed by a plant breeding technique called backcrossing wherein essentially all of the desired morphological and physiological characteristics of an inbred are recovered in addition to the single allele transferred into the inbred via the backcrossing technique.

As used herein, the term "sample" includes a sample from a plant, a plant part, a plant cell, or from a transmission vector, or a soil, water or air sample.

As used herein, the term "offspring" refers to any plant resulting as progeny from a vegetative or sexual reproduction from one or more parent plants or descendants thereof. For instance an offspring plant may be obtained by cloning or selfing of a parent plant or by crossing two parent plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

As used herein, the term "cross", "crossing", "cross pollination" or "cross-breeding" refer to the process by which the pollen of one flower on one plant is applied (artificially or naturally) to the ovule (stigma) of a flower on another plant.

As used herein, the term "cultivar" refers to a variety, strain or race of plant that has been produced by horticultural or agronomic techniques and is not normally found in wild populations.

As used herein, the terms "dicotyledon" and "dicot" refer to a flowering plant having an embryo containing two seed halves or cotyledons. Dicotyledon plants at least include the Eudicot, Magnoliid, Amborella, Nymphaeales, Austrobaileyales, Chloranthales, and Ceratophyllum groups. Eudicots include these clades: Ranunculales, sabiales, Proteales, Trochodendrales, Buxales, and Core Eudicots (e.g., Berberidopsidales, Dilleniales, Gunnerales, Caryophyllales, Santalales, Saxifragales, Vitales, Rosids and Asterids). Non-limiting examples of dicotyledon plants include tobacco, tomato, pea, alfalfa, clover, bean, soybean, peanut, members of the Brassicaceae family (e.g., camelina, Canola, oilseed rape, etc.), amaranth, sunflower, sugarbeet, cotton, oaks, maples, roses, mints, squashes, daisies, nuts; cacti, violets and buttercups.

As used herein, the term "monocotyledon" or "monocot" refer to any of a subclass (Monocotyledoneae) of flowering plants having an embryo containing only one seed leaf and usually having parallel-veined, leaves, flower parts in multiples of three, and no secondary growth in stems and roots. Non-limiting examples of monocotyledon plants include lilies, orchids, corn, rice, wheat, barley, sorghum, millets, oats, ryes, triticales, buckwheats, fonio, *quinoa*, grasses, such as tall fescue, goat grass, and Kentucky bluegrass; grains, such as wheat, oats and barley, irises, onions, palms.

As used herein, the term "gene" refers to any segment of DNA associated with a biological function. Thus, genes include, but are not limited to, coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "genotype" refers to the genetic makeup of an individual cell, cell culture, tissue, organism (e.g., a plant), or group of organisms.

As used herein, the term "hemizygous" refers to a cell, tissue or organism in which a gene is present only once in a genotype, as a gene in a haploid cell or organism, a sex-linked gene in the heterogametic sex, or a gene in a segment of chromosome in a diploid cell or organism where its partner segment has been deleted.

As used herein, the terms "heterologous polynucleotide" or a "heterologous nucleic acid" or an "exogenous DNA segment" refer to a polynucleotide, nucleic acid or DNA segment that originates from a source foreign to the particular host cell, or, if from the same source, is modified from its original form. Thus, a heterologous gene in a host cell includes a gene that is endogenous to the particular host cell, but has been modified. Thus, the terms refer to a DNA segment which is foreign or heterologous to the cell, or homologous to the cell but in a position within the host cell nucleic acid in which the element is not ordinarily found. Exogenous DNA segments are expressed to yield exogenous polypeptides.

As used herein, the term "heterologous trait" refers to a phenotype imparted to a transformed host cell or transgenic organism by an exogenous DNA segment, heterologous polynucleotide or heterologous nucleic acid.

As used herein, the term "heterozygote" refers to a diploid or polyploid individual cell or plant having different alleles (forms of a given gene) present at least at one locus.

As used herein, the term "heterozygous" refers to the presence of different alleles (forms of a given gene) at a particular gene locus.

As used herein, the terms "homolog" or "homologue" refer to a nucleic acid or peptide sequence which has a common origin and functions similarly to a nucleic acid or peptide sequence from another species.

As used herein, the term "homozygote" refers to an individual cell or plant having the same alleles at one or more or all loci. When the term is used with reference to a specific locus or gene, it means at least that locus or gene has the same alleles.

As used herein, the terms "homozygous" or "HOMO" refer to the presence of identical alleles at one or more or all loci in homologous chromosomal segments. When the terms are used with reference to a specific locus or gene, it means at least that locus or gene has the same alleles.

As used herein, the term "hybrid" refers to any individual cell, tissue or plant resulting from a cross between parents that differ in one or more genes.

As used herein, the term "inbred" or "inbred line" refers to a relatively true-breeding strain.

As used herein, the term "line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selfing). In this context, the term "pedigree" denotes the lineage of a plant, e.g. in terms of the sexual crosses affected such that a gene or a combination of genes, in heterozygous (hemizygous) or homozygous condition, imparts a desired trait to the plant.

As used herein, the terms "mutant" or "mutation" refer to a gene, cell, or organism with an abnormal genetic constitution that may result in a variant phenotype.

As used herein, the term "open pollination" refers to a plant population that is freely exposed to some gene flow, as opposed to a closed one in which there is an effective barrier to gene flow.

As used herein, the terms "open-pollinated population" or "open-pollinated variety" refer to plants normally capable of at least some cross-fertilization, selected to a standard, that may show variation but that also have one or more genotypic or phenotypic characteristics by which, the population or the variety can be differentiated from others. A hybrid, which has no barriers to cross-pollination, is an open-pollinated population or an open-pollinated variety.

As used herein when discussing plants, the term "ovule" refers to the female gametophyte, whereas the term "pollen" means the male gametophyte.

As used herein, the term "phenotype" refers to the observable characters of an individual cell, cell culture, organism (e.g., a plant), or group of organisms which results from the interaction between that individual's genetic makeup (i.e., genotype) and the environment.

As used herein, the term "plant tissue" refers to any part of a plant. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpet, sepal, anther, ovule, pedicel, needle, cone, rhizome, stolon, shoot, pericarp, endosperm, placenta, berry, stamen, and leaf sheath.

As used herein, the term "self-crossing", "self pollinated" or "self-pollination" means the pollen of one flower on one plant is applied (artificially or naturally) to the ovule (stigma) of the same or a different flower on the same plant.

As used herein, the term "transformation" refers to the transfer of nucleic acid (i.e., a nucleotide polymer) into a cell. As used herein, the term "genetic transformation" refers to the transfer and incorporation of DNA, especially recombinant DNA, into a cell.

As used herein, the term "transformant" refers to a cell, tissue or organism that has undergone transformation. The original transformant is designated as "T0" or "$T_0$." Selfing the T0 produces a first transformed generation designated as "T1" or "$T_1$."

As used herein, the term "transgene" refers to a nucleic acid that is inserted into an organism, host cell or vector in a manner that ensures its function.

As used herein, the term "transgenic" refers to cells, cell cultures, organisms (e.g., plants), and progeny which have received a foreign or modified gene by one of the various methods of transformation, wherein the foreign or modified gene is from the same or different species than the species of the organism receiving the foreign or modified gene.

As used herein, the term "transposition event" refers to the movement of a transposon from a donor site to a target site.

As used herein, the term "variety" refers to a subdivision of a species, consisting of a group of individuals within the species that are distinct in form or function from other similar arrays of individuals.

As used herein, the term "vector", "plasmid", or "construct" refers broadly to any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744-12746).

As used herein, the phrase "seed size" refers to the volume of the seed material itself, which is the space occupied by the constituents of the seed.

As used herein, the phrase "seed number" refers to the average number of seeds produced from each fruit, each plant, or each predetermined area (e.g., 1 acre).

As used herein, the phrase "Test Weight" or "Grain Test Weight" is a determination of bulk density (mass/volume), measured for commerce under specific conditions defined in the U.S. by the USDA-FGIS. Test weight is a general indicator of grain quality and higher test weight normally means higher quality grain. Grain test weight in units of pounds per bushel specifies the weight of a "volume" bushel, which is 32 quarts (30,283 cubic centimeters) of grain. When grain is traded, samples are usually tested for quality, and test weight is one of the tests carried out. Test weights have been a part of U.S. grain grades since the United States Grain Standards Act was passed by Congress in 1916. U.S. grades for most grains specify test weight minimums for each grade level. For instance, the official minimum allowable test weight in the U.S. for No. 1 yellow corn is 56 lbs/bu and for No. 2 yellow corn is 54 lbs/bu (USDA-GIPSA, 1996). By law, a "weight" bushel of corn is exactly 56 pounds, a soybean bushel is 60 pounds, and a wheat bushel is 60 pounds, regardless of the test weight. The "weight" bushel is used for the basis of payment for grain, but price discounts are often tied to shipments of lower grade grain possessing low test weight.

As used herein, the phrase "Grain Apparent Density" refers to grain density determined in a fashion wherein the bulk density (mass/volume) of cereal seed is sometimes measured with the aid of a gas pycnometer, which typically uses helium and measures the volume of the sample. Grain kernels contain internal void spaces and intercellular spaces and are not completely porous to helium. Since the gas cannot reach all internal spaces, the volume of material comprising the kernel can be overestimated with gas pycnometry and a density lower than the "true density" of grain material is determined (Chang, C S (1988) Cereal Chem: 65:13-15).

As used herein, the phrase "Grain True Density" refers to the bulk density of grain, expressed as the quotient of mass divided by volume, whereby all void space not comprising solid materials of the seed has been eliminated before, or discounted in, determination of the volume used in the calculation (Chang, C S (1988) Cereal Chem:65:13-15).

As used herein, the term "cyclin dependent kinase inhibitor" (also referred to herein as "CDK inhibitor" or "CKI") refers to a class of proteins that negatively regulate cyclin dependent kinases (CDKs). CKIs amenable to the present invention are those having separate polypeptide regions capable of independently binding a cyclin and a CDK. Such CKIs include, for example, identified families of plant CKIs (the seven identified *Arabidopsis* CKIs), having homology to Kinase Inhibitor Proteins (KIPs) in animals, referred to as KIP-related proteins (KRPs) (also known as Inhibitors of "CDKs," or "ICKs").

The term "naturally occurring," in the context of CKI polypeptides and nucleic acids, means a polypeptide or nucleic acid having an amino acid or nucleotide sequence that is found in nature, i.e., an amino acid or nucleotide sequence that can be isolated from a source in nature (an organism) and which has not been intentionally modified by human intervention. As used herein, laboratory strains of plants which may have been selectively bred according to classical genetics are considered naturally-occurring plants.

As used herein, "wild-type CKI gene" or "wild-type CKI nucleic acid" refers to a sequence of nucleic acid, corresponding to a CKI genetic locus in the genome of an organism, that encodes a gene product performing the normal function of the CKI protein encoded by a naturally-occurring nucleotide sequence corresponding to the genetic locus. A genetic locus can have more than one sequence or allele in a population of individuals, and the term "wild-type" encompasses all such naturally-occurring alleles that encode a gene product performing the normal function. "Wild-type" also encompasses gene sequences that are not necessarily naturally occurring, but that still encode a gene product with normal function (e.g., genes having silent mutations or encoding proteins with conservative substitutions).

As used herein, the term "wild-type CKI polypeptide" or "wild-type CKI protein" refers to a CKI polypeptide encoded by a wild-type gene. A genetic locus can have more than one sequence or allele in a population of individuals, and the term "wild-type" encompasses all such naturally-occurring alleles that encode a gene product performing the normal function.

Breeding Methods

Classic breeding methods can be included in the present invention to introduce one or more recombinant KRPs of the present invention into other plant varieties, or other close-related species that are compatible to be crossed with the transgenic plant of the present invention.

Open-Pollinated Populations. The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes to flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988).

Mass Selection. In mass selection, desirable individual plants are chosen, harvested, and the seed composited without progeny testing to produce the following generation. Since selection is based on the maternal parent only, and there is no control over pollination, mass selection amounts to a form of random mating with selection. As stated herein, the purpose of mass selection is to increase the proportion of superior genotypes in the population.

Synthetics. A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (*Vicia*) or clones, as in herbage grasses, clovers and alfalfa, makes no difference in principle. Parents are selected on general combining ability, sometimes by test crosses or topcrosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enter a synthetic varies widely. In practice, numbers of parental lines range from 10 to several hundred, with 100-200 being the average. Broad based synthetics formed from 100 or more clones would be expected to be more stable during seed multiplication than narrow based synthetics.

Pedigreed Varieties. A pedigreed variety is a superior genotype developed from selection of individual plants out of a segregating population followed by propagation and seed increase of self pollinated offspring and careful testing of the genotype over several generations. This is an open pollinated method that works well with naturally self pollinating species. This method can be used in combination with mass selection in variety development. Variations in pedigree and mass selection in combination are the most common methods for generating varieties in self pollinated crops.

Hybrids. A hybrid is an individual plant resulting from a cross between parents of differing genotypes. Commercial hybrids are now used extensively in many crops, including con (maize), sorghum, sugarbeet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

The production of hybrids is a well-developed industry, involving the isolated production of both the parental lines and the hybrids which result from crossing those lines. For a detailed discussion of the hybrid production process, see, e.g., Wright, *Commercial Hybrid Seed Production* 8:161-176, In Hybridization of Crop Plants.

Targeting Induced Local Lesions in Genomes (TILLING®)

TILLING® (Targeting Induced Local Lesions in Genomes) is a method in molecular biology that allows directed identification of mutations in a specific gene. TILLING® was introduced in 2000, using the model plant *Arabidopsis thaliana*. TILLING® has since been used as a reverse genetics method in other organisms such as zebrafish, corn, wheat, rice, soybean, tomato and lettuce.

The method combines a standard and efficient technique of mutagenesis with a chemical mutagen (e.g., Ethyl methanesulfonate (EMS)) with a sensitive DNA screening-technique that identifies single base mutations (also called point mutations) in a target gene. EcoTILLING is a method that uses TILLING® techniques to look for natural mutations in individuals, usually for population genetics analysis. See Comai, et al., 2003, Efficient discovery of DNA polymorphisms in natural populations by EcoTILLING. The Plant Journal 37, 778-786. Gilchrist et al. 2006. Use of EcoTILLING as an efficient SNP discovery tool to survey genetic variation in wild populations of *Populus trichocarpa*. Mol. Ecol. 15, 1367-1378. Mejlhede et al. 2006. EcoTILLING for the identification of allelic variation within the powdery mildew resistance genes mlo and Mla of barley. Plant Breeding 125, 461-467. Nieto et al. 2007, EcoTILLING for the identification of allelic variants of melon eIF4E, a factor that controls virus susceptibility. BMC Plant Biology 7, 34-42, each of which is incorporated by reference hereby for all purposes. DEcoTILLING is a modification of TILLING® and EcoTILLING which uses an inexpensive method to identify fragments (Garvin et al., 2007, DEco-TILLING: An inexpensive method for SNP discovery that reduces ascertainment bias. Molecular Ecology Notes 7, 735-746).

The TILLING® method relies on the formation of heteroduplexes that are formed when multiple alleles (which could be from a heterozygote, or a pool of multiple homozygotes and heterozygotes) are amplified in a PCR, heated, and then slowly cooled. A "bubble" forms at the mismatch of the two DNA strands (the induced mutation in TILLING® or the natural mutation or SNP in EcoTILLING), which is then cleaved by single stranded nucleases. The products are then separated by size on several different platforms.

Several TILLING® centers exists over the world that focus on agriculturally important species: UC Davis (USA), focusing on Rice; Purdue University (USA), focusing on Maize; University of British Columbia (CA), focusing on *Brassica napus*; John Innes Centre (UK), focusing on *Brassica rapa*; Fred Hutchinson Cancer Research, focusing on *Arabidopsis*; Southern Illinois University (USA), focusing on Soybean; John Innes Centre (UK), focusing on Lotus and *Medicago*; and INRA (France), focusing on Pea and Tomato.

More detailed description on methods and compositions on TILLING® can be found in references Nos. 1-35b, U.S. Pat. No. 5,994,075, US 2004/0053236 A1, WO 2005/055704, and WO 2005/048692, each of which is hereby incorporated by reference for all purposes.

The inventors used TILLING® in both tetraploid (4×) wheat (containing A and B genomes) and hexaploid (6×) wheat (containing A, B and D genomes) for the following wheat KRP genes: KRP1, KRP2. KRP4 and KRP5. The numbering of the KRPs in wheat does not necessarily correspond to the numbering of the KRPs in *Arabidopsis* (e.g. wheat KRP1 is not necessarily equivalent to *Arabidopsis* KRP1).

Triticeae Tribe

Intense use of wild Triticeae can be seen in the Levant as early as 23,000 years ago. Triticeae is a tribe within the Pooideae subfamily of grasses that includes genera with many domesticated species. Major crop genera are found in this tribe including wheat (See Wheat taxonomy), barley, and rye; crops in other genera include some for human consumption and others used for animal feed or rangeland protection. Among the world's cultivated species, this tribe has some of the most complex genetic histories. An example is bread wheat, which contains the genomes of three species, only one of them originally a wheat *Triticum* species.

Genera in the Triticeae tribe include, but are not limited to, *Aegilops* (goat grasses—jointed goatgrass, Tausch goatgrass, etc.); *Agropyron* (crested wheatgrasses—Desert wheatgrass, quackgrass, etc.); *Amblyopyrum* (Slim wheat grass—*amblyopyrum*, etc.); *Australopyrum* (Australian wheatgrasses—velvet wheatgrass, pectinated wheatgrass, etc.); *Cockaynea* (See *Stenostachys; Cockaynea* is a younger, and hence invalid, name for *Stenostachys*, etc.); *Crithopsis* (delileana grass etc.); *Dasypyrum* (Mosquito grass; etc.); *Elymus* (*Elymus* (wild ryes—blue wildrye, Texas ryegrass, etc.); *Elytrigia; Eremium* (Argentine desert ryegrass, etc.); *Eremopyrum* (false wheatgrasses—tapertip false wheatgrass, annual wheatgrass, etc.); *Festucopsis; Haynaldia; Henrardia; Heteranthelium; Hordelymus; Hordeum* (barleys—common barley, foxtail barley, etc.); *Hystrix* (porcupine grass—bottlebrush grass, etc.); *Kengyilia; Leymus* (wild rye—American dune grass, lyme grass, etc.); *Lophopyrum* (tall wheatgrass); *Malacurus Pascopyrum* (western wheatgrass etc.); *Peridictyon; Psathyrostachys* (Russian wildrye, etc.); *Pseudoroegneria* (bluebunch wheatgrasses—beardless wheatgrass, etc.); *Secale* (Ryes—Cereal rye, Himalayan Rye, etc.); *Sitanion; Stenostachys* (New Zealand wheatgrasses, etc); *Taeniatherum* (medusahead etc.); *Thinopyrum* (intermediate wheatgrass, Russian wheatgrass, thick quackgrass, etc.); *Triticum* (Wheats—common wheat, *durum* wheat, etc.).

Triticeae and its sister tribe Bromeae (possible cultivars: *Bromus mango* S. America) when joined form a sister *clade* with Poeae and Aveneae (oats). Inter-generic gene flow characterized these taxa from the early stages. For example, Poeae and Aveneae share a genetic marker with barley and 10 other members of Triticeae, whereas all 19 genera of Triticeae bear a wheat marker along with Bromeae. Genera within Triticeae contain diploid, allotetraploid and/or allohexaploid genomes, the capacity to form allopolyploid genomes varies within the tribe. In this tribe, the majority of diploid species tested are closely related to *Aegilops*, the more distal members (earliest branch points) include *Hordeum* (Barley), Eremian, *Psathyrostachys*.

Many genera and species of Triticeae are exemplary of allopolyploids, having more chromosomes than seen in typical diploids. Typically allopolyploids are tetraploid or hexaploid, AABB or AABBDD. The creation of polyploid species results from natural random events tolerated by polyploid capable plants. Likewise natural allopolyploid plants may have selective benefits and may allow the recombination of distantly related genetic material facilitating at a later time a reversion back to diploid. Poulard wheat is an example of a stable allotetraploid wheat.

*Aegilops* appears to be basal to several taxa such as *Triticum, Ambylopyrum*, and *Crithopsis*. Certain species such as *Aegilops speltoides* could potentially represent core variants of the taxa. The generic placement may be more a matter of nomenclature. *Aegilops* and *Triticum* genera are very closely related; the *Aegilops* species occupy most of the basal branch points in bread wheat evolution indicating that *Triticum* genus evolved from *Aegilops* after an estimated 4 million years ago. The divergence of the genomes is followed by allotetraploidation of a speltoid goatgrass x basal wheat species *Triticum boeoticum* with strains in the middle eastern region giving rise to cultivated *emmer* wheat.

*Triticum* spp.

*Triticum* sp. is a grass cultivated worldwide. In 2007 world production of wheat was 607 million tons, making it the third most-produced cereal after maize (784 million tons) and rice (651 million tons). Globally, wheat is the leading source of vegetable protein in human food, having a higher protein content than either maize (corn) or rice, the other major cereals. In terms of total production tonnages used for food, it is currently second to rice as the main human food.

Wheat is planted to a limited extent as a forage crop for livestock, and its straw can be used as a construction material for roofing thatch. The husk of the grain, separated when milling white flour, is bran. Wheat germ is the embryo portion of the wheat kernel. It is a concentrated source of vitamins, minerals, and protein, and is sustained by the larger, starch storage region of the kernel—the endosperm.

Non-limiting examples of *Triticum* species include, *T. aestivum* (e.g., common wheat, or bread wheat, a.k.a. *Triticum aestivum* L. subsp. *Aestivum*; Club wheat, a.k.a. *Triticum aestivum* subspecies *compactum* (Host) MacKey; *Macha* wheat, a.k.a. *Triticum aestivum* subsp. *macha* (Dek. and Men.) MacKey; *Vavilovi* wheat, a.k.a. *Triticum aestivum* subsp. *vavilovi* (Tuman) Sears; Shot wheat, a.k.a. *Triticum aestivum* subsp. *sphacrococcum* (Perc.) MacKey), *T. aethiopicum, T. araraticum, T. boeoticum* (e.g., wild Einkorn, a.k.a. *Triticum boeotictim* Boiss), *T. carthlicum, T. compactum, T. dimitrium, T. dicoccoides* (e.g., wild *emmer*, a.k.a. *Triticum dicoccoides* (Koern. ex Ascb. & Graebn.) Aaronsohn.), *T. dicoccum* (e.g., *Emmer*), *T. durum* (e.g., *durum* wheat), *T. ispahanicum, T. karamyschevii, T. macha, T. militinae, T. monococcum* (e.g., Einkom, a.k.a. *Triticum monococcum* L.), *T. polonicum, T. spelta, T. sphaerococcum, T. timopheevii* (e.g. timopheevi wheat, a.k.a. *Triticum timopheevii* (Zbuk.) Zbuk.), *T. turanicum* (e.g., oriental wheat, a.k.a. *Triticum turanicum* jakubz), *T. turgidum* (e.g., poulard wheat, a.k.a. *Triticum turgidum* L.), *T. urartu, T. vavilovii*, and *T. zhukovskyi.*

Wheat genetics is more complicated than that of most other domesticated species. Some wheat species are diploid, with two sets of chromosomes, but many are stable polyploids, with four sets of chromosomes (tetraploid) or six (hexaploid). Most tetraploid wheats (e.g. *emmer* and *durum* wheat) are derived from wild *emmer, T. dicoccoides*. Wild *emmer* is itself the result of a hybridization between two diploid wild grasses, *T. urartu* and a wild goatgrass such as *Aegilops searsii* or *Ae. speltoides*. The unknown grass has never been identified among now surviving wild grasses, but the closest living relative is *Aegilops speltoides*. The hybridization that formed wild *emmer* (AABB) occurred in the wild, long before domestication, and was driven by natural selection. Hexaploid wheats evolved in farmers' fields. Common wheat (*Triticum aestivum,* 2n, 42, AABBDD) is one of the most important cereal crops in the world. Either domesticated *emmer* or *durum* wheat hybridized with yet another wild diploid grass (*Aegilops cylindrica*) to make the hexaploid wheats, spelt wheat and bread wheat. These have three sets of paired chromosomes, three times as many as in diploid wheat. Synthetic hexaploids made by crossing the wild goatgrass wheat ancestor *Aegilops tauschii* and various *durum* wheats are now being deployed, and these increase the genetic diversity of cultivated wheats.

Plant breeding methods for *Triticum* spp. are well known. Non-limiting methods for *Triticum* spp. breeding and agriculturally important traits (e.g., improving wheat yield, biotic stress tolerance, and abiotic stress tolerance etc.) are described in references Nos. 36-51, U.S. Pat. No. 7,652,204, U.S. Pat. No. 6,197,518, U.S. Pat. No. 7,034,208, U.S. Pat. No. 7,528,297, U.S. Pat. No. 6,407,311, US20080040826, US20090300783, US20060223707, US20110027233, US20080028480, US20090320152, US20090320151, WO/2001/029237A2, WO/2008/025097A1, and W0/2003/057848A2, each of which is incorporated by reference in its entirety for all purposes.

Genetic materials may be transferred between *Triticum* spp. and other species, for example, some plant species in the Triticeae tribe. Xiang et al., describe somatic hybrids between wheat and *Setaria italica* (Genome 47: 680-688 (2004)); Ge et al. describe protoplast electrofusion between common wheat and Italian ryegrass (In Vitro Cellular and Developmental Biology—Plant 42(2):179-187, 2006); Yue et al. describe asymmetic somatic hybridization between *Aeleuropus littorulis sinensis* and wheat (Plant Science, Volume 161, Issue 2, July 2001, Pages 259-266); Cai et al. describe somatic hybrids between *Festuca arundinacea Schreb*. and wheat (*Triticum aestivum* L.); Xiang et al. describe asymmetric somatic hybridization between wheat and *Avena sativa* L. (Science in China, Vol 46(3); 243-252); Zhou et al. describe asymmetric somatic hybridization between wheat and asymmetric somatic hybridization between wheat and *Avena sativa Haynaldia villosa* (Science in China, 44(3): 294-304); Xia et al. describe asymmetric somatic hybridization between wheat and *Agropyron elongatum* (Host) Nevishi (Theor Appl Genet. 2003 July; 107 (2):299-305. Epub 2003 Mar. 19); Li et al. describe symmetric somatic hybridization between wheat and *Psathyrostachys juncea* (Sheng Wu Gong Cheng Xue Bao. 2004 Jul.; 20(4):610-4). More hybridization between *Triticum* spp. and other species are described in reference Nos. 56-64.

Kinase Inhibitor Protein (KIP) Related Protein (KRP)

Plants have cyclin dependent kinases (CDK) that regulate the transitions between different phases of the cell cycle (Verkest et al., 2005, Switching the Cell Cycle. Kip-Related Proteins in Plant Cell Cycle Control, Plant Physiology, November 2005, Vol. 139, pp. 1099-1106, incorporated by reference in its entirety herein).

In *Arabidopsis* (*Arabidopsis thaliana*), at least two classes of CDKs are involved in cell cycle regulation: the A-type CDKs that are represented by only one gene in the model species *Arabidopsis* (designated Arath;CDKA;1) and the B-type CDK family that has four members, grouped into the B1 (Arath;CDKB1 and Arath;CDKB1;2) and B2 (Arath;CDKB2;1 and Arath;CDKB2;2) subclasses (Vandepoele et al., 2002, Genome-wide analysis of core cell cycle genes in *Arabidopsis*. Plant Cell 14: 903-916). A-type CDKs display kinase activity from late G1 phase until the end of mitosis, suggesting a role for this particular CDK at both the G1-to-S and G2-to-M transition points (Magyar et al., 1997; Porceddu et al., 2001; Sorrell et al., 2001). A central role for CDKA;1 in controlling cell number has been demonstrated using transgenic tobacco (*Nicotiana tabacum*) plants with reduced A-type CDK activity (Hemerly et al., 1995). The requirement for Arath;CKDA;1 at least for entry into mitosis has been demonstrated as well by cdka; 1 null mutants that fail to progress through the second mitosis during male gametophytic development (Nowack et al., 2005). The group of B-type CDKs displays a peak of activity at the G2-to-M phase transition only (Magyar et al., 1997; Porceddu et al., 2001; Sorrell et al., 2001), suggesting that they play a role at the onset of, or progression through, mitosis. Correspondingly, cells of plants with reduced B-type CDK activity arrest in the G2 phase of the cell cycle (Porceddu et al., 2001; Boudolf et. al., 2004).

CDK is regulated by cyclins. Plant cyclins are very complicated. There are at least 49 different cyclins in *Arabidopsis*, which were classified into seven subclasses (A, B, C, D, H, P, and T) (Vandepoele et al., 2002; Wang et al., 2004). CDK are also regulated by docking of small proteins, generally known as CDK inhibitors (CKIs). CKIs have been identified in many organisms, e.g., budding yeast (*Saccharomyces cerevisiae*), fission yeast (*Schizosaccharomyces pombe*), mammals, and plants, see, Mendenhall, 1998; Kwon T. K. et al. 1998; Vlach J. et al. 1997; Russo et al., 1996; Wang et al., 1997, 1998 and 2000; Lui et al., 2000; De Veylder et al., 2001; Jasinski et al., 2002a, 2002b; Coelho et al., 2005; Jasinski S. et al., 2002, each of which is incorporated by reference in its entirety).

Plant CKIs are also known as KIP Related Proteins (KRPs). They have cyclin binding and CDK binding domains at their C-terminal, however the mechanism regulating this protein stability and function remains unknown (Zhou et al., 2003a; Weinl et al. 2005). KRP activity can be both regulated at the transcriptional level or at the posttranslational level (Wang et al., 1998; De Veylder et al., 2001; Jasinski et al., 2002b; Ormenese et al., 2004; Coqueret, 2003; Hengst, 2004; Verkest et al., 2005; Coelho et al., 2005, each of which is incorporated by reference in its entirety). KRPs in plant normally localize in nucleus (Jasinski et al., 2002b; Zhou et al., 2003a; Weinl et al., 2005).

KRP can function as an integrator of developmental signals, and control endocycle onset, in different cell cycle programs (e.g., proliferation, endoreduplication, and cell cycle exit). See Wang et al., 1998; Richard et al., 2001; Himanen et al., 2002; Grafi and Larkins, 1995; Joube's et al., 1999; Verkest et al., 2005; Weinl et al., 2005; Boudolf et al., 2004b.

KRP Mutations

The present invention further provides mutated KRP polynucleotides and mutated KRP amino acid sequences compared to a wild type KRP gene or a wild type KRP protein. In some embodiments, the present invention provides mutations in one or more KRP genes that can be used to increase weight, size, and/or number of one or more organs, for example, to increase seed size, seed number, seed weight, and/or seed yield in a plant.

The mutations in a mutated KRP gene of the present invention can be in the coding region or the non-coding region of the KRP genes. The mutations can either lead to, or not lead to amino acid changes in the encoded KRP polypeptides. In some embodiments, the mutations can be missense, severe missense, silent, nonsense mutations. For example, the mutation can be nucleotide substitution, insertion, deletion, or genome re-arrangement, which in turn may lead to reading frame shift, amino acid substitution, insertion, deletion, and/or polypeptides truncation. As a result, the mutant KRP gene encodes a KRP polypeptide having less inhibition activity on a cyclin/CDK complex compared to a polypeptide encoded by its corresponding wild-type KRP gene.

As used herein, a nonsense mutation is a point mutation, e.g., a single-nucleotide polymorphism (SNP), in a sequence of DNA that results in a premature stop codon, or a nonsense codon in the transcribed mRNA, and in a truncated, incomplete, and usually nonfunctional protein product. A missense mutation (a type of nonsynonymous mutation) is a point mutation in which a single nucleotide is changed, resulting in a codon that codes for a different amino acid (mutations that change an amino acid to a stop codon are considered nonsense mutations, rather than missense mutations). This can render the resulting protein nonfunctional. Silent mutations are DNA mutations that do not result in a change to the amino acid sequence of a protein. They may occur in a non-coding region (outside of a gene or within an intron), or they may occur within an exon in a manner that does not alter the final amino acid sequence. A severe missense mutation changes the amino acid, which lead to dramatic changes in conformation, charge status etc.

The mutations can be located at any portion of a KRP gene, for example, at the 5', the middle, or the 3' of a KRP gene, resulting mutations in any portions of the encoded KRP protein, for example, in the CDK binding domain or the cyclin binding domain, so long as the mutated gene encodes a mutant KRP polypeptide partially or completely lose the ability to inhibit one or more cyclin/CDK complexes, compared to the protein encoded by the corresponding wild type KRP gene. The KRP and the cyclin/CDK complexes can belong to the same plant species, different plant species in the same genus, or different plant species in different genus.

Mutant KRP protein of the present invention can have one or more modifications to the wild-type KRP, or biologically active variant, or fragment thereof. Particularly suitable modifications include amino acid substitutions, insertions, deletions, or truncation. For example, amino acid substitutions can be generated as modifications in the CDK or the cyclin-binding region that reduce or eliminate binding. Similarly, amino acid substitutions can be generated as modifications in the CDK or the cyclin-binding region of the KRP that reduce or eliminate the inhibitory activity of the KRP towards the Cyclin/CDK complex. In typical embodiments, at least one non-conservative amino acid substitution, insertion, or deletion in the CDK binding region or the cyclin binding region is made to disrupt or modify binding of the CKI polypeptide to a CDK or cyclin protein. The substitutions may be single, where only one amino acid in the molecule has been substituted, or they may be multiple, where two or more amino acids have been substituted in the same molecule. Insertional KRP mutants are those with one or more amino acids inserted immediately adjacent to an amino acid at a particular position in the wild-type KRP protein molecule, biologically active variant, or fragment thereof. The insertion can be one or more amino acids. The insertion can consist, e.g., of one or two conservative amino acids. Amino acids similar in charge and/or structure to the amino acids adjacent to the site of insertion are defined as conservative. Alternatively, mutant KRP protein includes the insertion of an amino acid with a charge and/or structure that is substantially different from the amino acids adjacent to the site of insertion. In some other embodiments, the mutant KRP is a truncated protein losing one or more domains compared to the corresponding wild type KRP protein.

Methods of Increasing Organ Weight, Organ Size, Organ Number and/or Yield

The present invention further provides methods of increasing weight, size, and/or number of one or more organs, for example, methods of increasing seed weight, seed size, seed number, and/or yield in a plant. In some embodiments, the plant is a monocot plant. In some embodiments, the plant is a plant species in the Triticeae tribe, for example, a wheat plant. In some embodiments, the methods comprise disrupting one or more KRPs in the plant. The disruption can be at genomic level, transcriptional level, post-transcriptional level, translational level, and/or post translational level. In some embodiments, the methods comprise introducing one or more mutations into one or more KRP genes in the plant. In some embodiments, the methods comprise knocking-down expression of one or more KRP genes in the plant. In some embodiments, the methods comprise knocking-down KRP mRNAs stability in the plant. In some embodiments, the methods comprise down-regulating one or more KRP proteins activity in the plant.

For example, in some embodiments, the methods comprise introducing one or more KRP mutations of the present invention into the genome of the plant. In some embodiments, the methods comprise hybridizing a first plant having one or more mutated KRPs of the present invention with a second plant. In some embodiments, the hybridizing step comprises crossing the first plant with the second plant. In some embodiments, the hybridizing step comprises transferring the genetic materials in the first plant to the second plant through in vitro breeding, e.g., somatic hybridization.

Alternatively, the methods comprise mutating one or more KRPs in a plant. Methods of mutating a target gene have been known to one skilled in the art. These methods include, but are not limited to, mutagenesis (e.g., chemical mutagenesis, radiation mutagenesis, transpdson mutagenesis, insertional mutagenesis, signature tagged mutagenesis, site-directed mutagenesis, and natural mutagenesis), TILLING®, homologous recombination, knock-outs/knock-ins, antisense and RNA interference. Various types of mutagenesis can be used to produce and/or isolate variant nucleic acids that encode for protein molecules and/or to further modify/mutate the proteins of the present invention. They include but are not limited to site-directed, random point mutagenesis, homologous recombination, DNA shuffling, mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like. For more information of mutagenesis in plants, such as agents, protocols, see reference Nos. 66 to 70, each of which is herein incorporated by reference in its entity).

In some embodiments, random mutations in KRP genes are created in vitro. For example, a library of KRP genes with one or more random mutations can be generated, and the produced mutant KRP genes are subjected to the in vitro KRP-Cylin-CDK kinase assay described herein to determine if the mutant KRP genes can be used for increasing weight, size, and/or number of one or more organs, for example, for increasing seed size, seed number, seed weight and/or yield. Methods for in vitro mutagenesis include, but are not limited to error-prone PCR, Rolling circle error-prone PCR, mutator strains, temporary mutator strains, insertion mutagenesis, chemical mutagenesis (e.g., EMS, nitrous acid etc.), DNA shuffling, and site directed random mutagenesis. More methods are described in Chusacultanachai et al, Fujii et al., Braman, and Trower. Commercial random mutagenesis kits are available, such as Random Mutagenesis Kits from Jena Bioscience. cat. No: PP-101, Diversify® PCR random mutagenesis kit from Clontech.

In some embodiments, mutated KRPs of the present invention are generated in vivo by methods such as TILL- ING®, site-directed mutagenesis, homologous recombination, etc. The produced mutant KRP genes are screened and subjected to the in vitro KRP-Cylin-CDK kinase assay described herein to determine if the mutant KRP genes can be used for increasing weight, size, and/or number of one or more organs, for example, for increasing seed size, seed number, seed weight and/or yield.

In some embodiments, the methods comprise knocking down expression of one or more KRPs in the plant. Techniques which can be employed in accordance with the present invention to knock down gene expression, include, but are not limited to: (1) disrupting a gene's transcript, such as disrupting a gene's mRNA transcript; (2) disrupting the function of a polypeptide encoded by a gene, or (3) disrupting the gene itself.

For example, antisense RNA, ribozyme, dsRNAi, RNA interference (RNAi) technologies can be used in the present invention to target RNA transcripts of one or more KRP genes. Antisense RNA technology involves expressing in, or introducing into, a cell an RNA molecule (or RNA derivative) that is complementary to, or antisense to, sequences found in a particular mRNA in a cell. By associating with the mRNA, the antisense RNA can inhibit translation of the encoded gene product. The use of antisense technology to reduce or inhibit the expression of specific plant genes has been described, for example in European Patent Publication No. 271988, Smith et al., Nature, 334:724-726 (1988); Smith et. al., Plant Mol. Biol., 14:369-379 (1990)).

A ribozyme is an RNA that has both a catalytic domain and a sequence that is complementary to a particular mRNA. The ribozyme functions by associating with the mRNA (through the complementary domain of the ribozyme) and then cleaving (degrading) the message using the catalytic domain.

RNA interference (RNAi) is the process of sequence-specific, post-transcriptional gene silencing or transcriptional gene silencing in animals and plants, initiated by double-stranded RNA (dsRNA) that is homologous in sequence to the silenced gene. The RNAi technique is discussed, for example, in Elibashir, et al., Methods Enzymol. 26:199 (2002); McManus & Sharp, Nature Rev. Genetics 3:737 (2002); PCT application WO 01/75164; Martinez et al., Cell 110:563 (2002); Elbashir et al., supra; Lagos-Quintana et al., Curr. Biol. 12:735 (2002); Tuschl et al., Nature Biotechnol. 20:446 (2002); Tuschl, Chembiochem. 2:239 (2001); Harborth et al., J. Cell Sci. 114:4557 (2001); et al., EMBO J. 20:6877 (2001); Lagos-Quintana et al., Science 294:8538 (2001); Hutvagner et al., loc cit, 834; Elbashir et al., Nature 411:494 (2001).

The term "dsRNA" or "dsRNA molecule" or "double-strand RNA effector molecule" refers to an at least partially double-strand ribonucleic acid molecule containing a region of at least about 19 or more nucleotides that are in a double-strand conformation. The double-stranded RNA effector molecule may be a duplex double-stranded RNA formed from two separate RNA strands or it may be a single RNA strand with regions of self-complementarity capable of assuming an at least partially double-stranded hairpin conformation (i.e., a hairpin dsRNA or stem-loop dsRNA). In various embodiments, the dsRNA consists entirely of ribonucleotides or consists of a mixture of ribonucleotides and deoxynucleotides, such as RNA/DNA hybrids. The dsRNA may be a single molecule with regions of self-complementarity such that nucleotides in one segment of the molecule base pair with nucleotides in another segment of the molecule. In one aspect, the regions of self-complementarity are linked by a region of at least about 3-4 nucleotides, or about 5, 6, 7, 9 to 15 nucleotides or more, which lacks complementarity to another part of the molecule and thus remains single-stranded (i.e., the "loop region"). Such a molecule will assume a partially double-stranded stem-loop structure, optionally, with short single stranded 5' and/or 3' ends. In one aspect the regions of self-complementarity of the hairpin dsRNA or the double-stranded region of a duplex dsRNA will comprise an Effector Sequence and an Effector Complement (e.g., linked by a single-stranded loop region in a hairpin dsRNA). The Effector Sequence or Effector Strand is that strand of the double-stranded region or duplex which is incorporated in or associates with RISC. In one aspect the double-stranded RNA effector molecule will comprise an at least 19 contiguous nucleotide effector sequence, preferably 19 to 29, 19 to 27, or 19 to 21 nucleotides, which is a reverse complement to the RNA of KRP, or an opposite strand replication intermediate, or the anti-genomic plus strand or non-mRNA plus strand sequences of KRP. In one embodiment, said double-stranded RNA effector molecules are provided by providing to a plant, plant tissue, or plant cell an expression construct comprising one or more double-stranded RNA effector molecules. In one embodiment, the expression construct comprise a double-strand RNA derived from any one of SEQ ID NOs 1-5. One skilled in the art will be able to design suitable double-strand RNA effector molecule based on the nucleotide sequences of KRPs in the present invention.

In some embodiments, the dsRNA effector molecule of the invention is a "hairpin dsRNA", a "dsRNA hairpin", "short-hairpin RNA" or "shRNA", i.e., an RNA molecule of less than approximately 400 to 500 nucleotides (nt), or less than 100 to 200 nt, in which at least one stretch of at least 15 to 100 nucleotides (e.g., 17 to 50 nt, 19 to 29 nt) is based paired with a complementary sequence located on the same RNA molecule (single RNA strand), and where said sequence and complementary sequence are separated by an unpaired region of at least about 4 to 7 nucleotides (or about 9 to about 15 nt, about 15 to about 100 nt, about 100 to about 1000 nt) which forms a single-stranded loop above the stem structure created by the two regions of base complementarity. The shRNA molecules comprise at least one stem-loop structure comprising a double-stranded stem region of about 17 to about 100 bp; about 17 to about 50 bp; about 40 to about 100 bp; about 18 to about 40 bp; or from about 19 to about 29 bp; homologous and complementary to a target sequence to be inhibited; and an unpaired loop region of at least about 4 to 7 nucleotides, or about 9 to about 15 nucleotides, about 15 to about 100 nt, about 100 to about 1000 nt, which forms a single-stranded loop above the stem structure created by the two regions of base complementarity. It will be recognized, however, that it is not strictly necessary to include a "loop region" or "loop sequence" because an RNA molecule comprising a sequence followed immediately by its reverse complement will tend to assume a stem-loop conformation even when not separated by an irrelevant "stuffer" sequence.

The plants with disrupted one or more KRPs of the present invention can be used for many purposes. In one embodiment, a plant of the present invention is used as a donor plant of genetic material which can be transferred to a recipient plant to produce a plant with desired agronomic traits which has the transferred genetic material and having increased weight, size, and/or number of one or more organs, for example, a plant with increased seed weight, seed size, seed number and/or yield. Any suitable method known in the art can be applied to transfer genetic material from a donor plant to a recipient plant. In most cases, such genetic material is genomic material.

Descriptions of other breeding methods that are commonly used for different traits and crops can be found in one of several reference books (e.g., R. W. Allard, 1960, Principles of Plant Breeding, John Wiley and Son, pp. 115-161; N. W. Simmonds, 1979, Principles of Crop Improvement, Longman Group Limited; W. R. Fehr, 1987, Principles of Crop Development, Macmillan Publishing Co.; N. F. Jensen, 1988, Plant Breeding Methodology, John Wiley & Sons).

In some embodiments, a backcross breeding process is used. The backcross breeding process comprises the following steps: (a) crossing a first wheat plant having one or more disrupted KRP genes with a second plant that comprises the desired trait(s); (b) selecting the F, progeny plants that have the desired trait(s); (c) crossing the selected F, progeny plants with the first wheat plant or the second wheat plant to produce backcross progeny plants; (d) selecting for backcross progeny plants that have the desired trait(s) and one or more disrupted KRP genes to produce selected backcross progeny plants; and (e) repeating steps (c)-(d) one, two, three, four, five six, seven, eight, nine, or more times in succession to produce selected, second, third, fourth, fifth, sixth, seventh, eighth, ninth, or higher backcross progeny plants that comprise said disrupted KRP genes, and/or the desired trait(s).

The invention further provides methods for developing wheat varieties in a wheat breeding program using plant breeding techniques including recurrent selection, backcrossing, pedigree breeding, molecular markers (Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs). Amplified Fragment Length Polymorphisms (AFLPs), and Simple Sequence Repeats (SSRs) which are also referred to as Microsatellites, etc.) enhanced selection, genetic marker enhanced selection, and transformation. Seeds, plants, and part(s) thereof produced by such breeding methods are also part of the invention.

In one embodiment, the whole genome of the plants of the present invention with disrupted KRP(s) is transferred into a recipient plant. This can be done by conventional breeding such as crossing, or somatic hybridization. In another embodiment, at least the parts having the disrupted KRP(s) of the donor plant's genome are transferred. This can be done by crossing donor plants to a recipient plant to create a F1 plant, followed with one or more backcrosses to one of the parent plants to give plants with the desired genetic background. Molecular marker assisted breeding can be utilized to monitor the transfer of the genetic material. The produced offsprings can be selected for having increased weight, size, and/or number of one or more organs, for example, having increased seed weight, seed size, seed number and/or yield.

In one embodiment, the recipient plant is an elite line having one or more certain agronomically important traits. As used herein, "agronomically important traits" include any phenotype in a plant or plant part that is useful or advantageous for human use. Examples of agronomically important traits include but are not limited to those that result in increased biomass production, increased food production, improved food quality, decrease in cracking, quicker color change when the fruit matures etc. Additional examples of agronomically important traits includes pest resistance, vigor, development time (time to harvest), enhanced nutrient content, increased seed oil content, novel growth patterns, flavors or colors, salt, heat, drought and cold tolerance, and the like.

Other agronomically important traits include resistance to biotic and/or abiotic stresses. As used herein, the phrase "biotic stress" or "biotic pressure" refers to a situation where damage is done to plants by other living organisms, such as bacteria, viruses, fungi, parasites, insects, weeds, animals and human. As used herein, the phrase "abiotic stress" or "abiotic pressure" refers to the negative impact of non-living factors on plants in a specific environment. The non-living variable must influence the environment beyond its normal range of variation to adversely affect the population performance or individual physiology of plants in a significant way. Non-limiting examples of stressors are high winds, extreme temperatures, drought, flood, and other natural disasters, such as tornados and wildfires.

In some embodiments, the method comprises i) making a cross between a plant of the present invention to a second plant to produce a F1 plant, for example, a wheat plant with one or more disrupted KRP genes. Optionally, the method further comprises ii) backcrossing the F1 plant to the first or the second wheat plant; and iii) repeating the backcrossing step to generate a near isogenic line, wherein the one or more disrupted KRPs in the first wheat plant are integrated into the genome of the near isogenic line.

In some embodiments, the disrupted KRP gene is selected from the group consisting of TaKRP1A, TaKRP1B, TaKRP1D, TaKRP2A, TaKRP2B, TaKRP2D, TaKRP4A, TaKRP4B, TaKRP4D, TaKRP5A, TaKRP5B, or TaKRP5D. In some embodiments, the first wheat plant comprises one or more mutations selected from any one of mutations listed in Tables 2 and 3 for a particular KRP gene.

In some embodiments, the methods of the present invention can increase the average weight, size, and/or number of one or more organs, for example, increase the average seed weight, seed size, seed number and/or yield of a plant by at least 5%, at least 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380% e, 390%, 400%, or greater when compared to a control plant not having disrupted KRP(s).

The mutated KRPs in a plant genome can be viewed as quantitative trait loci (QTLs) related to organ weight, organ size, organ number and/or yield. A QTL is a region of DNA that is associated with a particular phenotypic trait—these QTLs are often found on different chromosomes. Knowing the number of QTLs that explains variation in a particular phenotypic trait informs about the genetic architecture of the trait. It may tell that plant with preferred phenotype is controlled by many genes of small effect, or by a few genes of large effect. Therefore, QTL mapping can be applied to determine the parts of the donor plant's genome comprising the mutated KRPs, and facilitate the breeding methods.

One or more of such QTLs of mutated KRPs in a donor can be transferred to a recipient plant, confirming the phenotype of having increased weight, size, and/or number of one or more organs, for example, increased seed weight, seed size, seed number, and/or yield. In some further embodiments, the QTLs related to mutated KRPs can be combined with one or more other QTLs that contribute to agriculturally important phenotypes, such as yield enhancement, resistance to biotic and abiotic stresses, etc. The primers in the present invention used for genotyping the mutated KRPs can be used as molecular markers indicating the presence or absence of the mutated KRPs. Instead, molecular markers closely linked to the mutated KRPs can be also used. Methods of developing molecular markers and their applications are described by Avise (Molecular markers, natural history, and evolution, Publisher: Sinauer Associates, 2004, ISBN 0878930418, 9780878930418), Srivastava et al. (Plant biotechnology and molecular markers, Publisher: Springer, 2004, ISBN1402019114, 9781402019111), and Vienne (Molecular markers in plant genetics and biotechnology, Publisher: Science Publishers, 2003), each of which is incorporated by reference in its entirety.

Without wishing to be bond by any theory, besides increased seed size, seed number, seed weight and/or yield, a plant having one or more disrupted KRPs may have one or more other phenotypes that are agriculturally or industrially important, which include, but are not limited to, increased plant vigor, organ size, increased adaptability to the environment, increased oil production, increased biomass production, and traits that allow a plant to grow better under certain environments with specific temperatures, soil conditions and levels of sunlight and precipitation compared to a wild type control plant.

Tissue Culture and Grafting

Modern plant tissue culture is performed under aseptic conditions under filtered air. Living plant materials from the environment are naturally contaminated on their surfaces (and sometimes interiors) with microorganisms, so surface sterilization of starting materials (explants) in chemical solutions (usually alcohol or bleach) is required. Explants are then usually placed on the surface of a solid culture medium, but are sometimes placed directly into a liquid medium, particularly when cell suspension cultures are desired. Solid and liquid media are generally composed of inorganic salts plus a few organic nutrients, vitamins and plant hormones. Solid media are prepared from liquid media with the addition of a gelling agent, usually purified agar.

The composition of the medium, particularly the plant hormones and the nitrogen source (nitrate versus ammonium salts or amino acids) have profound effects on the morphology of the tissues that grow from the initial explant. For example, an excess of auxin will often result in a proliferation of roots, while an excess of cytokinin may yield shoots. A balance of both auxin and cytokinin will often produce an unorganized growth of cells, or callus, but the morphology of the outgrowth will depend on the plant species as well as the medium composition. As cultures grow, pieces are typically sliced off and transferred to new media (subcultured) to allow for growth or to alter the morphology of the culture. The skill and experience of the tissue culturist are important in judging which pieces to culture and which to discard. As shoots emerge from a culture, they may be sliced off and rooted with auxin to produce plantlets which, when mature, can be transferred to potting soil for further growth in the greenhouse as normal plants.

The tissue obtained from the plant to culture is called an explant. Based on work with certain model systems, particularly tobacco, it has often been claimed that a totipotent explant can be grown from any part of the plant. However, this concept has been vitiated in practice. In many species explants of various organs vary in their rates of growth and regeneration, while some do not grow at all. The choice of explant material also determines if the plantlets developed via tissue culture are haploid or diploid. Also the risk of microbial contamination is increased with inappropriate explants. Thus it is very important that an appropriate choice of explant be made prior to tissue culture.

The specific differences in the regeneration potential of different organs and explants have various explanations. The significant factors include differences in the stage of the cells in the cell cycle, the availability of or ability to transport endogenous growth regulators, and the metabolic capabilities of the cells. The most commonly used tissue explants are the meristematic ends of the plants like the stem tip, auxiliary bud tip and root tip. These tissues have high rates of cell division and either concentrate or produce required growth regulating substances including auxins and cytokinins. Some explants, like the root tip, are hard to isolate and are contaminated with soil microflora that become problematic during the tissue culture process. Certain soil microflora can form tight associations with the root systems, or even grow within the root. Soil particles bound to roots are difficult to remove without injury to the roots that then allows microbial attack. These associated microflora will generally overgrow the tissue culture medium before there is significant growth of plant tissue. Aerial (above soil) explants are also rich in undesirable microflora. However, they are more easily removed from the explant by gentle rinsing, and the remainder usually can be killed by surface sterilization. Most of the surface microflora do not form tight associations with the plant tissue. Such associations can usually be found by visual inspection as a mosaic, de-colorization or localized necrosis on the surface of the explant.

An alternative for obtaining uncontaminated explants is to take explants from seedlings which are aseptically grown from surface-sterilized seeds. The hard surface of the seed is less permeable to penetration of harsh surface sterilizing agents, such as hypochlorite, so the acceptable conditions of sterilization used for seeds can be much more stringent than for vegetative tissues.

Tissue cultured plants are clones, if the original mother plant used to produce the first explants is susceptible to a pathogen or environmental condition, the entire crop would be susceptible to the same problem, conversely any positive traits would remain within the line also. Plant tissue culture is used widely in plant science; it also has a number of commercial applications. Applications include:

1. Micropropagation is widely used in forestry and in floriculture. Micropropagation can also be used to conserve rare or endangered plant species.
2. A plant breeder may use tissue culture to screen cells rather than plants for advantageous characters, e.g. pathogen resistance/tolerance.
3. Large-scale growth of plant cells in liquid culture inside bioreactors as a source of secondary products, like recombinant proteins used as biopharmaceuticals.
4. To cross distantly related species by protoplast fusion and regeneration of the novel hybrid.
5. To cross-pollinate distantly related species and then tissue culture the resulting embryo which would otherwise normally die (Embryo Rescue).
6. For production of doubled monoploid (dihaploid) plants from haploid cultures to achieve homozygous lines more rapidly in breeding programs, usually by treatment with colchicine which causes doubling of the chromosome number.

7. As a tissue for transformation, followed by either short-term testing of genetic constructs or regeneration of transgenic plants.
8. Certain techniques such as meristem tip culture can be used to produce clean plant material from infected stock, such as potatoes and many species of soft fruit.
9. Micropropagation using meristem and shoot culture to produce large numbers of identical individuals.

Non-limiting exemplary tissue culture methods for wheat, rice, maize have been described by Trione et al., Dodig, et al., O'Hara et al., Zaidi et al., Wang et al., Ting et al., Hawes et al., and Sheridan, each of which is incorporated by reference in its entirety.

The present invention also provides a cutting, a rootstock, a scion, or an explant from the plants as described above for grafting.

Grafting is a method of asexual plant propagation widely used in agriculture and horticulture where the tissues of one plant are encouraged to fuse with those of another. It is most commonly used for the propagation of trees and shrubs grown commercially. In most cases, one plant is selected for its roots, and this is called the stock or rootstock. The other plant is selected for its stems, leaves, flowers, or fruits and is called the scion. The scion contains the desired genes to be duplicated in future production by the stock/scion plant. In stem grafting, a common grafting method, a shoot of a selected, desired plant cultivar is grafted onto the stock of another type. In another common form called budding, a dormant side bud is grafted on the stem of another stock plant, and when it has fused successfully, it is encouraged to grow by cutting out the stem above the new bud.

For successful grafting to take place, the vascular cambium tissues of the stock and scion plants must be placed in contact with each other. Both tissues must be kept alive until the graft has taken, usually a period of a few weeks. Successful grafting only requires that a vascular connection takes place between the two tissues. A physical weak point often still occurs at the graft, because the structural tissue of the two distinct plants, such as wood, may not fuse.

Exemplary grafting techniques include, approach grafting, budding grafting (patch budding, chip budding, T-budding), cleft grafting, side grafting, whip grafting, stub grafting, awl grafting, veneer grafting, bark grafting, tongue grafting, et al. Detailed non-limiting grafting methods for wheat and maize are described in Lacadena, 1968, and Katsumi et al., each of which is incorporated by reference in its entirety.

Plant Transformation

The isolated polynucleotides of the present invention comprise a sequence selected from the group consisting of: (a) sequences recited in SEQ ID NO: 40, 41, 43, 44, 46, 47, 49, 50, 52, 53, 55, 56, 58, 59, 60, 62, 63, 64, 66, 67, 68, 70, 71, 73, 74, 76 and 77, or portions thereof; (b) complements of the sequences recited in SEQ ID NO: 40, 41, 43, 44, 46, 47, 49, 50, 52, 53, 55, 56, 58, 59, 60, 62, 63, 64, 66, 67, 68, 70, 71, 73, 74, 76 and 77, or portions thereof; (c) reverse complements of the sequences recited in SEQ ID NO: 40, 41, 43, 44, 46, 47, 49, 50, 52, 53, 55, 56, 58, 59, 60, 62, 63, 64, 66, 67, 68, 70, 71, 73, 74, 76 and 77, or portions thereof; (d) reverse sequences of the sequences recited in SEQ ID NO: 40, 41, 43, 44, 46, 47, 49, 50, 52, 53, 55, 56, 58, 59, 60, 62, 63, 64, 66, 67, 68, 70, 71, 73, 74, 76 and 77, or portions thereof; and (e) sequences having at least 50%, 75%, 90%, 95% or 98% identity, as defined herein, to a sequence of (a)-(d) or a specified region of a sequence of (a)-(d).

The present invention also provides recombinant polynucleotide sequences comprising the isolated nucleic acid sequence of any one of the polynucleotides described above operably linked to suitable regulatory sequences.

The present invention also provides recombinant constructs comprising the recombinant polynucleotide sequences as described above. The present invention further comprises interfering RNA (RNAi) constructs based on the nucleic acid sequences of the present invention, targeting one or more KRPs in a *Triticum* spp.

The polynucleotides of the present invention can be transformed into a plant. The most common method for the introduction of new genetic material into a plant genome involves the use of living cells of the bacterial pathogen *Agrobacterium tumefaciens* to literally inject a piece of DNA, called transfer or T-DNA, into individual plant cells (usually following wounding of the tissue) where it is targeted to the plant nucleus for chromosomal integration. There are numerous patents governing *Agrobacterium* mediated transformation and particular DNA delivery plasmids designed specifically for use with *Agrobacterium*—for example, U.S. Pat. No. 4,536,475, EP0265556, EP0270822, WO8504899, WO8603516, U.S. Pat. No. 5,591,616, EP0604662, EP0672752, WO8603776, WO9209696, WO9419930, WO9967357, U.S. Pat. No. 4,399,216, WO8303259, U.S. Pat. No. 5,731,179, EP068730, WO9516031, U.S. Pat. No. 5,693,512, U.S. Pat. No. 6,051,757 and EP904362A1. *Agrobacterium*-mediated plant transformation involves as a first step the placement of DNA fragments cloned on plasmids into living *Agrobacterium* cells, which are then subsequently used for transformation into individual plant cells. *Agrobacterium*-mediated plant transformation is thus an indirect plant transformation method. Methods of *Agrobacterium*-mediated plant transformation that involve using vectors with no T-DNA are also well known to those skilled in the art and can have applicability in the present invention. See, for example, U.S. Pat. No. 7,250,554, which utilizes P-DNA instead of T-DNA in the transformation vector.

Direct plant transformation methods using DNA have also been reported. The first of these to be reported historically is electroporation, which utilizes an electrical current applied to a solution containing plant cells (M. E. Fromm et al., Nature, 319, 791 (1986); H. Jones et al., Plant Mol. Biol., 13, 501 (1989) and H. Yang et al., Plant Cell Reports, 7, 421 (1988). Another direct method, called "biolistic bombardment", uses ultrafine particles, usually tungsten or gold; that are coated with DNA and then sprayed onto the surface of a plant tissue with sufficient force to cause the particles to penetrate plant cells, including the thick cell wall, membrane and nuclear envelope, but without killing at least some of them (U.S. Pat. No. 5,204,253, U.S. Pat. No. 5,015,580). A third direct niethod uses fibrous forms of metal or ceramic consisting of sharp, porous or hollow needle-like projections that literally impale the cells, and also the nuclear envelope of cells. Both silicon carbide and aluminum borate whiskers have been used for plant transformation (Mizuno et al., 2004; Petolino et al., 2000; U.S. Pat. No. 5,302,523 US Application 20040197909) and also for bacterial and animal transformation (Kaepler et al., 1992; Raloff, 1990; Wang, 1995). There are other methods reported, and undoubtedly, additional methods will be developed. However, the efficiencies of each of these indirect or direct methods in introducing foreign DNA into plant cells are invariably extremely low, making it necessary to use some method for selection of only those cells that have been transformed, and further, allowing growth and regeneration into plants of only those cells that have been transformed.

For efficient plant transformation, a selection method must be employed such that whole plants are regenerated from a single transformed cell and every cell of the transformed plant carries the DNA of interest. These methods can employ positive selection, whereby a foreign gene is supplied to a plant cell that allows it to utilize a substrate present in the medium that it otherwise could not use, such as mannose or xylose (for example, refer U.S. Pat. No. 5,767,378; U.S. Pat. No. 5,994,629). More typically, however, negative selection is used because it is more efficient, utilizing selective agents such as herbicides or antibiotics that either kill or inhibit the growth of nontransformed plant cells and reducing the possibility of chimeras. Resistance genes that are effective against negative selective agents are provided on the introduced foreign DNA used for the plant transformation. For example, one of the most popular selective agents used is the antibiotic kanamycin, together with the resistance gene neomycin phosphotransferase (nptll), which confers resistance to kanamycin and related antibiotics (see, for example, Messing & Vierra, Gene 19: 259-268 (1982); Bevan et al., Nature 304:184-187 (1983)). However, many different antibiotics and antibiotic resistance genes can be used for transformation purposes (refer U.S. Pat. No. 5,034,322, U.S. Pat. No. 6,174,724 and U.S. Pat. No. 6,255,560). In addition, several herbicides and herbicide resistance genes have been used for transformation purposes, including the bar gene, which confers resistance to the herbicide phosphinothricin (White et al., *Nucl Acids Res* 18: 1062 (1990), Spencer et al., *Theor Appl Genet* 79: 625-631(1990), U.S. Pat. No. 4,795,855, U.S. Pat. No. 5,378,824 and U.S. Pat. No. 6,107,549). In addition, the dhfr gene, which confers resistance to the anticancer agent methotrexate, has been used for selection (Bourouis et al., *EMBO J.* 2(7): 1099-1104 (1983).

The expression control elements used to regulate the expression of a given protein can either be the expression control element that is normally found associated with the coding sequence (homologous expression element) or can be a heterologous expression control element. A variety of homologous and heterologous expression control elements are known in the art and can readily be used to make expression units for use in the present invention. Transcription initiation regions, for example, can include any of the various opine initiation regions, such as octopine, mannopine, nopaline and the like that are found in the Ti plasmids of *Agrobacterium tumefaciens*. Alternatively, plant viral promoters can also be used, such as the cauliflower mosaic virus 19S and 35S promoters (CaMV 19S and CaMV 35S promoters, respectively) to control gene expression in a plant (U.S. Pat. Nos. 5,352,605; 5,530,196 and 5,858,742 for example). Enhancer sequences derived from the CaMV can also be utilized (U.S. Pat. Nos. 5,164,316; 5,196,525; 5,322,938; 5,530,196; 5,352,605; 5,359,142; and 5,858,742 for example). Lastly, plant promoters such as prolifera promoter, fruit specific promoters, Ap3 promoter, heat shock promoters, seed specific promoters, etc. can also be used.

Either a gamete specific promoter, a constitutive promoter (such as the CaMV or Nos promoter), an organ specific promoter (e.g., stem specific promoter), or an inducible promoter is typically ligated to the protein or antisense encoding region using standard techniques known in the art. The expression unit may be further optimized by employing supplemental elements such as transcription terminators and/or enhancer elements. The expression cassette can comprise, for example, a seed specific promoter (e.g. the phaseolin promoter (U.S. Pat. No. 5,504,200). The term “seed specific promoter”, means that a gene expressed under the control of the promoter is predominantly expressed in plant seeds with no or no substantial expression, typically less than 10% of the overall expression level, in other plant tissues. Seed specific promoters have been well known in the art, for example, U.S. Pat. Nos. 5,623,067, 5,717,129, 6,403,371, 6,566,584, 6,642,437, 6,777,591, 7,081,565, 7,157,629, 7,192,774, 7,405,345, 7,554,006, 7,589,252, 7,595,384, 7,619,135, 7,642,346, and US Application Publication Nos. 20030005485, 20030172403, 20040088754, 20040255350, 20050125861, 20050229273, 20060191044, 20070022502, 20070118933, 20070199098, 20080313771, and 20090100551.

Thus, for expression in plants, the expression units will typically contain, in addition to the protein sequence, a plant promoter region, a transcription initiation site and a transcription termination sequence. Unique restriction enzyme sites at the 5' and 3' ends of the expression unit are typically included to allow for easy insertion into a preexisting vector.

In the construction of heterologous promoter/structural gene or antisense combinations, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette can also contain a transcription termination region downstream of the structural gene to provide for efficient termination. The termination region may be obtained from the same gene as the promoter sequence or may be obtained from different genes. If the mRNA encoded by the structural gene is to be efficiently processed, DNA sequences which direct polyadenylation of the RNA are also commonly added to the vector construct. Polyadenylation sequences include, but are not limited to the *Agrobacterium* octopine synthase signal (Gielen et al., EMBO J 3:835-846 (1984)) or the nopaline synthase signal (Depicker et al., Mol. and Appl. Genet. 1:561-573 (1982)). The resulting expression unit is ligated into or otherwise constructed to be included in a vector that is appropriate for higher plant transformation. One or more expression units may be included in the same vector. The vector will typically contain a selectable marker gene expression unit by which transformed plant cells can be identified in culture. Usually, the marker gene will encode resistance to an antibiotic, such as G418, hygromycin, bleomycin, kanamycin, or gentamicin or to an herbicide, such as glyphosate (Round-Up) or glufosinate (BASTA) or atrazine. Replication sequences, of bacterial or viral origin, are generally also included to allow the vector to be tloned in a bacterial or phage host, preferably a broad host range prokaryotic origin of replication is included. A selectable marker for bacteria may also be included to allow selection of bacterial cells bearing the desired construct. Suitable prokaryotic selectable markers include resistance to antibiotics such as ampicillin, kanamycin or tetracycline. Other DNA sequences encoding additional functions may also be present in the vector, as is known in the art. For instance, in the case of *Agrobacterium* transformations, T-DNA sequences will also be included for subsequent transfer to plant chromosomes.

To introduce a desired gene or set of genes by conventional methods requires a sexual cross between two lines, and then repeated back-crossing between hybrid offspring and one of the parents until a plant with the desired characteristics is obtained. This process, however, is restricted to plants that can sexually hybridize, and genes in addition to the desired gene will be transferred.

Recombinant DNA techniques allow plant researchers to circumvent these limitations by enabling plant geneticists to identify and clone specific genes for desirable traits, such as resistance to an insect pest, and to introduce these genes into already useful varieties of plants. Once the foreign genes have been introduced into a plant, that plant can then be used in conventional plant breeding schemes (e.g., pedigree breeding, single-seed-descent breeding schemes, reciprocal recurrent selection) to produce progeny which also contain the gene of interest.

Genes can be introduced in a site directed fashion using homologous recombination. Homologous recombination permits site specific modifications in endogenous genes and thus inherited or acquired mutations may be corrected, and/or novel alterations may be engineered into the genome. Homologous recombination and site-directed integration in plants are discussed in, for example, U.S. Pat. Nos. 5,451,513; 5,501,967 and 5,527,695.

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; and *Agrobacterium*-mediated transformation. See, for example, U.S. Pat. Nos. 5,405,765; 5,472,869; 5,538,877; 5,538,880; 5,550,318; 5,641,664; 5,736,369 and 5,736,369; International Patent Application Publication Nos. WO2002/038779 and WO/2009/117555; Lu et al., (Plant Cell Reports, 2008, 27:273-278); Watson et al., Recombinant DNA, Scientific American Books (1992); Hinchee et al., Bio/Tech. 6:915-922 (1988); McCabe et al., Bio/Tech. 6:923-926 (1988); Toriyama et al., Bio/Tech. 6:1072-1074 (1988); Fromm et al., Bio/Tech. 8:833-839 (1990); Mullins et al., Bio/Tech. 8:833-839 (1990); Hiei et al., Plant Molecular Biology 35:205-218 (1997); Ishida et al., Nature Biotechnology 14:745-750 (1996); Zhang et al., Molecular Biotechnology 8:223-231 (1997); Ku et al., Nature Biotechnology 17:76-80 (1999); and, Raineri et al., BiofTech. 8:33-38 (1990)), each of which is expressly incorporated herein by reference in their entirety.

*Agrobacterium tumefaciens* is a naturally occurring bacterium that is capable of inserting its DNA (genetic information) into plants, resulting in a type of injury to the plant known as crown gall. Most species of plants can now be transformed using this method, including cucurbitaceous species.

Microprojectile bombardment is also known as particle acceleration, biolistic bombardment, and the gene gun (Biolistic® Gene Gun). The gene gun is used to shoot pellets that are coated with genes (e.g., for desired traits) into plant seeds or plant tissues in order to get the plant cells to then express the new genes. The gene gun uses an actual explosive (.22 caliber blank) to propel the material. Compressed air or steam may also be used as the propellant. The Biolistic® Gene Gun was invented in 1983-1984 at Cornell University by John Sanford, Edward Wolf, and Nelson Allen. It and its registered trademark are now owned by E. I. du Pont de Nemours and Company. Most species of plants have been transformed using this method.

A transgenic plant formed using *Agrobacterium* transformation methods typically contains a single gene on one chromosome, although multiple copies are possible. Such transgenic plants can be referred to as being hemizygous for the added gene. A more accurate name for such a plant is an independent segregant, because each transformed plant represents a unique T-DNA integration event (U.S. Pat. No. 6,156,953). A transgene locus is generally characterized by the presence and/or absence of the transgene. A heterozygous genotype in which one allele corresponds to the absence of the transgene is also designated hemizygous (U.S. Pat. No. 6,008,437).

General transformation methods, and specific methods for transforming certain plant species (e.g., maize, rice, wheat, barley, soybean) are described in U.S. Pat. Nos. 4,940,838, 5,464,763, 5,149,645, 5,501,967, 6,265,638, 4,693,976, 5,635,381, 5,731,179, 5,693,512, 6,162,965, 5,693,512, 5,981,840, 6,420,630, 6,919,494, 6,329,571, 6,215,051, 6,369,298, 5,169,770, 5,376,543, 5,416,011, 5,569,834, 5,824,877, 5,959,179, 5,563,055, and 5,968,830, each of which is incorporated by reference in its entirety.

This invention is further illustrated by the following examples which should not be construed as limiting. The contents of all references, patents and published patent applications cited throughout this application, as well as the Figures and the Sequence Listing, are incorporated herein by reference.

EXAMPLES

Example 1

Identification of KRP Homologues from Wheat

The inventors used available EST collections and proprietary sequences to generate partial predicted proteins for the different wheat KRP genes (SEQ ID Nos 1-5).

A multiple sequence analysis was generated using the protein sequences for rice, maize, and wheat KRP genes. Alignment of sequences was done by using online Multiple Sequence Alignment (MSA) service provided by European Bioinformatics Institute and the bootstrap values were calculated by using online software TreeTop-Phylogenetic Tree Prediction provided by Moscow State University (FIG. 1). Values in the branches in FIG. 1 are bootstrap values.

Based on our phylogenetic tree construction, we discerned a correspondence between the wheat, rice, and maize KRP genes. The relationships we figured out between the different KRP genes appear similar to the one reported by Barroco et al. (2006), The cyclin-dependent kinase inhibitor Orysa; KRP1 plays an important role in seed development of rice, Plant Physiology, 142: 1053-1064, except for a more external position of OsKRP3. This demonstrates a clear correspondence between the wheat and rice/maize genes.

The wheat KRP homologues TaKRP1, TaKRP2, TaKRP4, TaKRP5 were named according to the rice KRP nomenclature. OsKRP1, OsKRP4, and OsKRP5 genes are expressed in the seeds. OsKRP4 is the only one that carries a consensus CDK phosphorylation site.

The sequence of KRPs from the A, B and D genomes (SEQ ID Nos 40, 41, 43, 44, 46, 47, 49, 50, 52, 53, 55, 56, 58, 59, 60, 62, 63, 64, 66, 67, 68, 70, 71, 73, 74, 76 and 77) were obtained using wheat BAC libraries.

Example 2

Genome-Specific Primers for TILLING® of Wheat KRPs

Figure 2:
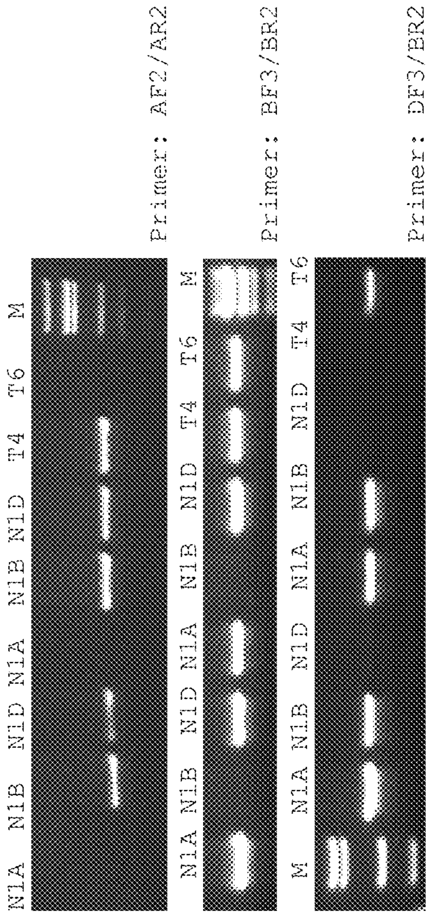
FIG. 2 depicts PCR using indicated genome-specific primers on wheat deleted for a given genome. N1A=A genome deleted. N1B=B genome deleted. N1D=D genome deleted. T4-tetraploid TILLING® line. T6=hexaploid TILLING® line.

The genome specificity of the wheat KRP primers using Chinese-Spring (CS) nulli-tetrasomic lines and TILLING® cultivars were validated. The validation for wheat KRP4 primers is shown in FIG. 2. Table 1 lists the TILLING® primer sets for each wheat KRP.

TABLE 1

TILLING ® primers for wheat KRPs

| Gene/Genome | Primer name | Primer sequence (5' to 3') | SEQ ID NO |
|---|---|---|---|
| KRP1A | Krp-A1_AF1 | GTCTGTAGAACGGCGTTACG | 6 |
| | Krp-A1_R8 | CCCCAGCTCTACAGTGAGTAACTT | 7 |
| KRP1B | Krp-B1_F5 | GGAGAGAATCCAAAGAGCAAC | 8 |
| | Krp-B1_R7 | CCAGCTCTACAGTGAGTAAC | 9 |
| KRP1D | Krp-D1_F4 | CGTGTTATATGTGTACGCACAC | 10 |
| | Krp-D1_DR2 | GGCTATAATGCTTCTTTCTGGAGC | 11 |
| KRP2A | Krp-A2_BF3 | CAAACGGCCAAAGCGACGG | 12 |
| | Krp-A2_AR3 | CTAGTGTTGCATAGTTAGCTC | 13 |
| KRP2B | Krp-B2_BF3 | CAAACGGCCAAAGCGACGG | 14 |
| | Krp-B2_BR2 | TCTCGCCTCCGAGTCTAAGT | 15 |
| KRP2D | Krp-D2_BF3 | CAAACGGCCAAAGCGACGG | 16 |
| | Krp-D2_DR1 | CAGATTTGAACAAGGTGGATC | 17 |
| KRP4A_exon1 | WKP4_AFI | TACCCGCGCCTCGCTTAAATCCGCCAAA | 18 |
| | WKP4_AR1 | GTCAACTCGTGAAAGAAGAGTTGGGACAGA | 19 |
| KRP4A_exons 2-3 | WKP4_AF2 | CCTTAGGCAAGTTCGGTAAGAAATGTGTA | 20 |
| | WKP4_AR2 | GTGGTCATTACAGAATGAGTTGCTAACCGTC | 21 |
| KRP4B_exon1 | WKP4_BF1 | TTACCCGCGCCTCGCTTAAATCCGCAAG | 22 |
| | WKP4_BR1 | GCTCAAACAGCGAAAGAAGAGTTAGACGGA | 23 |
| KRP4B_exons 2-3 | WKP4_BF3 | CTGGCCTACTCATGTGAGACTGAGAGATTA | 24 |
| | WKP4_BR2 | GTGGTCATTACAGAATGAGCTGCTAACCGTT | 25 |
| KRP4D_exon1 | WKP4_DF1 | TACCCGCCCCTCGCTTAAATCCGCCAAA | 26 |
| | WKP4_DR1 | ACTCAAATAGCGAAAGAAGAGTTAGCCAGGA | 27 |
| KRP4D_exons 2-3 | WKP4_DF3 | TGGCCTACTCATGTGACACTGAGAGATTG | 28 |
| | WKP4_BR2 | GTGGTCATTACAGAATGAGCTGCTAACCGTT | 29 |
| KRP5A_exon1 | Krp-A5_AF7 | GTAAGCACAGGAAGCAGAGC | 30 |
| | Krp-A5_AR6 | CTCAGTCGTATTCGTATCGG | 31 |
| KRP5A_exons 2-3 | Krp-A5_AF4 | CACACCTCACATTGTGTGATG | 32 |
| | Krp-A5_R1 | ACAGAGATCAATGGAGGAGC | 33 |
| KRP5B | Krp-B5_BF4 | TGCGCCTCACATTGTCTAGC | 34 |
| | Krp-A5_R1 | ACAGAGATCAATGGAGGAGC | 35 |
| KRP5D | Krp-D5_DF4 | ATGCTAGAACATGAGCTGTCG | 36 |
| | Krp-D5_DR3 | GCTGATGGTGGTGGTCATTC | 37 |

Example 3

Discovery of a Natural KRP-A4 Deletion in Hexaploid Wheat

Both sets of A genome KRP4 primers did not amplify the KRP4 gene in the hexaploid TILLING® line (FIG. 2), suggesting a possible natural deletion in the KRP4 A genome of the hexaploid TILLING® line. This was confirmed with the use of 3 gene-specific primers.

The B and D copies of KRP4 in hexaploid wheat were TILL'ed. The hexaploid mutations can easily be moved between tetraploid and hexaploid wheat by crosses.

Example 4

Wheat KRP Expression Studies

Figure 3A:
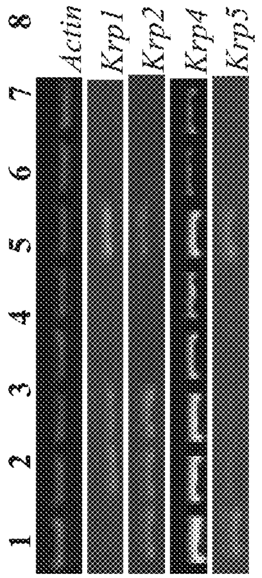
FIG. 3A and FIG. 3B depict RT-PCR on wheat KRP transcripts. RNA was extracted using a QIAGEN® kit, and cDNAs were produced with the INVITROGEN™ reverse transcription system.

To determine which KRP genes were expressed in early seed development, the transcript levels of the KRP genes were assessed by RT-PCR (FIG. 3A). These results showed that KRP4 transcript levels were higher than those of the other genes and that its transcripts accumulated over a longer developmental period than the transcripts from KRP1, KRP2, and KRP5. These last three genes were detected in the different pools from the 2-6 days after anthesis (DAA) samples and only in one out of the three pooled samples collected 8-12 DAA. No transcripts from KRP1, KRP2, and KRP5 were detected in the 14-18 DAA samples, whereas KRP4 transcripts were still abundant during this developmental stage. This data suggest that KRP4 has a different transcription profile than the other KRP genes during seed development.

Figure 3B:
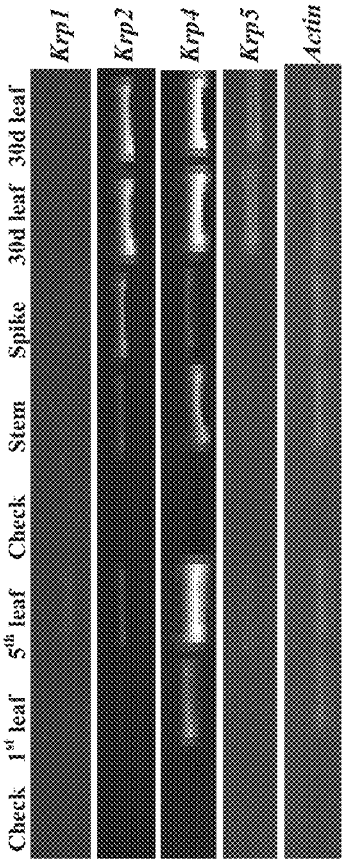

The transcript levels of these four KRP genes were determined in other tissues (FIG. 3B). Transcripts from KRP2, KRP4, and KRP5 were detected in cDNAs from 30-day old leaves. KRP1 was the only one not detected at that stage. KRP1 and KRP5 were not detected in cDNA samples from the first leaf and were very faint at the $5^{th}$ leaf-stage. Both were absent from stems and spikes. Transcripts from KRP2 and KRP4 were detected in stems and spikes.

Example 5

Mutations of *Triticum* KRP Genes Identified in TILLING®

Screening of the TILLING® population for KRP mutants resulted in plants with silent, splice, nonsense (premature stop codons) and/or missense (severe or non-severe) mutations in KRP1, KRP2, KRP4 and KRP5 (A, B, and D genomes) genes. TILLING® was conducted according to Uauy, C., F. Paraiso, et al. (2009) "A modified TILLING® approach to detect induced mutations in tetraploid and hexaploid wheat" BMC Plant Biol 9: 115.

Positions and effects of mutations in KRP1, KRP2, KRP4 and KRP5 (A, B, and D genomes) genes are provided in Tables 2-3 below (* indicates the mutation results in a stop codon, = indicates the mutation is silent).

TABLE 2

Summary of *Triticum durum* (tetraploid) KRP4A and KRP4B mutants

| KRP mutant | Nucleotide Change^ | Effect | Mutation Score |
|---|---|---|---|
| KRP4A-242 | G688A | W186* | nonsense |
| KRP4A-296 | C248T | T104I | missense |
| KRP4A-1220 | C335T | S133F | Type II§ |
| KRP4A-1031 | C994T | N176= | silent |
| KRP4B-842 | G184A | G41E | missense |
| KRP4B-309 | G277A | R72K | missense |
| KRP4B-587 | G291A | E77K | missense |
| KRP4B-650 | G407A | S111N | missense |
| KRP4B-112 | G434A | S120N | missense |
| KRP4B-161 | C440T | P122L | Type II |
| KRP4B-1280 | G461A | S129N | missense |

^Nucleotide numbering is dependent upon the location of TILLING ® primers.
§Type I and Type II mutations are defined in the wheat breeding program section.

TABLE 3

Summary of *Triticum aestivum* (hexaploid) KRP mutants

| KRP mutant | Nucleotide Change^ | Effect | Mutation Score |
|---|---|---|---|
| KRP1A-2887 | G484A | splice | splice |
| KRP1B-2371 | C293T | S98L | missense |
| KRP1B-2201 | G585A | S144N | missense |
| KRP1B-2199 | C657T | S156F | Type II§ |
| KRP1D-2259 | C181T | Q61* | nonsense |
| KRP2A-2241 | G758A | splice | splice |
| KRP2B-3004 | C775T | S179L | missense |
| KRP2D-0905 | C29T | A10V | missense |
| KRP4B-2023 | G321A | E87K | missense |
| KRP4B-149 | C401T | P109L | Type II |
| KRP4B-491 | G496A | A141T | missense |
| KRP4B-823 | G390A | R105= | silent |
| KRP4B-566 | G399A | T108= | silent |
| KRP4D-586 | G387A | splice | splice |
| KRP4D-404 | C407T | P109S | Type II |
| KRP4D-557 | C814T | L180S | Type I |
| KRP4D-558 | C563T | P161S | missense |
| KRP5A-2327 | G1910A | G141R | Type II |
| KRP5A-802 | | P43S | missense |
| KRP5A-2506 | | E89K | missense |
| KRP5D-425 | C1770T | S138L | missense |
| KRP5D-2194 | C2044T | P194L | Type I |

^Nucleotide numbering is dependent upon the location of TILLING ® primers.
§Type I and Type II mutations are defined in the wheat breeding program section.

Example 6

Wheat Breeding Program

The wheat KRP TILLING® mutants are prioritized for the breeding program from most important to less important in the following manner: 1) Nonsense and splice mutants, 2) Type I severe missense, 3) Type II severe missense. Type I severe missense mutations are non-conservative amino acid substitutions in regions of the KRP protein known to be essential for binding to cyclin or cyclin-dependent kinase (CDK) and are predicted by SIFT (Sorting Intolerant From Tolerant) analysis (Ng and Henikoff, SIFT: predicting amino acid changes that affect protein function, Nucl. Acids Res. (2003) 31 (13): 3812-3814) to be deleterious to protein function. Type II severe missense mutations are non-conservative amino acid substitutions outside of the cyclin and CDK binding domains but which satisfy two additional criteria. First, they are in regions of the protein determined by BLOCKS analysis (Henikof S. and Henikoff J. G. (1991) *Nucleic Acids Res.,* 19, 6565-6572) to be evolutionarily conserved and therefore possibly of functional significance. Secondly, they have a SIFT (Ng, P. C. and Henikof S. (2003) *Nucleic Acids Res. July* 1; 31(13): 3812-3814) score of less than 0.05, and are therefore predicted to be deleterious to protein function.

M3 seed homozygous or heterozygous for a given KRP TILLING® mutation is grown. Backcrosses with the hexaploid spring wheat background parent are performed, ideally through several rounds (to the BC3 or BC4 level), to eliminate deleterious background mutations. Background mutations could contribute to undesirable traits such as delayed maturity, premature senescence, increased susceptibility to wheat pathogens, slow germination, and/or sterility. The progeny of each backcross (F1, BC1, BC2, etc.) are also selfed to produce F2 lines. F2 lines are genotyped to identify ones that are homozygous for the wild type or for the krp mutant allele. Homozygote wild type and mutant siblings are seed expanded to F3 for field trials.

Wheat krp mutant alleles are introgressed into other spring and winter wheat lines to transfer the yield enhancement to commercial varieties.

Crosses between mutants are done to generate multiple stack mutants within a given KRP gene (e.g. KRP1A/1B, KRP1B/KRP1D, KRP1A/1B/1D, etc., all possible combinations) or across different KRP genes (e.g. KRP1A/2A, KRP2B/KRP4B, KRP4D/KRP5A, KRP1B/KRP2A/KRP5D, etc., all possible combinations).

The overall grain yield per unit area is determined (e.g. lbs/acre) and yield components such as seed count, seed size/weight (thousand kernel weight), seed per spike, head (spike) number, spike length, awn length, and/or tiller number, are measured. Agronomic characteristics such as stand rate, maturity rate and peduncle rate are also measured.

Example 7

Characterization of Hexaploid TILLING® Mutant KRP4B-149

Hexaploid mutant line KRP4B-149 was backcrossed to the non-mutagenized recurrent parent to reduce the mutation load. $BC_1F_2$ lines (backcrossed once and selfed) homozygous for the presence of the mutation were selected. In addition, a KRP4B-149 sibling line homozygous for the lack of the mutation was used as a control.

Plants were grown in outside field plots in California. The experiment was organized in a Complete Randomized Block Design (RCBD) with four replications. Differences between the individual mutants and the single control line were tested using the Dunnett test. The following parameters were measured: heading time, height, number of spikelets per spike, grains per spike, thousand kernel weight (TKW) and yield.

While early reports indicate that the KRP4B-149 mutant grew faster and flowered earlier, later reports for the KRP4B-149 mutant showed no-significant differences for most of the parameters except for a 10 days delay in flowering time (P=0.0003) and a slight increase in two spikelets per spike (P=0.006) which was not reflected in an increase in the number of grains or in grain yield. However, the delay in flowering time was not seen in the BC2F2 generation in the greenhouse.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

1. Bentley, A., B. MacLennan, et al. (2000). "Targeted Recovery of Mutations in *Drosophila*." Genetics 156: 1169-1173.
2. Comai, L. and S. Henikoff (2006). "TILLING: practical single-nucleotide mutation discovery." Plant J 45(4): 684-94.
3. Comai, L., K. Young, et al. (2004). "Efficient discovery of DNA polymorphisms in natural populations by Ecotilling." Plant J 37(5): 778-86.
4. Cooper, J. L., E. A. Greene, et al. (2008). "Retention of induced mutations in a *Drosophila* reverse-genetic resource." Genetics 180(1): 661-7.
5. Cooper, J. L., B. J. Till, et al. (2008). "Fly-TILL: reverse genetics using a living point mutation resource." Fly (Austin) 2(6): 300-2.
6. Cooper, J. L., B. J. Till, et al. (2008). "TILLING to detect induced mutations in soybean." BMC Plant Biol 8: 9.
7. Eddy, S. R. (2004). "Where did the BLOSUM62 alignment score matrix come from?" Nat Biotechnol 22(8): 1035-6.
8. Gilchrist, E. and G. Haughn "Reverse genetics techniques: engineering loss and gain of gene function in plants." Brief Funct Genomics 9(2): 103-10, 20107
9. Gilchrist, E. J. and G. W. Haughn (2005). "TILLING without a plough: a new method with applications for reverse genetics." Curr Opin Plant Biol 8(2): 211-5.
10. Gilchrist, E. J., G. W. Haughn, et al. (2006). "Use of EcoTILLING as an efficient SNP discovery tool to survey genetic variation in wild populations of *Populus trichocarpa*." Mol Ecol 15(5): 1367-78.
11. Gilchrist, E. J., N. J. O'Neil, et al. (2006). "TILLING is an effective reverse genetics technique for *Caenorhabditis elegans*." BMC Genomics 7: 262.
12. Greene, E. A., C. A. Codomo, et al. (2003). "Spectrum of chemically induced mutations from a large-scale reverse-genetic screen in *Arabidopsis*." Genetics 164(2): 731-40.
13. Henikoff, S., B. J. Till, et al. (2004). "TILLING. Traditional mutagenesis meets functional genomics." Plant Physiol 135(2): 630-6.
14. Himelblau, E., E. J. Gilchrist, et al. (2009). "Forward and reverse genetics of rapid-cycling *Brassica oleracea*." Theor Appl Genet 118(5): 953-61.
15. McCallum, C. M., L. Comai, et al. (2000). "Targeted screening for induced mutations." Nat Biotechnol 18(4): 455-7. (referenced in Anawah patents)
16. McCallum, C. M., L. Comai, et al. (2000). "Targeting induced local lesions IN genomes (TILLING) for plant functional genomics." Plant Physiol 123(2): 439-42. (referenced in Anawah patents)
17. Ng, P. C. and S. Henikoff (2003). "SIFT: Predicting amino acid changes that affect protein function." Nucleic Acids Res 31(13): 3812-4.
18. Slade, A. J., S. I. Fuerstenberg, et al. (2005). "A reverse genetic, nontransgenic approach to wheat crop improvement by TILLING." Nat Biotechnol 23(1): 75-81.
19. Slade, A. J. and V. C. Knauf (2005). "TILLING moves beyond functional genomics into crop improvement." Transgenic Res 14(2): 109-15.
20. Stemple, D. L. (2004). "TILLING—a high-throughput harvest for functional genomics." Nat Rev Genet 5(2): 145-50.
21. Styczynski, M. P., K. L. Jensen, et al. (2008). "BLOSUM62 miscalculations improve search performance." Nat Biotechnol 26(3): 274-5.
22. Talame, V., R. Bovina, et al. (2008). "TILLMore, a resource for the discovery of chemically induced mutants in barley." Plant Biotechnol J 6(5): 477-85.
23. Taylor, N. E. and E. A. Greene (2003). "PARSESNP: A tool for the analysis of nucleotide polymorphisms." Nucleic Acids Res 31(13): 3808-11.
24. Till, B. J., C. Burtner, et al. (2004). "Mismatch cleavage by single-strand specific nucleases." Nucleic Acids Res 32(8): 2632-41.
25. Till, B. J., T. Colbert, et al. (2006). "High-throughput TILLING for *Arabidopsis*." Methods Mol Biol 323: 127-35.
26. Till, B. J., T. Colbert, et al. (2003). "High-throughput TILLING for functional genomics." Methods Mol Biol 236: 205-20.
27. Till, B. J., J. Cooper, et al. (2007). "Discovery of chemically induced mutations in rice by TILLING." BMC Plant Biol 7: 19.
28. Till, B. J., S. H. Reynolds, et al. (2003). "Large-scale discovery of induced point mutations with high-throughput TILLING." Genome Res 13(3): 524-30.
29. Till, B. J., S. H. Reynolds, et al. (2004). "Discovery of induced point mutations in maize genes by TILLING." BMC Plant Biol 4: 12.
30. Till, B. J., T. Zerr, et al. (2006). "A protocol for TILLING and EcoTILLING in plants and animals." Nat Protoc 1(5): 2465-77.
31. Triques, K., E. Piednoir, et al. (2008). "Mutation detection using ENDO1: application to disease diagnostics in humans and TILLING and Eco-TILLING in plants." BMC Mol Biol 9: 42.

32. Triques, K., B. Sturbois, et al. (2007). "Characterization of *Arabidopsis thaliana* mismatch specific endonucleases: application to mutation discovery by TILLING in pea." Plant J 51(6): 1116-25.
33. Uauy, C., F. Paraiso, et al. (2009). "A modified TILLING approach to detect induced mutations in tetraploid and hexaploid wheat." BMC Plant Biol 9: 115.
34. Weil, C. F. and R. Monde (2007). "Getting the Point-Mutations in Maize." Crop Science 47 (S1)(No. 1): S-60-67.
35a. Zerr, T. and S. Henikoff (2005). "Automated band mapping in electrophoretic gel images using background information." Nucleic Acids Res 33(9): 2806-12.
35b. Tsai, H. et al. (2011), Discovery of Rare Mutations in Populations: TILLING by Sequencing, Plant Physiology, 156(3): 1257-1268
36. Slafer and Araus (2007), Springer, "Physiological traits for improving wheat yield under a wide range of conditions", Scale and Complexity in Plant Systems Research: Gene-Plant-Crop Relations, 147-156
37. Reynolds, "Physiological approaches to wheat breeding", *Agriculture and Consumer Protection*. Food and Agriculture Organization of the United Nations.
38. Richard et al., "Physiological Traits to Improve the Yield of Rainfed Wheat: Can Molecular Genetics Help", published by International Maize and Wheat Improvement Center.
39. Reynolds et al., "Evaluating Potential Genetic Gains in Wheat Associated with Stress-Adaptive Trait Expression in Elite Genetic Resources under Drought and Heat Stress Crop science", Crop Science 2007 47: Supplement_3: S-172-S-189
40. Setter et al., Review of wheat improvement for waterlogging tolerance in Australia and India: the importance of anaerobiosis and element toxicities associated with different soils. Annals of Botany, Volume 103(2): 221-235.
41. M. J. Foulkes, N. D. Paveley, A. Worland, S. J. Welham, J. Thomas, J. W. Snape. Major Genetic Changes in Wheat with Potential to Affect Disease Tolerance. Phytopathology, July, Volume 96, Number 7, Pages 680-688 (doi: 10.1094/PHYTO-96-0680)
42. Rosyara, U. R., K. Pant, E. Duveiller and R. C. Sharma. 2007. Variation in chlorophyll content, anatomical traits and agronomic performance of wheat genotypes differing in spot blotch resistance under natural epiphytotic conditions. Australasian Plant Pathology 36: 245-251.
43. Rosyara, U. R., R. C. Sharma, and E. Duveiller. 2006. Variation of canopy temperature depression and chlorophyll content in spring wheat genotypes and association with foliar blight resistance. J. Plant Breed. Gr. 1: 45-52.
44. Rosyara, U. R., R. C. Sharma, S. M. Shrestha, and E. Duveiller. 2005. Canopy temperature depression and its association with *helminthosporium* leaf blight resistance in spring wheat. Journal of Institute of Agriculture and Animal Science 26: 25-28.
45. Rosyara, U. R., R. C. Sharma, S. M. Shrestha, and E. Duveiller. 2006. Yield and yield components response to defoliation of spring wheat genotypes with different level of resistance to *Helminthosporium* leaf blight. Journal of Institute of Agriculture and Animal Science 27, 42-48.
46. Rosyara, U. R. 2002. Physio-morphological traits associated with *Helminthosporium* leaf blight resistance in spring wheat. Masters' Thesis. Tribhuvan University, Institute of Agriculture and Animal Science, Rampur, Chitwan, Nepal. supported by C1MMYT International. Available at CIMMYT library
47. Hayward, M. D., N. O. Bosemark, and I. Romangosa. 1993. Plant Breeding: Principle and Prospects. Chapman and Hall, London.
48. Wood, D. R., K. M. Rawal, and M. N. Wood (eds). 1983. Crop Breeding. American Society of Agronomy, Crop Science Society of America, Madison, Wis.
49. Allard, R. W. 1960. Principles of Plant Breeding. John Wily and Sons Inc. New York.
50. Simmonds, N. W. 1979. Principles of Crop Improvement. Longman Group Limited, London.
51. Singh, B. D. 2000. Plant Breeding. Sixth ED. Kalyani Publishers, New Delhi.
52. Guo et al., 2005, American Journal of Botany 92(9): 1548-1558.
53. Watson et al. 1999. Grass genera of the world: descriptions, illustrations, identification, and information retrieval; including synonyms, morphology, anatomy, physiology, phytochemistry, cytology, classification, pathogens, world and local distribution, and references. Version: 18 Aug. 1999,
54. GPWG. 2001. Phylogeny and subfamilial classification of the grasses (Poaceae). Annals of the Missouri Botanical Garden 88: 373-457.
55. Clayton et al., 1986. Genera *Graminum*. Kew Bulletin Additional Series XIII: 1-389.
56. Xia, Progress of chromosome engineering mediated by asymmetric somatic hybridization., J Genet Genomics. 2009 September; 36(9):547-56. Review.
57. Liu et al., Generation of high frequency of novel alleles of the high molecular weight glutenin in somatic hybridization between bread wheat and tall wheatgrass. Theor Appl Genet. 2009 April, 118(6):1193-8. Epub 2009 Feb. 8.
58. Zhou et al., Comparative study of symmetric and asymmetric somatic hybridization between common wheat and *Haynaldia villosa*. Sci China C Life Sci. 2001 June; 44(3):294-304.
59. Wang et al., Proteomic analysis on a high salt tolerance introgression strain of *Triticum aestivum/Thinopyrum ponticum*. Proteomics. 2008 Apr.; 8(7):1470-89.
60. Cai et al., Genotyping of somatic hybrids between *Festuca arundinacea* Schreb. and *Triticum aestivum* L., Plant Cell Rep. 2007 Oct.; 26(10):1809-19. Epub 2007 Jun. 27.
61. Deng et al., Analysis of remote asymmetric somatic hybrids between common wheat and *Arabidopsis thaliana*., Plant Cell Rep. 2007 Aug.; 26(8):1233-41. Epub 2007 Apr. 4.
62. Zhou et al., Genetic characterization of asymmetric somatic hybrids between *Bupleurum scorzonerifolium* Willd and *Triticum aestivum* L.: potential application to the study of the wheat genome. Planta. 2006 March,223 (4):714-24. Epub 2005 Nov. 4.
63. Li et al., Regeneration of asymmetric somatic hybrid plants from the fusion of two types of wheat with Russian wildrye. Plant Cell Rep. 2004 Dec.; 23(7):461-7. Epub 2004 Jul. 24.
64. Zhou et al., Introgression of the *Haynaldia villosa* genome into gamma-ray-induced asymmetric somatic hybrids of wheat. Plant Cell Rep. 2005 Jul.; 24(5):289-96. Epub 2005 Jun. 3.
65. X. Hu, X. Cheng, H. Jiang, S. Zhu, B. Cheng and Y. Xiang, (2010), Genome-wide analysis of cyclins in maize (*Zea mays*), Genet. Mol. Res. 9 (3): 1490-1503
66. Acquaah et al. Principles of plant genetics and breeding, Wiley-Blackwell, 2007, ISBN 1405136464, 9781405136464

67. Harten, Mutation Breeding, Cambridge University Press, 1998.

68. Roy Davies and Wall, "Artificial Mutagenesis in Plant Breeding", Nature 182, 955-956 (4 Oct. 1958)

69. Grotewold, Plant Functional Genomics, Volume 236 of Methods in molecular biology, Humana Press, ISBN 1588291456, 9781588291455

70. Braman, In vitro mutagenesis protocols, Volume 182 of Methods in molecular biology, Human Press, 2002, ISBN 0896039102, 9780896039100

71. Chusacultanachai et al., "Random mutagenesis strategies for construction of large and diverse clone libraries of mutated DNA fragments." Methods Mol Biol. 2004; 270:319-34.

72. Fujii et al., One-step random mutagenesis by error-prone rolling circle amplification, Nucl. Acids Res. (2004) 32 (19): e145.

73. Trower, In vitro mutagenesis protocols, Volume 57 of Methods in molecular biology, John M. Walker Methods in molecular biology (Clifton, N.J.) 57, ISBN 0896033325, 9780896033320

74. Katsumi, M., Foard, D. E. and Phinney, B. O. (1983) Evidence for the translocation of gibberellin A3 and gibberellin-like substances in grafts between normal, dwarf1 and dwarf5 seedlings of *Zea mays* L. Plant Cell Physiol. 24, 379-388.

75. Lacadena, J.-R. Hybrid wheat. VII. Tests on the transmission of cytoplasmic male sterility in wheat by embryo-endosperm grafting, Euphytica, 17(3), 439-444

76. Trione et al., 1968, IN VITRO CULTURE OF SOMATIC WHEAT CALLUS TISSUE American Journal of Botany, Vol. 55, No. 5, May-June, 19

77. Dodig, et al., tissue culture response of different wheat genotypes, environmental effect and association with plant traits, Options MEditerraneennes, Series A, No. 81, pages 129 to 132

78. O'HARA et al., Wheat Callus Culture: the Initiation, Growth and Organogenesis of Callus Derived from Various Explant Sources Ann Bot (1978) 42 (5): 1029-1978.

79. Zaidi et al., Optimizing tissue culture media for efficient transformation of different indica rice genotypes Agronomy Research 4(2):563-575, 2006

80. Wang et al., Tissue Culture Responses from Different Explants of Rice, Rice Science, 2005, 12(3): 229-232

81. Ting Y, Boyer A, McSweeney G (1978) Maize tissue culture. MNL 52:6

82. Martha C. Hawes, Diana Z. Sharpe, Maria-Ines Plata, Steven G. Pueppke, Prem S. Chourey, Auxin-independent growth of maize tissue culture cells, Plant Science, Volume 40, Issue 3, September 1985, Pages 197-202

83. SHERIDAN Tissue Culture of Maize, Physiologia Plantarum, 41(3):172-174, 1977

---

SEQUENCE LISTING

SEQ ID NO: 1

>TaKrp1A (3′ end missing)

MGKYMRKCRAEDGAVGGVEVTQAVGVRTRSRAAAANVVVSKRRRPLPPGSPSASSSLARAQGGSCYLKLRSRMLF

MAPPAPASGAAAGHGPAPPLPAGLSRCSSTASSVDASAAAQDRSLPS

SEQ ID NO: 2

>TaKrp2

LGVRTRSRAGARDAKMRKQQQATTSTAARAVEDALLGRDGGDAAAGCYLHLRSRRLFMPAAAVVDRGGGGGLCEE

ASTAGLPDSGPSVEAAVGAGVSRCSSTVSTAVDVAARERSGDEAEACESRDVESSVSDEECGGRDRRETTPSSRS

PVDLSDLESSQAADEQKHKRRRCPATTTTTAAPLHYDLEARARARMPPAAEIDEFFAAAEKAQAERFAAKYNFDV

ARGVPLNAGRFEWTPVATV*

SEQ ID NO: 3

>TaKrp4 *Triticum aestivum* EST

MGKYMRKPKVSGEVAVMEVAAAPLGVRTRARALAMQRQPQGAAVAKDQGEYLELRSRKLEKLPPPPPAARRRAAA

AERVEAEAEADEVSFGENVLESEAMG*GTRETTPCSLIRDSGTISTPGSTTRPSHSNSHRRVQAPARHIIPCSAE

**MNEFFSAAEQPQQQAFID*YNFDPVNDCPLPGRYEWVKLD***

SEQ ID NO: 4

>TuKrp4 *Triticum urartu* A GENOME

MGKYMRKPKVSGEVAVMEVAAAPLGVRTRARALAMQRQPQGAPGAKDQGEYLELRSRKLEKLPPPPPPARRRAAA

AERVEAEAEADKVSFGENVLEPEAMG*GTRETTPCSLIRDSGMISTPGSTTRPSHSNSHRRVQAPARHIIPSSAE

**MNEFFSAAEQPQQQAFID*YNFDPVNDCPLPGRYEWVKLD***

SEQ ID NO: 5

>TaKrp5 (5′ end missing)

xxxxxxxxxxxxxxxxxxxxxxxxxxxxxxxxxxxxxxxxxxxxxxxxxxxxxxxxxxxxxxxxxxxxxxxxxxx xxxGTRKEKGDAPQPAARRAAAAGGRGMESFAAEGFEADLEVSFGDNVLDWDATDRGARETTPCSLIYSSETMST

PGSATGARNHSRRRAQTPVCRYVPSSLEMDEFFAAAEQQQHQTFREKYNECPASERPLPGRYEWTVLDC*

-continued

SEQ ID NO: 6
Krp-A1_AF1
GTCTGTAGAACGGCGTTACE

SEQ ID NO: 7
Krp-A1_R8
CCCCAGCTCTACAGTGAGTAACTT

SEQ ID NO: 8
Krp-B1_F5
GGAGAGAATCCAAAGAGCAAC

SEQ ID NO: 9
Krp-B1_R7
CCAGCTCTACAGTGAGTAAC

SEQ ID NO: 10
Krp-D1_F4
CGTGTTATATGTGTACGCACAC

SEQ ID NO: 11
Krp-D1_DR2
GGCTATAATGCTTCTTTCTGGAGC

SEQ ID NO: 12
Krp-A2_BF3
CAAACGGCCAAAGCGACGG

SEQ ID NO: 13
Krp-A2_AR3
CTAGTGTTGCATAGTTAGCTC

SEQ ID NO: 14
Krp-B2_BF3
CAAACGGCCAAAGCGACGG

SEQ ID NO: 15
Krp-B2_BR2
TCTCGCCTCCGAGTCTAAGT

SEQ ID NO: 16
Krp-D2_BF3
CAAACGGCCAAAGCGACGG

SEQ ID NO: 17
Krp-D2_DR1
CAGATTTGAACAAGGTGGATZ

SEQ ID NO: 18
WKP4_AF1
TACCCGCGCCTCGCTTAAATCCGCCAAA

SEQ ID NO: 19
WKP4_AR1
GTCAACTCGTGAAAGAAGAGTTGGGACAGA

SEQ ID NO: 20
WKP4_AF2
CCTTAGGCAAGTTCGGTAAGAAATGTGTA

SEQ ID NO: 21
WKP4_AR2
GTGGTCATTACAGAATGAGTTGCTAACCGTC

SEQ ID NO: 22
WKP4_BF1
TTACCCGCGCCTCGCTTAKATCCGCAAG

SEQ ID NO: 23
WKP4_BR1
GCTCAAACAGCGAAAGAAEAGTTAGACGGA

SEQ ID NO: 24
WKP4_BF3
CTGGCCTACTCATGTGAGACTGAGAGATTA

-continued

SEQ ID NO: 25
WKP4_BR2
GTGGTCATTACAGAATGAGCTGCTAACCGTT

SEQ ID NO: 26
WKP4_DF1
TACCCGCCCCTCGCTTAAATCCGCCAAA

SEQ ID NO: 27
WKP4_DR1
ACTCAAATAGCGAAAGAAGAGTTAGCCAGGA

SEQ ID NO: 28
WKP4_DF3
TGGCCTACTCATGTGACACTGAGAGATTG

SEQ ID NO: 29
WKP4_BR2
GTGGTCATTACAGAATGAGCTGCTAACCGTT

SEQ ID NO: 30
Krp-A5_AF7
GTAAGCACAGGAAGCAGAGC

SEQ ID NO: 31
Krp-A5_AR6
CTCAGTCGTATTCGTATCGG

SEQ ID NO: 32
Krp-A5_AF4
CACACCTCACATTGTGTGATG

SEQ ID NO: 33
Krp-A5_R1
ACAGAGATCAATGGAGGAGC

SEQ ID NO: 34
Krp-B5_BF4
TGCGCCTCACATTGTCTAGC

SEQ ID NO: 35
Krp-A5_R1
ACAGAGATCAATGGAGGAGC

SEQ ID NO: 36
Krp-D5_DF4
ATGCTAGAACATGAGCTGTCG

SEQ ID NO: 37
Krp-D5_DR3
GCTGATGGTGGTGGTCATTC

SEQ ID NO: 38
>BQ578371.1 Wheat unstressed seedling shoot cDNA *T. aestivum*
AGCAGCCCAGCGGCATCATACCCCTCCCTCCCACCCACCGGCGCCGCGCTGCAGACGCAAACGGCCAAAGGCGAG

CGGCGTGGGGCGGAGCGCGGGGCAATGGGGAAGTACATGCGCAAGTGCAGGGCGGAGGACGGCGCGGTGGGCGGC

GTGGAGGTCACGCAGGCCGTCGGCGTCCGCACCCGGTCCCGCGCGGCCGCGGCCAACGTCGTCGTCTCCAAGAGG

AGGCGCCCGCTGCCGCCCGGCTCGCCGTCGGCCTCGTCGTCCCTCGCTCGCGCCCAGGGCGGGAGCTGCTACCTG

AAGCTGCGGAGCCGCATGCTGTTCATGGCCCCGCCGGCGCCCGCATCGGGGGCTGCCGCCGGGCACGGGCCGGCG

CCGCCGCTCCCGGCCGGCCTGTCGCGCTGCTCCAGCACGGCGTCGTCCGTGGACGCGTCGGCCGCGGCGCAGGAC

AGGAGCCTGCCCTCGTG

SEQ ID NO: 39
>OsKrp1 DQ229362 *Oryza sativa*
MGKYMRKFRGATGEELAAMEVTQVVGVRTRSRSAAAAGATTTKVKAASAASTRRRKALLPTAVVGTTRRDGGSCY

LQLRSRMLFMAPPRPAPAARAPVVAEAAGSGNGAAAHAAAGLSRCSSTASSVDAAAQDRSLACRSDVAE

AGSEHVPEGSASDSASGRDRERRETTPSSFLPGEVSDLESDLAGGQKRSRPLPSAATASAQQATRPKI

PPAAEIEAFFAAAEEAEAKRFAAKYNEDVVRGVPLDAGRFEWTPVVSSRS*

-continued

SEQ ID NO: 40

>wheat KRP1A genomic
CCTGGGCGTCGGATCGGGACCCGATCCCCCGGCTCCCCCCTTGGCGTGTTATATGCGTACGCACCCAC
GCGCACGGGGCGCACTCCGGACGGGGGAGAGAATCCAAAGAGCAGCCCAGCGGCATCATACCCCTCCC
TCCCACCCACCGGCGCCGCGCTGCAGACGCAAACGGCCAAAGGCGAGCGGCGTGGGGCGGAGCGCGGG
GCGATGGGGAAGTACATGCGCAAGTGCAGGGCGGAGGACGGCGCGGTGGGCGGCGTGGAGGTCACGCA
GGCCGTCGGCGTCCGCACCCGGTCCCGCGCGGCCGCGGCCAACGTCGTCGTCTCCAAGAGGAGGCGCC
CGCTGCCGCCCGGCTCGCCGTCGGCCTCGTCGTCCCTCGCTCGCGCCCAGGGCGGGAGCTGCTACCTG
AAGCTGCGGAGCCGCATGCTGTTCATGGCCCCGCCGGCGCCCGCATCGGGGGCTGCCGCCGGGCACGG
GCCGGCGCCGCCGCTCCCGGCCGGCCTGTCGCGCTGCTCCAGCACGGCGTCGTCCGTGGACGCGTCGG
CCGCGGCGCAGGACAGGAGCCTGCTCTCGTGCGGCTCCGACGCCGCTGCCAACAACAAGGTGAGGGAA
TTGGGTCCAAACCCTAGAATTCGGATACGATTCGAGATCTCCTTTTTGACCGAAACCCGTGTCTTTCT
CCGCTCTGCAGGCAGGCGCCCCGGAGGGCTCGGCGAGCAACAACGCGGAGAGCGGCGGCAACCGCGAG
AGGTGCGAGATCGAATTCCGTCTTCTTTCCAGCGAATTCTTGTGAATTATGCCTCCTGCCGTGCTCCT
GACCCCGTCCCGCTCGCCGTTTTTGAAAATTCAGGCGAGAGACGACGCCGTCCAGCCATTTCCCCGGC
GACCTGAGCGACCTGGAGTCGGATCTGGCGGGGCAGAACAGCGGCCGGTCGTCGCTGCCGCAAACGCC
GACCGCCCAGGCCCAGCCCGCCGCGAGGTCGAGGGTCCCGCCGGCGGCCGAGATCGAGGAGTTCTTCG
CGGCCGCCGAGGAGGCCGAGGCCAGGCGGTTCGCTTGCAAGTAAGTGCTTTTAGCAGCAGCGGAAACT
CTAATTCTCCACTTCGTCGCCGGAGTTCTAACGTGAGAGCTTTCTCTCGCCGTGGCCAGGTACAACTT
CGACGTGGCCCGCGGCGTGCCGCTCGGCTCCGGCCGCTACGAGTGGACCCCGGCGGTGAGCAGCAGCT
AGGCAGGCGACGAAAGCGGGCGTGCAAAGGGGGGAGAGAAGCCGTAGCTAGAAAGTTACTCACTGTAG
AGCTGGGGCGCCGGCCGGCCGGCCGGCCGTGTAGAAAGGCCAAGGGAAAAAGATGCTCCGGAAAGAAG
AAAAGAAGCATTATAGCCTAACCAACCAACCAACCACCGATCATCAACAA

SEQ ID NO: 41

>wheat KRP1A coding
ATGGGGAAGTACATGCGCAAGTGCAGGGCGGAGGACGGCGCGGTGGGCGGCGTGGAGGTCACGCAGGC
CGTCGGCGTCCGCACCCGGTCCCGCGCGGCCGCGGCCAACGTCGTCGTCTCCAAGAGGAGGCGCCCGC
TGCCGCCCGGCTCGCCGTCGGCCTCGTCGTCCCTCGCTCGCGCCCAGGGCGGGAGCTGCTACCTGAAG
CTGCGGAGCCGCATGCTGTTCATGGCCCCGCCGGCGCCCGCATCGGGGGCTGCCGCCGGGCACGGGCC
GGCGCCGCCGCTCCCGGCCGGCCTGTCGCGCTGCTCCAGCACGGCGTCGTCCGTGGACGCGTCGGCCG
CGGCGCAGGACAGGAGCCTGCTCTCGTGCGGCTCCGACGCCGCTGCCAACAACAAGGCAGGCGCCCCG
GAGGGCTCGGCGAGCAACAACGCGGAGAGCGGCGGCAACCGCGAGAGGCGAGAGACGACGCCGTCCAG
CCATTTCCCCGGCGACCTGAGCGACCTGGAGTCGGATCTGGCGGGGCAGAACAGCGGCCGGTCGTCGC
TGCCGCAAACGCCGACCGCCCAGGCCCAGCCCGCCGCGAGGTCGAGGGTCCCGCCGGCGGCCGAGATC
GAGGAGTTCTTCGCGGCCGCCGAGGAGGCCGAGGCCAGGCGGTTCGCTTGCAAGTACAACTTCGACGT
GGCCCGCGGCGTGCCGCTCGACTCCGGCCGGTACGAGTGGACCCCGGCGGTGAGCAGCAGCTAG

SEQ ID NO: 42

>wheat KRP1A protein
M G K Y M R K C R A E D G A V G G V E V T Q A V G V R T R S R A A A
A N V V V S K R R R P L P P G S P S A S S S L A R A Q G G S C Y L K
L R S R M L F M A P P A P A S G A A A G H G P A P P L P A G L S R C
S S T A S S V D A S A A A Q D R S L L S C G S D A A A N N K A G A P -continued

E G S A S N N A E S G G N R E R R E T T P S S H F P G D L S D L E S

D L A G Q N S G R S S L P Q T P T A Q A Q P A A R S R V P P A A E I

E E F F A A A E E A E A R R F A C K Y N F D V A R G V P L G S G R Y

E W T P A V S S S

SEQ ID NO: 43

>wheat KRP1B genomic

CGCGCTGCGCACTGCAGACGGAAACGGCCAAAGGAGGGCAGGCAGGAGCGCGGCGTGGGGCGATGG

GGAAGTACATGCGCAAGTGCAGGGCGGAGGACGGCGTGGGCGGCGTGGAGGTCACGCAGGCCGTCGGC

GTCCGGACCCGGTCGCGGGCGGCCGCGGCCAACGTCGTCGTTTCCAAGAGGAGGCGGCCGCTGCCGCC

AAGCTCGCCCCTCGGCGGCGCCGCCGCTCGCGCCCAGAGCGGGAGCTGCTACCTGAAGCTGCGGAGCC

GCATGCTGTTCATGGCCCCGCCGGCGCCTGCATCGGCTGCTGGCCCAGGGCACAGGCCGGCGCCGCCG

CTCCCGGCGGGCCTCTCGCGCTGCTCCAGCACGGCGTCGTCCGTGGACGCGTCGGCCGCGGGACAGGA

TAGGAGCCTGCCGTCGTGCGGCTCCGACGCCGCTGCAAACAGCAAGGTGAGGGAATTGGGGTCCAAAC

CCTAGAGTTCGGATACGATTCGAGATCTCCTTTTTTTGCTGAAAATCGTGGCTTTCTCCGCTCTACAG

GCAGGCGCTCCGGAGGGCTCAGCAAGCAACAACGCGGAGAGCGGCGGCAACCGCGAGAGGTGCGAGAT

CGAATTCCCTCCTGTCTCCGGCCAATTCTTGTGAATTATGCCTCCTGACGTGCTCCTGACCCCGTCCC

GCTCGTCGCTTTTGAAAATTCAGGCGAGAGACGACGCCGTCCAGCCATTTCCCCGGCGACCTGAGCGA

CCTGGAGTCGGATCTGGCGGGCCAGAACAGCGGCCGGTCGTCGCTGCCGCAAACGCCGACCGCCCAGG

TCCAGCCGGCCGCGAGGTCGAGGATCCCGCCGGCGGCCGAGATCGAGGAGTTCTTCGCGGCCGCCGAG

GAGGCCGAGGCCAGGCGCTTCGCTTGCAAGTAAGTACTTTAGCAGCAGCGGAAATTTCCTTATCTTGC

GGCCGCCGTCGCCGTCGCCGGAATTCTAACGTGCGAGCTCTCTGTGCCAGCTACAACTTCGACGTGGC

CCGCGGCGTGCCTCTCGACTCCGGCCGGTACGAGTGGACCCCGGCGCTGAGCAGCAACTAGCCAGCCG

AGAAAGC

SEQ ID NO: 44

>wheat KRP1B coding

ATGGGGAAGTACATGCGCAAGTGCAGGGCGGAGGACGGCGTGGGCGGCGTGGAGGTCACGCAGGCCGT

CGGCGTCCGGACCCGGTCGCGGGCGGCCGCGGCCAACGTCGTCGTTTCCAAGAGGAGGCGGCCGCTGC

CGCCAAGCTCGCCCCTCGGCGGCGCCGCCGCTCGCGCCCAGAGCGGGAGCTGCTACCTGAAGCTGCGG

AGCCGCATGCTGTTCATGGCCCCGCCGGCGCCTGCATCGGCTGCTGGCCCAGGGCACAGGCCGGCGCC

GCCGCTCCCGGCGGGCCTCTCGCGCTGCTCCAGCACGGCGTCGTCCGTGGACGCGTCGGCCGCGGGAC

AGGATAGGAGCCTGCCGTCGTGCGGCTCCGACGCCGCTGCAAACAGCAAGGCAGGCGCTCCGGAGGGC

TCAGCAAGCAACAACGCGGAGAGCGGCGGCAACCGCGAGAGGCGAGAGACGACGCCGTCCAGCCATTT

CCCCGGCGACCTGAGCGACCTGGAGTCGGATCTGGCGGGCCAGAACAGCGGCCGGTCGTCGCTGCCGC

AAACGCCGACCGCCCAGGTCCAGCCGGCCGCGAGGTCGAGGATCCCGCCGGCGGCCGAGATCGAGGAG

TTCTTCGCGGCCGCCGAGGAGGCCGAGGCCAGGCGCTTCGCTTGCAAGTACAACTTCGACGTGGCCCG

CGGCGTGCCTCTCGACTCCGGCCGGTACGAGTGGACCCCGGCGGTGAGCAGCAACTAG

SEQ ID NO: 45

>wheat KRP1B protein

M G K Y M R K C R A E D G V G G V E V T Q A V G V R T R S R A A A A

N V V V S K R R R P L P P S S P L G G A A A R A Q S G S C Y L K L R

S R M L F M A P P A P A S A A G P G H R P A P P L P A G L S R C S S

-continued

T A S S V D A S A A G Q D R S L P S C G S D A A A N S K A G A P E G

S A S N N A E S G G N R E R R E T T P S S H F P G D L S D L E S D L

A G Q N S G R S S L P Q T P T A Q V Q P A A R S R I P P A A E I E E

F F A A A E E A E A R R F A C K Y N F D V A R G V P L D S G R Y E W

T P A V S S N

SEQ ID NO: 46

>wheat KRP1D genomic

ATCCAAAGGGCGAGCCGAACAACCCAGCGGCATCATATCCCTCCCACCGGCGCCGCGCTGCGCACTGC

AGACGGAAACGGCCAAAGGAGAGCGGCGTGGGGCGGAGCGGGGGGCGATGGGGAAGTACATGCGCAAG

TGCAGGGCGGAGGACGTCGCGGTGGGCGGCGTGGAGGTCACGCAGGCCGTCGGCGTCCGGACGCGGTC

CCGGGCGGCCGCGGCCAACGTCGTCGTCTCCAAGAGGAGGCGCCCGCTGCCGCCCGCCTCGCCGTCGG

CCTCGTCGGCCCTCGCTCGCGCCCAGGGCGGGAGCTGCTACCTGAAGCTGCGGAGCCGCATGCTGTTC

ATGGCCCCGCCGGCGCCTGCGTCGGCGTCGGCCGCTGCCGCCGGGCACGGGGCGCCGCCGCCGCTCCC

GGCCGGCCTCTCGCGCTGCTCCAGCACGGCCTCGTCCGTGGACGCGTCGGCCGCGGCGCAGGACAGGA

GCCTGCCGTCGTGCGGCTCCGACGCCGCTGCCAACAAGGTGAGGGAATTGGGTCCAAACCCTAGAATT

CGGATACAATTCGAGATCTCCTTTTTGCTGAAAACCGTGGCTTTCTCCGCCCTACAGGCAGGCGCTCC

GGAGGGCTCGGCGAGCAACAACGCGGAGAGCGGCGGCAACCGCGAGAGGTGCGAGATCGAATTCCCTC

CTGTCTCCGGCCAATTCTTCCGAATTATGCATCCTAACCCCGTCCCGCTCGCTGCTTTTCAAAATTCA

GGCGAGAGACGACGCCGTCCAGCCATTTCCCCGGCGACCTGAGCGACCTGGAGTCGGATCTGGCGGGC

AAGAACAGCGGCCGGTCGTCGCTGCCGCAAACGCTGGCCGCCCAGGCTCAGCCCGCCGCGAGGTCGAG

GGTCCCGCCGGCGGCCGAGATCGAGGAGTTCTTCGCGGCCGCCGAGGAGGCCGAGGCCAGGCGCTTCG

CTTGCAAGTAAGTACTCCTACTTTAGCAGCAGCGGAAATTTCCTTATCTTGCGGCCGCCGTCGCCGTC

GCCGGAATTCTAACGTGGGAGCTCTCTACGCCAGGTACAACTTCGACGTGGCCCGCGGCGTGCCCCGC

GACTCCGGCCGGTACGAGTGGACCCCGGCGGTGAGCAGCAGCTAGGCAGGCGACGAAAGCGGGCGTGC

AAAGGGGGGAGAGAAGCCGTAGCTAGAAAGTTACTCACTGTAGAGCTGGGGCGCCGGCCGGCCGGCCG

GCCGTGTAGAAAGGCGAAGGGAAAAAGATGCTCCGGAAAGAAGCATTATAGCCTAACCAACCAACCTA

CCACCGATCATC

SEQ ID NO: 47

>wheat KRP1D coding

ATGGGGAAGTACATGCGCAAGTGCAGGGCGGAGGACGTCGCGGTGGGCGGCGTGGAGGTCACGCAGGC

CGTCGGCGTCCGGACGCGGTCCCGGGCGGCCGCGGCCAACGTCGTCGTCTCCAAGAGGAGGCGCCCGC

TGCCGCCCGCCTCGCCGTCGGCCTCGTCGGCCCTCGCTCGCGCCCAGGGCGGGAGCTGCTACCTGAAG

CTGCGGAGCCGCATGCTGTTCATGGCCCCGCCGGCGCCTGCGTCGGCGTCGGCCGCTGCCGCCGGGCA

CGGGGCGCCGCCGCCGCTCCCGGCCGGCCTCTCGCGCTGCTCCAGCACGGCCTCGTCCGTGGACGCGT

CGGCCGCGGCGCAGGACAGGAGCCTGCCGTCGTGCGGCTCCGACGCCGCTGCCAACAAGGCAGGCGCT

CCGGAGGGCTCGGCGAGCAACAACGCGGAGAGCGGCGGCAACCGCGAGAGGCGAGAGACGACGCCGTC

CAGCCATTTCCCCGGCGACCTGAGCGACCTGGAGTCGGATCTGGCGGGCAAGAACAGCGGCCGGTCGT

CGCTGCCGCAAACGCTGGCCGCCCAGGCTCAGCCCGCCGCGAGGTCGAGGGTCCCGCCGGCGGCCGAG

ATCGAGGAGTTCTTCGCGGCCGCCGAGGAGGCCGAGGCCAGGCGCTTCGCTTGCAAGTACAACTTCGA

CGTGGCCCGCGGCGTGCCCCTCGACTCCGGCCGGTACGAGTGGACCCCGGCGGTGAGCAGCAGCTAG

-continued

SEQ ID NO: 48

>wheat KRP1D protein

M G K Y M R K C R A E D V A V G G V E V T Q A V G V R T R S R A A A

A N V V V S K R R R P L P P A S P S A S S A L A R A Q G G S C Y L K

L R S R M L F M A P P A P A S A S A A A A G H G A P P P L P A G L S

R C S S T A S S V D A S A A A Q D R S L P S C G S D A A A N K A G A

P E G S A S N N A E S G G N R E R R E T T P S S H F P G D L S D L E

S D L A G K N S G R S S L P Q T L A A Q A Q P A A R S R V P P A A E

I E E F F A A A E E A E A R R F A C K Y N F D V A R G V P L D S G R

Y E W T P A V S S S

SEQ ID NO: 49

>wheat KRP2A full genomic

TTCGTCCGTTCGCGGATGGGGAAGTACATGCGGAAGTGCCGGGCCGCGCCGCGCCGCGGGCGGCGGCA

AGGCGGCGCCGCCGTCGTGGAGCACCGCGCGCCGGTGGCCCTCGGCGTCCGCACGCGGTCCCGCGCGG

CCGCCCTCAACGCGAAGATGAGGAAGCAGCAGCAGGCGACGACGTCCACGGCGGCGCGCGCGGTGGAG

GATGCGTTGCTGGGCCGTGACGGCGGCGACGCGGCCGCCGGGTGCTACCTGCATCTCCGGAGCAGGAG

GCTGTTCATGCCTGCTTCCGCGGCGGTGGATCAGCTCCGGGGACTTGGGGCGGACGAGGAGGCTTCGA

CGGCGGGGCTGCCGGATTCTCGGCCCTCGGTGGAGGCGGCGGTCGTGGCCGGGGTCTCGCGCTGCTCC

AGCACCGCGTCGACGGCGGTGGACGTGGCGGCTAGAGAGAGGAGCGGCGACGAAGCGGAGGTGAGTGG

GCCACTCACTGCCCTAGAATTCTCCGTAAATTCGGCCGGTCGATCGGCAGTTTCTGCTGCTGAATTAC

GAGATTTGGTTCTGACTGTCTTGGTCGATCAGCAGGCGTGCGAGAGTGGCGACGTGGAGAGCTCCGTC

AGCGACTCTGAGTGCGGCGGCCGGGACAGGTGAGTCCTCCTCTCTCGATACCGACAGGAATTCTGCTG

AATTATCCATTGTTTTCTATTCTCCAGGGTGATCTTGAGTTCTTGACCCGGTTTTGCTTCTGAATTTG

ACCTGTTTGAATTGTGGTAATCCAGGAGGGAGACCACGCCGTCGAGCCATTCCCCGGCAGATTTGAGC

GACCTGGAGTCGAGCCAGTCGGCGGACGAGCAGAAGCACAAACGCAGGAGGTATCCGGCAACAACGAC

GACGACCGCAGCGCCATTCCGCTTAGACTTGGAGGCGAGAGCAAGGATGCCACCGGCGGCAGAGATCG

ACGAGTTCTTCGCCGCCGCGGAGAAGGCCCAGGCCGAGCGCTTCGCCGCCAAGTAAGTGGAAATTACA

ATTGAGCACACAAGTACACATACGTCTTGGCACTTGGCAGTCGCTCTATCGCCGTCACAGACGCCGCC

ACGNCTAAGCCTTGTGCTCTCGCTGCCTCACTGCAGGTACAACTTCGACGTCGCGCGCGGCGTGCCTC

TCAACGCCGGCCGGTTCGAGTGGACCCCGGTGGCCACCGTCTGAGGCTCTGAGCATGATGCAAAATGA

CGGGAAGCTAGCGGCGGCGCGCGTAGAAAGGGAAGGCCTGCTGGGAGTGAAAAGAGACGCTGATCCAA

CCCGCAAAGGAAAACAGTAAAGAGAAAGAGGAGTGAAAAAAGAACAGAATAATCCCATGCACAGCAGC

CTAGAGCTAGA

SEQ ID NO: 50

>wheat KRP2A coding

ATGGGGAAGTACATGCGGAAGTGCCGGGCCGCGCCGCGCCGCGGGCGGCGGCAAGGCGGCGCCGCCGT

CGTGGAGCACCGCGCGCCGGTGGCCCTCGGCGTCCGCACGCGGTCCCGCGCGGCCGCCCTCAACGCGA

AGATGAGGAAGCAGCAGCAGGCGACGACGTCCACGGCGGCGCGCGCGGTGGAGGATGCGTTGCTGGGC

CGTGACGGCGGCGACGCGGCCGCCGGGTGCTACCTGCATCTCCGGAGCAGGAGGCTGTTCATGCCTGC

TTCCGCGGCGGTGGATCAGCTCCGGGGACTTGGGGCGGACGAGGAGGCTTCGACGGCGGGGCTGCCGG

ATTCTCGGCCCTCGGTGGAGGCGGCGGTCGTGGCCGGGGTCTCGCGCTGCTCCAGCACCGCGTCGACG

-continued

GCGGTGGACGTGGCGGCTAGAGAGAGGAGCGGCGACGAAGCGGAGGCGTGCGAGAGTGGCGACGTGGA

GAGCTCCGTCAGCGACTCTGAGTGCGGCGGCCGGGACAGGAGGGAGACCACGCCGTCGAGCCATTCCC

CGGCAGATTTGAGCGACCTGGAGTCGAGCCAGTCGGCGGACGAGCAGAAGCACAAACGCAGGAGGTAT

CCGGCAACAACGACGACGACCGCAGCGCCATTCCGCTTAGACTTGGAGGCGAGAGCAAGGATGCCACC

GGCGGCAGAGATCGACGAGTTCTTCGCCGCCGCGGAGAAGGCCCAGGCCGAGCGCTTCGCCGCCAAGT

ACAACTTCGACGTCGCGCGCGGCGTGCCTCTCAACGCCGGCCGGTTCGAGTGGACCCCGGTGGCCACC

GTCTGA

SEQ ID NO: 51

>Wheat KRP2A protein
MGKYMRKCRAAPRRGRRQGGAAVVEHRAPVALGVRTRSRAAALNAKMRKQQQATTSTAARAVEDALLG

RDGGDAAAGCYLHLRSRRLFMPASAAVDQLRGLGADEEASTAGLPDSRPSVEAAVVAGVSRCSSTAST

AVDVAARERSGDEAEACESGDVESSVSDSECGGRDRRETTPSSHSPADLSDLESSQSADEOKHKRRRY

PATTTTTAAPFRLDLEARARMPPAAEIDEFFAAAEKAQAERFAAKYNFDVARGVPLNAGRFEWTPVAT

V*

SEQ ID NO: 52

>wheat KRP2B genomic
TTTCGTCCGTTCGCGGATGGGGAAGTACATGCGGAAGTGCAGGGGCGCGGCCGCGGGCGGCGGCAGGG

CGGCGCCGGCCGTCGTGGAGCACCGCGCGCCGGTGGCCCTCGGCGTCCGCACGCGGTCCCGCGCGGCC

GCCTTCGACGCTAAGAGGAGGAAGCAGCAGGCGACGACGTCCACGGCAGCGCGCGCGGTGGACGATGG

GTTGCTGGGCCGTGACGGCGGCGACGCGGCCGGCGGGTGCTACCTGCATCTCCGGAGCAGGAGGCTGT

TCATGCCTGCTTCCGCGGTGGTGGATCGGCTCCGGGGACAGGGGGCGGACGAGGAGGCTTCGACGGCG

AGGCTGGCGGATTCCGGGCCTTCCGTGGAGGCGGGGGTCGTCGCCGGGGTCTCGCGCTGCTCGAGCAC

CGCGTCCACGGCAGCAGACGTGGCGGCTAGAGAGAGGAGCGGCGACGAAGCAGAGGTGAGTGGTCCAC

TGCCCTAGAATTCTCCGCTACTTCGAGCTGTCGATCGGGCCATTTCTGCTGCTGAATTAGGAGGTTTG

GTTCCTATGTCTTGTCCTGCAGGCGTGCGAGAGTCGCGACGTGGAGAGCTCCGTCAGCGACTCTGAGT

GCGGCGGCCGGGACAGGTGAGTCCTCCTCTCTCGATATATACCGACGGGAATTCTGCTGAATTATCCA

TTGTTTTCTACTCCACAAGGTGATCTTGAGTTGAGGGGCCTGGCTTTGCTTCTGAATTTGACCTGTTG

GATTGTACTAATCCAGGAGGGAGGCGACGCCGTCGAGCCGTTCGCCGGTAGATTTGAGCGACCTGGAG

TCGAGCCAGGCGCCGGACGAGCAGAAGCACAAACGCAGGAGGTGTCCGGCAGCAACGACGGCGGCAGC

AGCGCCATTCCACTTAGACTCGGAGGCGAGAGCAAGGATGCCACCCGCGGCAGAGATCGACGAGTTCT

TCGCCGCCGCCGAGAAGGCCCAGGCCGAGCACTTCGCGGCCAAGTAAGTGGAAATTTACAATCGAGCG

CATCCGCACGCACGTACATACTCCCGTCTTGGCAGTCGCTCCATCGTCGTCACAGACGTCCCCGTGCC

TAGCTAAGCATTGTGCTGCCGCTGCCTCATTGCAGGTACAACTTCGACGTCGCGCGCGGCGTGCCTCT

CAACGCCGGCCGGTTCGAGTGGACCCCGGTGGCCACCGTCTGAGGCTCTGATGCAATTGGCGGGGAGC

GTAGCGGCGGCTCGCGTAGAAAGGGAAGGCCTGCTGGGAGTGAAAAGAGACGCTGATCCAACCCCCAA

AGGAAAACAGTAAAGAGAAAGAGGAGTGAAAAAGAACAGAATAATCCCATGCACAGCAGGCCTAGAGC

TAGA

SEQ ID NO: 53

>wheat KRP2B coding
ATGGGGAAGTACATGCGGAAGTGCAGGGGCGCGGCCGCGGGCGGCGGCAGGGCGGCGCCGGCCGTCGT

GGAGCACCGCGCGCCGGTGGCCCTCGGCGTCCGCACGCGGTCCCGCGCGGCCGCCTTCGACGCTAAGA

-continued

GGAGGAAGCAGCAGGCGACGACGTCCACGGCAGCGCGCGCGGTGGACGATGCGTTGCTGGGCCGTGAC

GGCGGCGACGCGGCCGGCGGGTGCTACCTGCATCTCCGGAGCAGGAGGCTGTTCATGCCTGCTTCCGC

GGTGGTGGATCGGCTCCGGGGACAGGGGGCGGACGAGGAGGCTTCGACGGCGAGGCTGGCGGATTCCG

GGCCTTCCGTGGAGGCGGGGGTCGTCGCCGGGGTCTCGCGCTGCTCGAGCACCGCGTCCACGGCAGCA

GACGTGGCGGCTAGAGAGAGGAGCGGCGACGAAGCAGAGGCGTGCGAGAGTCGCGACGTGGAGAGCTC

CGTCAGCGACTCTGAGTGCGGCGGCCGGGACAGGAGGGAGGCGACGCCGTCGAGCCGTTCGCCGGTAG

ATTTGAGCGACCTGGAGTCGAGCCAGGCGGCGGACGAGCAGAAGCACAAACGCAGGAGGTGTCCGGCA

GCAACGACGGCGGCAGCAGCGCCATTCCACTTAGACTCGGAGGCGAGAGCAAGGATGCCACCCGCGGC

AGAGATCGACGAGTTCTTCGCCGCCGCCGAGAAGGCCCAGGCCGAGCACTTCGCGGCCAAGTACAACT

TCGACGTCGCGCGCGGCGTGCCTCTCAACGCCGGCCGGTTCGAGTGGACCCCGGTGGCCACCGTCTGA

SEQ ID NO: 54

>wheat KRP2B protein

MGKYMRKCRGAAAGGGRAAPAVVEHRAPVALGVRTRSRAAAFDAKRRKQQATTSTAARAVDDALLGRD

GGDAAGGCYLHLRSRRLFMPASAVVDRLRGQGADEEASTARLADSGPSVEAGVVAGVSRCSSTASTAA

DVAARERSGDEAEACESRDVESSVSDSECGGRDRREATPSSRSPVDLSDLESSQAADEQKHKRRRCPA

ATTAAAAPFHLDSEARARMPPAAEIDEFFAAAEKAQAEHFAAKYNFDVARGVPLNAGRFEWTPVATV*

SEQ ID NO: 55 wheat KRP2D genomic

GTTCTTTCTTTTCGTCCGTTCGCGGATGGGGAAGTACATGCGGAAGTGCAGGGCCGCGGCCGCGGGCG

GCGGCAGGGCGGCGCCGGCCGTCGTGGAGCACCGCGCGCCGGTGGCCCTCGGCGTCCGCACGCGGTCG

CGCGCGGCCGCCCTCGACGCGAAGATGAGGAAGCAGCAGCAGGCGACGACGTCCACGGCGGCGCGCGG

GGTGGAGGATGCGTTGCTGGGCCGTGACGGCGGCGACGCGGCCGCCGGGTGCTACCTGCATCTCCGGA

GCAGGAGGCTGTTCATGCCTGCTGCCGCGGTGGTGGATCAGCTGCGGGGACAGGGGGTGTGTGAGGAG

GCTTCCACAGCGGGGCTGCCGGACTCTGGGCCCTCGGTGGAGGCGGCGGTCGGGGCCGGGGTCTCGCG

CTGCTCCAGCACCGCGTCCACGGCGGTCGACGTGGCGGCTAGAGAGAGGAGCGGGGATGAAGCGGAGG

TGAGTGGTCCACTGCCCTAGAATTCTCCGCTAATTCGAGCTATCGATCGGGCCGTTTCTGCTGCTGAA

TTACGAGATTTGGTTCTGACTGTCTTGGTCGATCAGCAGGCGTGCGAGAGTCGCGACGTGGAGAGCTC

CGTCAGCGACTCTGAGTGCGGCGGCCGGGACAGGTGAGTCCTCCTCTCTCGATACCGACGGGAATTCT

GCTGAATTACCCATTGTTTTCTACTCTCCAGGGTGATCTTGAGTTGAGGGACCTGGTTTTGCTTCTGA

ATTTGACCTGTTGGATTGTGGCAATCCAGGAGGGAGACGACGCCGTCGAGCCGTTCGCCGGTAGATTT

GAGCGACCTGGAGTCGAGCCAGGCGGCGGACGAGCAGAAGCACAAACGCAGGAGGTGTCCGGCAACAA

CGACGACGACCGCAGCGCCATTGCACTATGACTTGGAGGCGAGAGCAAGAGCAAGGATGCCACCAGCG

GCAGAGATCGACGAGTTCTTCGCCGCCGCGGAGAAGGCCCAGGCCGAGCGCTTCGCCGCCAAGTAAGT

GGAAATTTACAATTGAGCAAATCCGCACGCACGTCTTGGCAGTCGCTCGATCGTCCTCACAGACGCCG

CCGCGCCTAAGCATTGTGCTACCGCTGCCTCATTGCAGGTACAACTTCGACGTCGCGCGCGGCGTGCC

TCTCAACGCCGGCCGGTTCGAGTGGACCCCGGTGGCCACCGTGTGAGCAGAGCATGATGCAAATGACG

GGGAGCTAGCGGCGGCGCGCGTAGAAAGGGAAGGCCTGCTGGGAGTGAAAAGAGACGCTGATCCAACC

CCCCAAAGGAAAACAGTAAAGAGAAAGAGGAGTAAAAAAGAACAGAATAATCCCATGCACAGCTGCCT

AGAGCTAGGCATGCAGTAGCCCTCTCCC

-continued

SEQ ID NO: 56
>wheat KRP2D coding
ATGGGGAAGTACATGCGGAAGTGCAGGGCCGCGGCCGCGGGCGGCGGCAGGGCGGCGCCGGCCGTCGT

GGAGCACCGCGCGCCGGTGGCCCTCGGCGTCCGCACGCGGTCCCGCGCGGCCGCCCTCGACGCGAAGA

TGAGGAAGCAGCAGCAGGCGACGACGTCCACGGCGGCGCGCGCGGTGGAGGATGCGTTGCTGGGCCGT

GACGGCGGCGACGCGGCCGCCGGGTGCTACCTGCATCTCCGGAGCAGGAGGCTGTTCATGCCTGCTGC

CGCGGTGGTGGATCAGCTGCGGGGACAGGGGGTGTGTGAGGAGGCTTCCACAGCGGGGCTGCCGGACT

CTGGGCCCTCGGTGGAGGCGGCGGTCGGGGCCGGGGTCTCGCGCTGCTCCAGCACCGCGTCCACGGCG

GTCGACGTGGCGGCTAGAGAGAGGAGCGGGGATGAAGCGGAGGCGTGCGAGAGTCGCGACGTGGAGAG

CTCCGTCAGCGACTCTGAGTGCGGCGGCCGGGACAGGAGGGAGACGACGCCGTCGAGCCGTTCGCCGG

TAGATTTGAGCGACCTGGAGTCGAGCCAGGCGGCGGACGAGCAGAAGCACAAACGCAGGAGGTGTCCG

GCAACAACGACGACGACCGCAGCGCCATTGCACTATGACTTGGAGGCGAGAGCAAGAGCAAGGATGCC

ACCAGCGGCAGAGATCGACGAGTTCTTCGCCGCCGCGGAGAAGGCCCAGGCCGAGCGCTTCGCCGCCA

AGTACAACTTCGACGTCGCGCGCGGCGTGCCTCTCAACGCCGGCCGGTTCGAGTGGACCCCGGTGGCC

ACCGTGTGA

SEQ ID NO: 57
>wheat KRP2D protein
MGKYMRKCRAAAAGGGRAAPAVVEHRAPVALGVRTRSRAAALDAKMRKQQQATTSTAARAVEDALLGR

DGGDAAAGCYLHLRSRRLFMPAAAVVDQLRGQGVCEEASTAGLPDSGPSVEAAVGAGVSRCSSTASTA

VDVAARERSGDEAEACESRDVESSVSDSECGGRDRRETTPSSRSPVDLSDLESSQAADEQKHKRRRCP

ATTTTTAAPLHYDLEARARARMPPAAEIDEFFAAAEKAQAERFAAKYNFDVARGVPLNAGRFEWTPVA

TV*

Note for KRP4 genomic sequences: Intron 1 is approximately 2500 bp and therefore, the intron1 sequence was not retrieved in full. Intron2 is 194 by in KRP4 A and B genomes and 192 by in KRP4 D genome and were retrieved in full.

SEQ ID NO: 58
>wheat KRP4A partial genomic exon1
CTCGCTTAAATCCGCCAAAGCGCACCCAGCGGGGCCCCAAACCCTAGCCCGGGCCGCGCCGCGCATGG

GCAAGTACATGCGCAAGCCCAAGGTCTCCGGCGAGGTGGCCGTCATGGAGGTCGCCGCCGCGCCGCTG

GGGGTCCGCACCCGCGCGCGGGCGCTCGCGATGCAGAGGCAGCCGCAGGGGGCGCCGGGGGCCAAGGA

CCAGGGGGAGTACCTGGAGCTCAGGAGCCGGAAGCTCGAGAAGCTGCCCCCCGCCGCCGCCGCCGGCGA

GGAGGAGGGCGGCCGCGGCGGAGCGTGTCGAGGCCGAGGCCGAGGCCGACAAGGTGTCCTTCGGGGAG

AACGTGCTCGAGCCGGAGGCCATGGGGAGGTGAGCCTTCTCCTGCGCCCGCGATTTTCTTCGGTTCAT

GGGGTTTTATTTCTCGGCGGGGGGATTATAACCGTGCCAGGGTTTAGGGTTTTGTGTCGTACCGAGAA

GCTTTGGATTGCTTCTTCTGTTTCGCGCTTCGGCTCGTTCCATTTTTTCCTTGTCAATTTGGCTTGTTC

TATCCGTGCTGCGTGCGGGGCTCGAATTTGGTGTCGATGCTATTTTCCCCAATATCTTTCTTATTAAG

CTTTGCTGTTTATTGGGGATTTTTTCTGTCCCAACTCTTC

SEQ ID NO: 59
>Wheat KRP4A partial genomic exons2-3
AGGCAAATTCGGTAGAAATGTGTAGCCAATTGTGGCATTGCTAGGCCTAGTTAGAACCAAACAACCCC

GGATACTCATAAGGGGGGGATTCCTTATTTTTTTATGACCACGGATGATATCGATATGTTTTCTTCTT

TTTGCATACCCTGTTAAGTTACAGGTGATTTTTTTCCCTTTTGCTACGCGTCCTCGCTATGGTTGTTTC

TAAAAATTGAGTGTGTATGTATGTTTTGTGGCTAGCAGGGGTACCAGGGAGACGACGCCCTGCAGCTT

-continued

GATTAGGGACTCGGGAATGATAAGCACTCCTGGATCCACAACAAGACCGAGCCACTCGAATTCCCATC

GCAGGGTGCAAGCTCCAGCGCGCCATATTATTCCAAGTTCAGCAGAGATGAATGAGTTCTTCTCTGCT

GCAGAGCAACCGCAACAGCAAGCCTTCATCGACAAGTACGACATTGTTTGGTTCTCTCAGTCAGTTAA

CCTTGTCTAATTAAAAAAAATCTTTCAATATCTTTGCAGTGAAGAATGCCAACTCAGCGTGCAATGTG
GTTTTGACACGTGATATGTTCATGCCTTTGCTCTTGATAAAAAGTGTGATTATAACACTAACAACATG

GTTTCATGGCTTAATAATCTTCAGGTACAACTTTGATCCTGTGAACGACTGTCCTCTCCCAGGCCGAT

ACGAGTGGGTGAAGCTAGACTGATAATTCTCCAGGAAGGAGAGCACCATGTATCTCTCTGCTCCCTCC

ACCTTAGCGTCGTGGTAGAGGCGCGCACCGTCGTGTTAGCTTTGTTTCCGTTGTAAAAAGAATTAGGG

TTAGCCTGTAGTAGCCTCAATGGTTGTGTAACATACAGAAGTAATGCTGAGTTACACCCTATCCCTCA

AACTCCCCAAATGTCGGTAGC

SEQ ID NO: 60

>wheat KRP4A coding
ATGGGCAAGTACATGCGCAAGCCCAAGGTCTCCGGCGAGGTGGCCGTCATGGAGGTCGCCGCCGCGCC

GCTGGGGGTCCGCACCCGCGCGCGGGCGCTCGCGATGCAGAGGCAGCCGCAGGGGGCGCCGGGGGCCA

AGGACCAGGGGGAGTACCTGGAGCTCAGGAGCCGGAAGCTCGAGAAGCTGCCCCCGCCGCCGCCGCCG

GCGAGGAGGAGGGCGGCCGCGGCGGAGCGTGTCGAGGCCGAGGCCGAGGCCGACAAGGTGTCCTTCGG

GGAGAACGTGCTCGAGCCGGAGGCCATGGGGAGGGGTACCAGGGAGACGACGCCCTGCAGCTTGATTA

GGGACTCGGGAATGATAAGCACTCCTGGATCCACAACAAGACCGAGCCACTCGAATTCCCATCGCAGG

GTGCAAGCTCCAGCGCGCCATATTATTCCAAGTTCAGCAGAGATGAATGAGTTCTTCTCTGCTGCAGA

GCAACCGCAACAGCAAGCCTTCATCGACAAGTACAACTTTGATCCTGTGAACGACTGTCCTCTCCCAG

GCCGATACGAGTGGGTGAAGCTAGACTGA

SEQ ID NO: 61

>wheat KRP4A protein
Mgkymrkpkvsgevavmevaaaplgvrtraralamqrqpqgapgakdqgeylelrsrkleklpppppp arrraaaaerveaeaeadkvsfgenvlepeamgrgtrettpcslirdsgmistpgsttrpshsnshrr vqaparhiipssaemneffsaaeqpqqqafidkynfdpvndcplpgryewvkld*

SEQ ID NO: 62

>wheat KRP4B partial genomic exon1
CTCGCTTAAATCCGCAAGGCGCACCCAGGGGGGCCCAAACCCTAGCCCGGGCCGCGCCGCGCATGGGC

AAGTACATGCGCAAGCCCAAGGTCTCCGGCGAGGTGGCCGTCATGGAGGTCGCCGCCGCGCCGCTAGG

GGTCCGCACCCGCGCACGAGCGCTCGCGATGCAGAGGCAGCCGCAGGGGGCGGCGGTGGCCAAGGACC

AGGGGGAGTACCTGGAGCTCAGGAGTCGGAAGCTCGAGAAGCTGCCCCCGCCGCCGCCGCCGGCGAGG

AGGAGGGCGGCCGCGGCGGAGCGTGTCGAGGCCGAGGCCGAGGCCGACGAGGTGTCCTTCGGTGAGAA

CGTGCTCGAGTCGGAGGCCATGGGGAGGTGAGCCTTCTCCTGCGCCGGCGATTTTCTTCGGTTATTGG

GGTTTTATTTCTCGGCGGGGGGATTAiTACCGTGCTAGGGTTTAG6GTTTTGTGTCGTACCGAGAAGC

TTTGGATTGCTTCTTCTATTTCGCGCTTCGGCTCGTTTCATTTCTCCTTGTCAATTTGGCTTGTTCTA

TCCGTGCTGCGTGCGGGGCTCGAATTTGGTGTGGATGCTATTTTCCCCAATATCTTTGTTACTATTAA

ACTTTGCTGTTTATTGGGGATTTTTCCGTCTAACTCTTC

SEQ ID NO: 63

>wheat KRP4B partial genomic exons2-3
TTGGGGGGGGTTACTAGCCCCACCATTCTTTTGTTTCCCATGGGCCTTGTGTTTCGGTTGTGTGCTAG

CCTTTATATGGCATATGAGATAGATTGAAGGGCTGTTTAGTTAGGCAACTTGTGGCCCCAATCTGTTT

GAACTAACCTTAGGCAAGTTTGGTAAGAAATGTGTGGCAAATTGTGGCATTGCTAGGCCTAGTTAGAA

-continued

CCAAACAACCCCGGATACTCATAAGGGGGGGATTCCTTATTTTTTATGACTATTGATATGTGTTCTTC

TTTTTCCATACCCTGTTAAGTTACAGGTGATTTTTTCCCTTTTGCTATGCTTCCTCTCTATGGTTGTT

TCTAAAAATTGAGTGTGTATGTATGTTTTGTGGCTAGCAGGGGTACCAGGGAGACGACGCCCTGCAGC

TTGATTAGGGACTCGGGAACGATAAGCACTCCTGGATCCACAACAAGACCGAGCCACTCGAATTCCCA

TCGCAGGGTGCAAGCTCCAGCGCGCCATATTATTCCATGTTCAGCAGAGATGAATGAGTTCTTCTCTG

CTGCGGAGCAACCGCAACAGCAAGCCTTCATCGACAAGTACGGCATTGTTTGGTTCTCTCAGTCAGTT

AACCTTGTCTAATTTAAAAAAAGGGAAATCTTTCAATATCTTCGCAGTGAAGAATGCCAACTCAGCGT

GCAATGTGGTTTTGACACGTGATATGTTTACGCCTTTGCTCTTGATAAAAAGTGTGATTATAACACTA

ACAACATGGTTTCATGGCTTAATAATCTTCAGGTACAACTTTGATCCTGTGAACGACTGTCCTCTCCC

AGGCCGATACGAGTGGGTGAAGCTAGACTGATAATTCTCCAGGAAGGAGAGCATCATGTACTTCTCCG

CTCCCTCCACCTTAGCGTCGTGGTAAAGGCGCGCCCCGTCGTGTTAGCTTTGTTTCCGTTGTAAAAAG

AATTAGGTTAGCCTGTAGTAGCCTCAATGGTCGTGTAACATACAGAAGTAATGCTGAGTTACACCCTA

ATCCCTCAAACTCCAATGTAACGGTTAGCAGCTCATTCTGAAATGACCACA

SEQ ID NO: 64

>wheat KRP4B coding

ATGGGCAAGTACATGCGCAAGCCCAAGGTCTCCGGCGAGGTGGCCGTCATGGAGGTCGCCGCCGCGCC

GCTAGGGGTCCGCACCCGCGCACGAGCGCTCGCGATGCAGAGGCAGCCGCAGGGGGCGGCGGTGGCCA

AGGACCAGGGGGAGTACCTGGAGCTCAGGAGTCGGAAGCTCGAGAAGCTGCCCCCGCCGCCGCCGCCG

GCGAGGAGGAGGGCGGCCGCGGCGGAGCGTGTCGAGGCCGAGGCCGAGGCCGACGAGGTGTCCTTCGG

TGAGAACGTGCTCGAGTCGGAGGCCATGGGGAGGGGTACCAGGGAGACGACGCCCTGCAGCTTGATTA

GGGACTCGGGAACGATAAGCACTCCTGGATCCACAACAAGACCGAGCCACTCGAATTCCCATCGCAGG

GTGCAAGCTCCAGCGCGCCATATTATTCCATGTTCAGCAGAGATGAATGAGTTCTTCTCTGCTGCGGA

GCAACCGCAACAGCAAGCCTTCATCGACAAGTACAACTTTGATCCTGTGAACGACTGTCCTCTCCCAG

GCCGATACGAGTGGGTGAAGCTAGACTGA

SEQ ID NO: 65

>wheat KRP4B protein mgkymrkpkvsgevavmevaaaplgvrtraralamqrqpqgaavakdqgeylelrsrkleklppppa arrraaaaerveaeaeadevsfgenvleseamgrgtrettpcslirdsgtistpgsttrpshsnshrr vqaparhiipcsaemneffsaaeqpqqqafidkynfdpvndcplpgryewvkld*

SEQ ID NO: 66

>wheat KRP4D partial genomic exon1

CTCGCTTAAATCCGCAAGGCGCACCCAGGGGGGCCCAAACCCTAGCCCGGGCCGCCCCGCGCATGGGC

AAGTACATGCGCAAGCCCAAGGTCTCCGGCGAGGTGGCCGTCATGGAGGTCGCCGCCGCGCCGCTGGG

TGTCCGCACCCGCGCGCGAGCGCTCGCGATGCAGAGGCAGCCGCAGGGGGCGCCGGGGGCCAAGGACC

AGGGGGAGTACCTGGAGCTCAGGAGCCGGAAGCTCGAGAAGCTGCCCCTGCCGCCGCCGCCGGCGAGG

AGGAGGGCGGCCGCGGCGGAGCGTGTCGAGGCCGAGGCCGAGGCCGACGAGGTGTCCTTCGGGGAGAA

CGTGCTCGAGTCGGAGGCCATGGGGAGGTGAGCCGCCTTCTCCTGCGCCGGCGATTTTCTTCGGTTCT

GGGGTTTTATTTCTCGGCGGGGGGATTATTACCGTGCTAGGGTTTAGGGTTTTGTGTCGTACCGAGAA

GCTTTGGATTGCTTGTTCCATTTCACGCTTCGGCTCGTTTCTTTTTTCCTTGTCAGTTTGGCTTGTTC

TGTCCGTGCTGCGTGCGGGGCTCGAATTTGGTGTGGATGCTATTTTCCCCAATATCTTTGTTAAGCTT

GGCTGTTTTATTGGGGATTTTTTTCCTGGCTAACTCTTC

-continued

SEQ ID NO: 67
>wheat KRP4D partial genomic exons2-3
GGGGGGGGTTAACTAGCCCACCATTTTTTTGTTTCCCATGGGCCTTGTGTTTTGGTTGTGTGCTAGCC

TTTATATGGCATATGAGATAGATTGAAGGGCTGTTTGGTTAGGCAACTTGTGGCTCCAATTTGTTTGA

ACTAACCTTAGGCAAGTTTGGTGAGAAATGTGTGGCAAATTGTGGCATTGCTAGGCCTAGTTAGAACC

AAACAACCCCGGATACTCATAAGGGGGGGATTCCTTATTTCTTACGACCACGGATGATATCGATATGT

GTTCTTCTTTTTGCATACCCTGTTAAGTTACAGGTGATTTTTCCCCTTTTGCTATACTTCCTCTCTAT

GGTTGTTTCTAAAAATTGAGTGTGTATGTATGTTTTGTGGCTAGCAGGGGTACCAGGGAGACGACGCC

CTGCAGCTTGATTAGGGACTCGGGAACGATAAGCACTCCTGGATCCACAACAAGACCAAGCCACTCGA

ATTCCCATCGCAGGGTGCAAGCTCCAGCGCGCCATATTATTCCATGTTCAGCAGAGATGAATGAGTTC

TTCTCTGCTGCGGAGCAACCGCAACAGCAAGCCTTCATCGACAAGTACGGCATTGTTTGGTTCTCTCA

GTCAGTTAACCTTGTCTAATTAAAAAAATCTTTCAATATCTTCGCAGTGAAGAATGCCAACTCAGAGT

GCAATGTGGTTTTGACACGTGATATGTTCACGCCTTTGCTCTTGATAAAAAGTGTGATTATAACACTA

ACAACATGGTTTCATGGCTTAATAATCTTCAGGTACAACTTTGATCCTGTGAACGACTGTCCTCTCCC

AGGCCGATACGAGTGGGTGAAGCTAGACTGATAATTCTCCAGGAAGGAGAGCACCATGTACCTCTCCG

CTCCCTCCACCTTAGCGTCGTGGTAGAGGCGCGCACCGCCGTGTTAGCTTTGTTTCCGTTGTAAAAAG

AATTAGGGTTAGCCTGTAGTAGCCTCAATGGTCTTGTAACATACAGAAGTAATGCTGAGTTACACCCT

AATCCCTCAAAACTCCAATGTAACGGTTAGCAGCTCATTCTGTAATGACCACA

SEQ ID NO: 68
>wheat KRP4D coding
ATGGGCAAGTACATGCGCAAGCCCAAGGTCTCCGGCGAGGTGGCCGTCATGGAGGTCGCCGCCGCGCC

GCTGGGTGTCCGCACCCGCGCGCGAGCGCTCGCGATGCAGAGGCAGCCGCAGGGGGCGCCGGGGGCCA

AGGACCAGGGGGAGTACCTGGAGCTCAGGAGCCGGAAGCTCGAGAAGCTGCCCCTGCCGCCGCCGCCG

GCGAGGAGGAGGGCGGCCGCGGCGGAGCGTGTCGAGGCCGAGGCCGAGGCCGACGAGGTGTCCTTCGG

GGAGAACGTGCTCGAGTCGGAGGCCATGGGGAGGGGTACCAGGGAGACGACGCCCTGCAGCTTGATTA

GGGACTCGGGAACGATAAGCACTCCTGGATCCACAACAAGACCAAGCCACTCGAATTCCCATCGCAGG

GTGCAAGCTCCAGCGCGCCATATTATTCCATGTTCAGCAGAGATGAATGAGTTCTTCTCTGCTGCGGA

GCAACCGCAACAGCAAGCCTTCATCGACAAGTACAACTTTGATCCTGTGAACGACTGTCCTCTCCCAG

GCCGATACGAGTGGGTGAAGCTAGACTGA

SEQ ID NO: 69
>wheat KRP4D protein
mgkymrkpkvsgevavmevaaaplgvrtraralamqrqpqgapgakdqgeylelrsrkleklplpppp arrraaaaerveaeaeadevsfgenvleseamgrgtrettpcslirdsgtistpgsttrpshsnshrr vqaparhiipcsaemneffsaaeqpqqqafidkynfdpvndcplpgryewvkld*

SEQ ID NO: 70
>wheat KRP5A genomic
CCGCTCTGCAGGCAGGCGCCCCGGAGGGCTCGGCGAGCAACAACGCGGAGAGCGGCGGCAACCGCGAG

AAGCCGGCGCCATGGGCAAGTACATGCGCAAGAGCAAGGCCTCGGGGGAGGTGGCCGTCATGGAGGTC

GCCGGCGCGCTGCTCGGCGTCCGCACCCGCTCCCGCACCCTCGCCGCGCAGCAGCAGCGCGCTCCGTC

CCCTTCGCCGCAGCGCAAGGGCCACGAGGACGGCGACTACCTCGAGCTCAGGAGCAGGAGGCTCGAGA

AGCAGCCGCCGCCGGGGCCCAAGGACAAGGAGGACGCGCCGCAGCCGCCGGCCGCCGGTGGGAGGAGG

ATGGAGCAGGCGCCGTCGTCGTTCGCCGCCGAGGGCTTCGAGGCCGACCTCGAGGTCTCCTTCGGCGA

-continued

CAACGTCCTGGACTGGGACGCCACCGACAGGTAACAACAGAGCACCAGACTTTTCTCTCCTCCCCTTC

CTCTTCCGCCAATCCCCCCCCTCCGCCTCAGTCAGCAATCCCCTCTCGCGCCCCGCCCCGGCCGATAC

GAATACGACTGAGGTTTAGGGTTTATCCGCCGCCGTGTCGCCGTCCTGCTCCATTAGCGCCGCCGCGT

GCTCTCAAATCTCAACTCTCAGGCGCCGGCAACCTCAAGAACCCCCTCCCTATCAGTTTTCTCAGACG

AGCGCCGCCGCTGGTCCGGCGATTTTCTTCTCCATCAGGATTGAAGCGCCCAAATAGCCACACCTTCC

GCTGATTGTGCCCGGATGCCTGCAAGAATCAAGGCCTCCGCTGGCCTTGATTTCCTCAAGCCTTAGCC

GTTGGCTGGCTGGAGCTTGAAAGAATCGAAGAAACGCCTGTCCGCTGTGTTGACCCGGGGAAAAAGGC

CCCCCTATTTCCCCCCCTCCAGAAAAGCCGCCATTTTCCCCCTCCAAACAAAGATGCATCCAGGCGCA

CTCAATCAACCCCCAATCAAAGTGGGCGCTGCACTTGATTAGTGGAGCCTCCTCCTCCTCCTCCTCCA

GTGGCCGTGGCCGTGGCCTCCGCCTTTTCCCCGTAGTGGCAGGGGAAAGTAGCCCCCTTTCCCCTTCC

CCACCACAGCCGCCCTCCATTGGCCTGGCCCCAATCTTTCCCAACAGCAACCAGAGGGAGAGAGGCCC

CTCTCCCGCCCTTTCGCCAGCAATTTCAATCCCACAAAGCCGAGCGCCACCGCCGTCGCGCTCAGGGC

CCCATTCGCCACCGCCGTGGGTGAAAATGGCAAGCTGCTCATCATTGGCCCTTGTACCGGAGCGCCAC

CGCCGCCATTGAATGCCTGCCCTTGTCTGGAGGGATATGGCTGGACCTTTCCGCTTGAATGGACACTC

TGACCGGACCACGTTTTTGTTCTAGCCAGTGCCTCCATTCATATTTACCCCTTGGCCCTTGTTGTGAG

CATTTGCACCAGCCACTTGAAGAGAAAAGATTTTACTTCTAGTAATTCAGGCCTTGGAAGACCTCGGT

AAATGTTTCCCCAGCTTCTTTAATTCCACACCTTGTTCGTAGGATTGATCTCGCGCGTGGTCCCTTGT

CCCCCGGCGTATGCATGTTGAACGTGCTCCCCCCATTTAGCAGCTTGCTTGGCCGTATTAGGCCAAGT

TGTTGCTTGCTTGTCAGCATTCAGTCATTCAGCGTGCTTGTGCTGCTGCTGCGCCAATAATCAGGCAC

ACCTCACATTGTGTGATGTGGGGCACTTGTTAGCAATGAAATGGACAAGATCATGCGGCATGCTAGAA

AATGAATGAGCTGTCGTGTTCAGCTTCCTGTAGCTTGGTCTCATCTGAGCTCACCAACCAGGCTTGAT

TCTGCAGCAGTACTACGTAATTTGCAAGGCCCTCTTGTGCATTTCTAGCTTCTGAACCTCATGTTGTG

CTGTTCGTCGGTGCTGCGTGCAGGGGCGCCAGGGAGACGACGCCGTGCAGCCTCATCTACAGCTCGGA

GACGATGAGCACCCCCGGGTCGGCGACCGGAGGAGCCCGCAACCACTCCCGCCGCAGGGCGCAGACGC

CGGTCTGCCGCTACGTGCCGAGCTCGCTGGAGATGGACGAGTTCTTCGCCGCCGCCGAGCAGCAGCAA

CACCAGACCTTCAGGGACAAGTAAGAGCATGCTTCCTTCTGCTCTTCTTCACATACTGTAAANAGAAA

CTTGCTAACACTCGACTGTGATGTTGAAATCAGGTACAACTTCTGTCCTGCGAGCGGCTGCCCGCTCC

CCGGGCGGTACGAGTGGACGGTGCTAGACTGCTAGGGCTTCATACCTCACACCACCACCAGGAGCTCC

TCCATTGATCTCTGT

SEQ ID NO: 71

>wheat KRP5A coding

ATGGGCAAGTACATGCGCAAGAGCAAGGCCTCGGGGGAGGTGGCCGTCATGGAGGTCGCCGGCGCGCT

GCTCGGCGTCCGCACCCGCTCCCGCACCCTCGCCGCGCAGCAGCAGCGCGCTCCGTCCCCTTCGCCGC

AGCGCAAGGGCCACGAGGACGGCGACTACCTCGAGCTCAGGAGCAGGAGGCTCGAGAAGCAGCCGCCG

CCGGGGCCCAAGGACAAGGAGGACGCGCCGCAGCCGCCGGCCGCCGGTGGGAGGAGGATGGAGCAGGC

GCCGTCGTCGTTCGCCGCCGAGGGCTTCGAGGCCGACCTCGAGGTCTCCTTCGGCGACAACGTCCTGG

ACTGGGACGCCACCGACAGGGGCGCCAGGGAGACGACGCCGTGCAGCCTCATCTACAGCTCGGAGACG

ATGAGCACCCCCGGGTCGGCGACCGGAGGAGCCCGCAACCACTCCCGCCGCAGGGCGCAGACGCCGGT

CTGCCGCTACGTGCCGAGCTCGCTGGAGATGGACGAGTTCTTCGCCGCCGCCGAGCAGCAGCAACACC

-continued

AGACCTTCAGGGACAAGTACAACTTCTGTCCTGCGAGGGGCTGCCCGCTCCCCGGGCGGTACGAGTGG

ACGGTGCTAGACTGCTAG

SEQ ID NO: 72

>wheat KRP5A protein

M G K Y M R K S K A S G E V A V M E V A G A L L G V R T R S R T L A

A Q Q Q R A P S P S P Q R K G H E D G D Y L E L R S R R L E K Q P P

P G P K D K E D A P Q P P A A G G R R M E Q A P S S F A A E G F E A

D L E V S F G D N V L D W D A T D R G A R E T T P C S L I Y S S E T

M S T P G S A T G G A R N H S R R R A Q T P V C R Y V P S S L E M D

E F F A A A E Q Q Q H Q T F R D K Y N F C P A R G C P L P G R Y E W

T V L D C *

SEQ ID NO: 73

>wheat KRP5B genomic

CTCCCCATTATTCCGCGATTCCCCTCCCCTCCCCTCCCTCCCAGCCAGCTGCCCACCGGAAGCAGAGG

GAAGCAGAGGAGAGGCCGGGGCCGGCGCCATGGGGAAGTACATGCGCAAGAGCAAGCCCTCGGGGGAG

GTGGCCGTCATGGAGGTCGCCGGCGCGCTGCTCGGCGTCCGCACCCGCTCCCGCACCCTCGCCGCGCA

GCAGCAGCGCGCCCCCTCCCCGTCCCCCTCGCCGCAGCGCAAGGGGCAGGAGGACGGCGACCCCGGGG

CTGGCGACTACCTCGAGCTCAGGAGCAGGCGGCTCGAGAAGCAGCCGCCGCCGGGGGCCAGGGAGAAG

GAGGACGCGCCGCAGCCGGCCGCGAGGAGGGCCGCCGCCGCTGGCGGGAGGAGGATGGAGCAGGCGCC

GTCGTTCGCCGCCGAGGGGTTCGAGGCCGACCTCGAGGTCTCCTTCGGCGACAACGTGCTGGACTGGG

ACGCCACCGACAGGTAACAACAGAGCACCAGTTCTTTCTTTCTTTCTTTCTTCCCCCAATCCCCCCTC

TCCGGTTCAGCCAGCAATCCCTTCTCGCGCCCGGGTGATACCAATACGATTGGGATTTATGCTTTATC

GCGCTCCATTAGCGCCGCCGCGTGGTCTCAAATCTCAACTCTGAAGCGCCGGCAACCTCAAGAATCCC

CTCCCTATGAGTTTCCTCAGACGAGCGCCGACGCTGGTTTTCTTTCTCCCCAGGATTGAAGCGCCCAA

ACATCCACAGCTTCCGCTGATTGTGCCGGGATTCTTGCAAGAATCATCGGTTCTCCGTTTTCAGCCTG

AATGAATTTCCTCAACCATTAGCCGTTGGCGTCCGCTCGAAAGAATCCAAGAAAGAAACGCCTGCCCG

CCGTGTTGACCCGGCGAAAAAGGCCCCCATTTCCCCCCCTCCAAAGAAGCCACCATTTTTCCCGTCCA

AACAATCAAAGGCGCACTCAATCAACCCAACCCCCAATCAAAGTGGGCGCTGCACTTGATTAGTGGAG

CCTCCTCCAGAAATCAGTGGAGCCTCCTCCCCCTCCAGTGGCCGCGGCCGTGGCTCCGCCTTTTCCCG

ATAGTGGCAGAGGAAAGTAGCCCCCTTTCCATTCCCCTTCCCCACCACAGCCGCCCTCCATTGGCTCG

GCCCCAATCTTTCCTCTCCCGCTCTTTCCCGGGCAATTTCAACCCCCCAAAGGCGCCACCGCCGTCGC

ACTCAGGGCCCAGTTTCTCGCCCGCCCGCCCGCCAGCCGCCACCGCCGTGGGCGAAAATGGCATGCAG

CTCATCATCAGCACTTGTACCAGAGCGCCACCGCCGCCATTGAATGCTCGCTGGCCTCCTGTTAGCTT

CCTGACCGGGCCTTGAGTGGACGCCGGACCACGTTTTTGTTCGGAACAGATTTTACTTTGGTCAGGCC

GTGGAAGACCTCAGTAAATATATCTTTCTCCGGCTTATTTAGTTCTACGTATGTTCGCATGATTGATC

CCGTGGTCCCTTTGCCCGGCGTATGCATGTTGGACGCACGCGCCCATTTAGCTCGCTTGCTTGGCCGT

GTTAGGCCAAGTTGTTGCTTGTTTGTCAGCGTCCAGTCATTCAGCGTGCTTGTGCTTGCGCTGCACCA

ATAATCAGGTGCGCCTCACATTGTCTAGCGTGGGGCACTTGCAAGCAATGAAATGGACAAGATCATGC

ATGCTAGAAAATGAATGAGCTGTCGTGTTCGACTTCCTGTAGCTTGCTGTCACCCGAGCTCACCAACC

AAGCTTGCATCTGCAGTAGTAATTTGCAAGACCTCGTGTGCATTTCAGCTTCTGAACCTCATGTGCTG

-continued

TTGGTTGCTTGCAGGGGCACCAGGGAGACGACGCCGTGCAGCCTGATCTACAGCTCGGAGACGATGAG

CACCCCGGGGTCGGCGACGGGAGCCCGCAACCATTCCCGGCGCAGGGCGCAGACGCCGGTGTGCCGCT

ACGTCCCGAGCTCGCTCGAGATGGACGAGTTCTTCGCCGCCGCGGAGCAGCAGCAGCACCAGAGCTTC

AGGGACAAGTAAGAAGAACTCTGCCTCCTCCTCCTCCTCTTCACCTGAACTATGCATACGGCAAA

GCGAAACTTGCTGACACTGGACTGCTCTGATCTAAAAATAACCAGGTACAACTTCTGCCCGGCGAGCG

AGCGCCCGCTCCCGGGGCGGTACGAGTGGACGGTGCTAGACTGCTAGGGCTTCCTCATACCTCACACC

ACCACCACCACCACCAGGAGCTCCTCCATTGATCTCGT

2 Nucleotides (shaded gray) of wheat KRP5B above are changed to G in Express, in addition to having the 1-bp deletion in exon 1. This leads to a P>A change in protein below due to the SNP polymorphisms between UC1041 and Express and perhaps premature truncation of the protein due to the 1-bp deletion. Sequences, as portrayed, are UC-specific.

SEQ ID NO: 74

>wheat KRP5B coding

ATGGGGAAGTACATGCGCAAGAGCAAGCCCTCGGGGGAGGTGGCCGTCAtGGAGGTCGCCGGCGCGCT

GCTCGGCGTCCGCACCCGCTCCCGCACCCTCGCCGCGCAGCAGCAGCGCGCCCCCTCCCCGTCCCCCT

CGCCGCAGCGCAAGGGGCAGGAGGACGGCGACCCCGGGGCTGGCGACTACCTCGAGCTCAGGAGCAGG

CGGCTCGAGAAGCAGCCGCCGCCGGGGGCCAGGGAGAAGGAGGACGCGCCGCAGCCGGCCGCGAGGAG

GGCCGCCGCCGCTGGCGGGAGGAGGATGGAGCAGGCGCCGTCGTTCGCCGCCGAGGGGTTCGAGGCCG

ACCTCGAGGTCTCCTTCGGCGACAACGTGCTGGACTGGGACGCCACCGACAGGGGCACCAGGGAGACG

ACGCCGTGCAGCCTGATCTACAGCTCGGAGACGATGAGCACCCCGGGGTCGGCGACGGGAGCCCGCAA

CCATTCCCGGCGCAGGGCGCAGACGCCGGTGTGCCGCTACGTCCCGAGCTCGCTCGAGATGGACGAGT

TCTTCGCCGCCGCGGAGCAGCAGCAGCACCAGAGCTTCAGGGACAAGTACAACTTCTGCCCGGCGAGC

GAGCGCCCGCTCCCGGGGCGGTACGAGTGGACGGTGCTAGACTGCTAG

SEQ ID NO: 75

>wheat KRP5B protein 1-bp deletion leads to shift in translation frame and assuming correct splice site is used, the protein is predicted to have some new amino acids and truncate prematurely mgkymrkskpsgevavmevagallgvrtrsrtlaaqqqrapspspspqrkgqedgdpgagdylelrsr rlekqpppgarekedapqrprggppplagggwsrrrrspprgsrptsrspsattcwtgtpptgapgrr rraa*

SEQ ID NO: 76

>wheat KRP5D genomic

AATGGGGAAGTACATGCGTAAGAGCAAGGCCTCGGGGGAGGTGGCCGTCATGGAGGTCGCCGGCGCGC

TGCTCGGCGTCCGCACCCGCTCCCGCACCCTCGCCGCGCAGCAGCAGCGCGCTCCGTCCCCTTCGCCG

CAGCGCAAGGGCCACGAGGACGGCGACTACCTCGAGCTCAGGAGCAGGAGGCTCGAGAAGCAGCCGCC

GCCGGGGCCCAAGGACAAGGAGGACGCGCCGCAGCCGCCGGCCGCCGGTGGGAGGGGGATGGAGTCGT

TCGCGGCCGAGGGGTTCGAGGCCGACCTCGAGGTCTCCTTCGGCGACAACGTGCTGGACTGGGACGCC

ACCGACAGGTAAGAACAGAGCACCAGCGCCTTCTTTCCTCCCCCCTTCCTCTCCCCTCAATCCTTCCC

CTCCGGTTCAGTCGGCAATCCCCTCCGCCCCGGCCGATACCAATACGATTGAGGTTTAGGGTTCATAT

CCGCCGCTGTTTCGTTCTGCTCCATTAGCGCCGCCGCTGCGCGGCCTCGAATCTCAACACGAATCCCC

TCCCCTCTCAAACGAGCGCCGCCGCTGGCCCGCTGGTTTTCTCCACAGGATTGAGCCAAACCTTGTGC

TGATTTCGCCCGGATGCTTGCGGGAATAATCCCTTGCAGTTTCCTGATTTTCCTCAAGCTGGAGCCGT

-continued

TGGCCGTAGCTTTGAAAGAATCCAAGAAACGCCTGCCCGCCGTGTTGACCCGGCGAAAAAGGGCCCCC

ATTTTCCCCCCTCCAAAAAAGCCGCCATTTTTCCCGGCCAAACAAAGATGCATCCATCAAGGCGCACT

CAATCAACCCCCAATCAAAGTGGGCGCTGCACTCGATTAGTGGAGCCTCCTCCTCCAGTGGCCGTGGC

CTTTTCCCCGTAGTGGCAGGGGAAAGTAGCCTTCCCCACCATAGCCGCCCTCCATTGGCTTGGCCTCA

ATCTTTCCCAACAGCAACCAGAGGGAGAGGCCCCTCTCCCGCTCTTTCGCCAGCAATTTCAATCCCCC

AAAGGCGCCACCGCCGTCGCGGTCAGGGCCCCATTTCTCGCCCGCCCGCCAGTCGCCACCGCCGTGGG

TGAAAATGGCTTGCTGCTCATCATTGGCCCCTTGTACCAGAGCGCCACCGCCGCCATTGAATGCTTGCT

GGCCTCTTGTTAGCTTCCTGACCGGACGTTGAATGGACACCGGACCACGTTATTGTTCAGACGCTTGG

GGTGAAAGGGAGCTGCCTCCGTTAAATTACCTGGTGTTGTGAGTGCACCAGCCACTTGAACAGCACAA

ATTTTACTTACTGGTAGTTCAGGCCTTGGAAGACCTCAGTAAATATATCTTTCTCCGGCTTATTTAAT

TCTACTTACGTTCGTATGATTGATCTCGTGGTCCCGTTGTCCGGCGTATGCATGTTGAACGCGCCCAT

TTAGCTTGCTTGGCCGTGTTAGGCCAAGTTGTTGTTTGTTTGTCAGCATCCAGTCATTCAGTGTGCTT

GTGCTGCACCAATTATCAGGTACACCTGACATTGTCTAGCGTGGGGCACTTGCAAATAATGAAATGGA

CAAAATCATGCTAGAACATGAGCTGTCGTGTTCAACTTCCTGTAGCTTGGTCTCATCTGAGCTCACCA

ACCCAGCTTGCATCTGCAGTAATTTGCAAGACCTCGTGTGCATTTCAGCTTCTGAACCTCATGTTGCT

TGCAGGGGCGCCAGGGAGACGACGCCGTGCAGCCTGATCTACAGCTCGGAGACGATGAGCACCCCCGG

GTCGGCGACCGGGGCCCGCAACCATTCCCGCCGCAGGGCGCAGACGCCGGTCTGCCGCTACGTCCCGA

GCTCGCTCGAGATGGACGAGTTCTTCGCCGCCGCGGAGCAGCAGCAACACCAGACCTTCAGGGAGAAG

TAAGAACTCTGCCTCCTCCTACCACCATCATTTAAACATGCTCACTGAAGATCAAGCTTCTTGTTCAT

ACAATTGTTCTAACACTCGCTGCTTCATTCTAATCAGGTACAACTTCTGTCCCGCGAGCGAGCGCCCG

CTCCCCGGACGGTACGAGTGGACGGTGCTGGACTGCTAGGGCTTCTTCATACCTCACATCACCACCAC

CACCAGGAGCTCCTCCATTGATCTCTGTAACACCAGAATGACCACCACCATCAGCAGCAGCAGCAGCA

TGTCATATGCCGTGGGCGCGATGCAAATGCAGTAGCGTTAGGTTTCTGATTCACCTGTTGTAAAAAC

TTAGAGTTAGCCCGCAGTCAGCAGTAGCTCAGCCAGCCAGCCATCTCTCAGCCTGATCCCCAACCTCA

CTGTAACCGTCGTTAGTTAACAACATCTCATTTCCGTAGGCTCTAGCTTGATTAGCAGCTCGGTTATC

TTCTGTATCCCGGTCCTCCATCAATGAATGAATCANAGCTAGATTTATTTT

SEQ ID NO: 77

>wheat KRP5D coding

ATGGGGAAGTACATGCGTAAGAGCAAGGCCTCGGGGGAGGTGGCCGTCATGGAGGTCGCCGGCGCGCT

GCTCGGCGTCCGCACCCGCTCCCGCACCCTCGCCGCGCAGCAGCAGCGCGCTCCGTCCCCTTCGCCGC

AGCGCAAGGGCCACGAGGACGGCGACTACCTCGAGCTCAGGAGCAGGAGGCTCGAGAAGCAGCCGCCG

CCGGGGCCCAAGGACAAGGAGGACGCGCCGCAGCCGCCGGCCGCCGGTGGGAGGGGGATGGAGTCGTT

CGCGGCCGAGGGGTTCGAGGCCGACCTCGAGGTCTCCTTCGGCGACAACGTGCTGGACTGGGACGCCA

CCGACAGGGGCGCCAGGGAGACGACGCCGTGCAGCCTGATCTACAGCTCGGAGACGATGAGCACCCCC

GGGTCGGCGACCGGGGCCCGCAACCATTCCCGCCGCAGGGCGCAGACGCCGGTCTGCCGCTACGTCCC

GAGCTCGCTCGAGATGGACGAGTTCTTCGCCGCCGCGGAGCAGCAGCAACACCAGACCTTCAGGGAGA

AGTACAACTTCTGTCCCGCGAGCGAGCGCCCGCTCCCCGGACGGTACGAGTGGACGGTGCTGGACTGC

TAG

SEQ ID NO: 78

>wheat KRP5D protein

M G K Y M R K S K A S G E V A V M E V A G A L L G V R T R S R T L A

A Q Q Q R A P S P S P Q R K G H E D G D Y L E L R S R R L E K Q P P

-continued

P G P K D K E D A P Q P P A A G G R G M E S F A A E G F E A D L E V

S F G D N V L D W D A T D R G A R E T T P C S L I Y S S E T M S T P

G S A T G A R N H S R R R A Q T P V C R Y V P S S L E M D E F F A A

A E Q Q Q H Q T F R E K Y N F C P A S E R P L P G R Y E W T V L D C

Stop

SEQ ID NO: 79

>OsKRP2 protein
MGKKKKRDGAAARRQARVVVGGVRTRAAVTARRVVASAEEGCGLVGRGGGGGSGGDDGEGGCYLRLRS

RRLPFVAAAVVSSRREEALGDSVAEAASSSSSRAVELLGCSGEEEAMAEKVCTQAGEDHDEESSVGDS

GCGRERSATTPSSRRPPGDADSSDAESNQEAKQQMCRRSSTTSAAAFHAGATTRSFRMMAPPAAAAEI

EEFLAAAERSEAERFAAKYNFDVVRGVPLDAGGAGRFEWTAVGSG

SEQ ID NO: 80

>OsKRP3 protein
MGKYLRSSCKQQQQPSSPAAVASVAAAAVSSYSYLTLRSGRRVPAAAAAAGGSACRRRHRRGGRRGCA

KNGAGSARACGARSPTSSASSGQRRRCEAVECSHGGGRAELSRSPPLGNSVVVVSGDVVSGERKSLKP

NSCSREVAAEHAGEHKHNPAAAAAAGRRPPLSPPEAEIEAFFAAAELAERRRFAEKYNYDIALDRPLQ

GRYEWEPVST

SEQ ID NO: 81

>OsKRP4 protein
MGKYMRKAKVVVSGEVVAAAVMELAAAPLGVRTRARSLALQKRQGGEYLELRSRRLEKLPPPPPPPPR

RRATAAAATADATAAESAEAEVSFGGENVLELEAMERNTRETTPCSLIRDPDTISTPGSTTRRSHSSS

HCKVQTPVRHNIIPASAELEAFFAAEEQRQRQAFIDKYNFDPVNDCPLPGRFEWVKLD

SEQ ID NO: 82

>OsKRP5 protein
MGKYMRKGKVSGEVAVMEVGGALLGVRTRSRTLALQRTTSSQKPPEKGEGDPGAGAGAGAEYLELRSR

RLEKPPPHTPPAKEKETARRASAAAAAAVRMPAAPQAAEEFEAEVEVSFGDNVLDLDGDAMERSTRET

TPCSLIRSSEMISTPGSTTKTNTSISSRRRMETSVCRYVPSSLEMEEFFAAAEQQQHQAFRERYNFCP

VNDCPLPGRYEWTRLDC (ZmKRP1 and ZmKRP2 sequences were those in Coelho et al. (2005), Cyclin-dependent kinae inhibitors in maize endosperm and their potential role in endoreduplication, Plant Physiology, 138: 2323-2336)

SEQ ID NO: 83

>ZmKRP1 Coehlo
MGKYMRKAKASSEVVIMDVAAAPLGVRTRARALALQRLQEQQTQWEEGAGGEYLELRNRRLEKLPPPP

ATTRRSGGRKAAAEAAATKEAEASYGENMLELEAMERITRETTPCSLINTQMTSTPGSTRSSHSCHRR

VNAPPVHAVPSSREMNEYFAAEQRRQQQDFIDKYNFDPANDCPLPGRFEWVKLD

SEQ ID NO: 84

>ZmKRP2 Coehlo
MGKYMRKCRGAAGAEVAAVEVTQVVGVRTRSRSAAATGGVAKVAPRRKRAPAGEPAAAVSAGGDGGSC

YIHLRSRMLFMAPPQPQPSVDSVPTPVEAADGAAGQQGAALAAGLSRCSSTASSVNLGLGGQRGSHTC

RSYDAAEAGGDHVLVDVSAASNSGSGPDRERRETTPSSRAHGELSDLESDLAGHKTGPSLPAATPAAE

LIVPPAHEIQEFFAAAEAAQAKRFASKYNFDFVRGVPLDAGGRFEWAPVVSI

SEQ ID NO: 85

>ZmKRP6 (NM_001156360)
MGKYMRKCRGAAGAEVATVEVTQVVGVRTRSRSAAATGGVAKVVAPRRNRAPAGEPAASVGAGGDGGS

CYIHLRSRMLFMAPPQPQPPSVPTPAEAADGAAGQQGAALAAGLSRCSSTASSVHVGGQRGSHTCRSD

-continued

DAAEAGGDHVLVVXVSASNSGSGPDRERRETTPSSRAHGELSDLESDLAGHKTGPSLPAATPAAELIV

PPAHEIQEFFAAAEAAQAKRFASKYNFDFVRGVPLDAGGRFEWAPVVSI

SEQ ID NO: 86

>ZmKRP7
VAAVEVTQVVGVRTRSRSAAATGGVAKVVAPRRKRAPAGEPAASVGAGGDGGSCYIHLRSRMLFMAPP

QPQPPSVPTPAEAADGAAGQQGAALAAGLSRCSSTASSVHVGGQRGSHTCRSDDAAEAGGDHVLVDVS

AASNSGSGPDRERRETTPSSRAHGELSDLESDLAGHKTGPSLPAATPAAELIVPPAHEIQEFFAAAEA

AQAKRFASKYNFDFVRGVPLDAGGRFEWAPVVSI

SEQ ID NO: 87

>ZmKRP8
MGKYMRKRRGAAGEGVAAVEVSQVVGVRTRSRSAAATGGGVAKVAPPRRKKALLPAANETASGEPGAV

GGGGGDGGSCCYIHLRSRMLFMAAPQQQPSAAPTPAEAAGAAQQGGVVALAAGLSRCSSTASTVDVGG

QQPASGSHACRSDAAEVAGDHVPDVVTASNSGSVPDRERRETTPSSSRAHGGELSDLESDLVGWQKTG

CSSSPATTTSAAELIVPPAQEIQEFFAA

The invention claimed is:

1. A method of increasing seed weight, seed size, seed number and/or yield of a plant of a *Triticum* species, comprising introducing one or more non-naturally occurring mutations into one or more KRP genes in the plant, wherein the one or more non-naturally occurring mutation comprises a G to A substitution at nucleotide 758 from the start condon of a nucleotide sequence as set forth in SEQ ID NO: 49 of a *Triticum* KRP2A gene.

2. A method of producing a plant of a *Triticum* species with increased seed size, seed weight, seed number and/or yield compared to a wild type plant, comprising:

i) making a cross between a first plant of a *Triticum* species and a second plant of a *Triticum* species to produce an F1 plant, wherein the first plant of the *Triticum* species comprises one or more non-naturally occurring mutations in one or more KRP genes in the plant, wherein the one of more non-naturally occurring mutation comprises a G to A substitution at nucleotide 758 from the start condon of a nucleotide sequence as set forth in SEQ ID NO: 49 of a *Triticum* KRP2A gene.

3. The method of claim 2, wherein the method further comprises:

ii) backcrossing the F1 plant to the first or the second plant of the *Triticum* species; and iii) repeating the backcrossing step to generate a near isogenic line, wherein the one or more non-naturally occurring mutations comprising a G to A substitution at nucleotide 758 from the start codon of a nucleotide sequence as set forth in SEQ ID NO: 49 in the first plant of the *Triticum* species are integrated into the genome of the near isogenic line.

* * * * *